United States Patent
Lipschultz et al.

(10) Patent No.: US 11,623,043 B2
(45) Date of Patent: Apr. 11, 2023

(54) PARENTERAL NUTRITION DIAGNOSTIC SYSTEM, APPARATUS, AND METHOD

(71) Applicants: Baxter International Inc., Deerfield, IL (US); BAXTER HEALTHCARE SA, Glattpark (CH)

(72) Inventors: Stephen A. Lipschultz, Highland Park, IL (US); Nigel M. Parsad, Evanston, IL (US); Jonathan Silverstein, Evanston, IL (US)

(73) Assignees: Baxter International Inc., Deerfield, IL (US); Baxter Heatlhcare SA, Glattpark (CH)

( * ) Notice: Subject to any disclaimer, the term of this patent is extended or adjusted under 35 U.S.C. 154(b) by 895 days.

(21) Appl. No.: 15/970,970

(22) Filed: May 4, 2018

(65) Prior Publication Data

US 2018/0326149 A1    Nov. 15, 2018

Related U.S. Application Data

(60) Provisional application No. 62/503,670, filed on May 9, 2017.

(51) Int. Cl.
  *A61M 5/172*    (2006.01)
  *G16H 50/20*    (2018.01)
  (Continued)

(52) U.S. Cl.
  CPC .......... *A61M 5/1723* (2013.01); *A61B 5/4519* (2013.01); *A61B 5/4869* (2013.01);
  (Continued)

(58) Field of Classification Search
  CPC ..... A61B 5/4519; A61B 5/4869; A61B 6/032; A61B 6/463; A61B 6/5205; A61B 6/5217;
  (Continued)

(56) References Cited

U.S. PATENT DOCUMENTS 7,947,303 B2    5/2011   Kessler et al.
2009/0175407 A1*  7/2009   Harer .................. G01N 23/046
                                                    378/20

(Continued)

FOREIGN PATENT DOCUMENTS

EP           0226268 B1    2/1992
JP           2004081394    3/2004
(Continued)

OTHER PUBLICATIONS

Casaer, M.P. et al. "Impactof Early Parenteral Nutrition on Muscle and Adipose Tissue Compartments During Critical Illness". Crit Care Med Oct. 2013;41(10):2298-2309. (Year: 2013).*

(Continued)

*Primary Examiner* — Boniface Ngathi N
*Assistant Examiner* — Milton Truong
(74) *Attorney, Agent, or Firm* — K&L Gates LLP

(57) ABSTRACT

A parenteral nutritional diagnostic system, apparatus, and method are disclosed. In an example embodiment, a parenteral nutritional diagnostic apparatus determines muscle quantity and muscle quality of a patient's psoas muscle to determine a nutritional status of the patient. An image interface is configured to receive a medical image including radiodensity data related to imaged tissue of the patient. The apparatus also includes a processor configured to use the medical image to determine a tissue surface area for each different value of radiodensity and determine a distribution of the tissue surface area for each radiodensity value. The processor is configured to determine muscle quality by locating a soft tissue peak within the distribution that corresponds to a local peak in at a region related to at least one of muscle tissue, organ tissue, and intramuscular adipose tissue. The processor determines the nutritional status of the patient based on soft tissue peak.

22 Claims, 17 Drawing Sheets

(51) Int. Cl.

| | |
|---|---|
| G16H 20/60 | (2018.01) |
| A61B 6/00 | (2006.01) |
| A61B 5/00 | (2006.01) |
| G06T 7/00 | (2017.01) |
| G16H 30/20 | (2018.01) |
| A61B 6/03 | (2006.01) |
| G16H 30/40 | (2018.01) |
| A61M 5/145 | (2006.01) |
| A61M 5/142 | (2006.01) |

(52) U.S. Cl.
CPC ............ *A61B 6/032* (2013.01); *A61B 6/463* (2013.01); *A61B 6/5205* (2013.01); *A61B 6/5217* (2013.01); *G06T 7/0014* (2013.01); *G16H 20/60* (2018.01); *G16H 30/20* (2018.01); *G16H 30/40* (2018.01); *G16H 50/20* (2018.01); *A61M 5/14228* (2013.01); *A61M 5/14546* (2013.01); *A61M 2205/3584* (2013.01); *G06T 2207/10081* (2013.01); *G06T 2207/20072* (2013.01); *G06T 2207/30008* (2013.01)

(58) Field of Classification Search
CPC ........... G06T 2207/10081; G06T 2207/20072; G16H 20/17; G16H 20/60; G16H 50/20; A61M 5/1723
See application file for complete search history.

(56) References Cited

U.S. PATENT DOCUMENTS

| | | | |
|---|---|---|---|
| 2013/0020226 A1 | 1/2013 | Abele et al. | |
| 2015/0019138 A1* | 1/2015 | Kaucky | G16H 20/10 702/19 |
| 2015/0265236 A1* | 9/2015 | Garner | G06T 7/60 600/425 |
| 2015/0297549 A1 | 10/2015 | Schlotzer et al. | |
| 2016/0058673 A1* | 3/2016 | Francis | G16H 20/17 604/65 |
| 2016/0374629 A1* | 12/2016 | Kawata | A61B 6/4035 378/19 |
| 2017/0055926 A1* | 3/2017 | Takahashi | A61B 6/5217 |
| 2017/0148156 A1* | 5/2017 | Bregman-Amitai | A61B 6/481 |
| 2017/0263023 A1* | 9/2017 | Zhou | G06T 19/00 |

FOREIGN PATENT DOCUMENTS

| | | |
|---|---|---|
| JP | 4405716 | 1/2010 |
| JP | 2013118914 A2 | 6/2013 |
| WO | 2004109580 | 12/2004 |
| WO | 2011139232 | 11/2011 |

OTHER PUBLICATIONS

Prado, C.M.M. et al. "Prevalence and clinical implications of sarcopenic obesity in patients with solid tumours of the respiratory and gastrointestinal tracts: a population-based study". Lancet Oncol 2008; 9: 629-35 (Year: 2008).*

Aubrey, J. et al. "Measurement of skeletal muscle radiation attenuation and basis of its biological variation". Acta Physiologica, 210, 489-497, 2014. (Year: 2014).*

Martin. L, et al. "Cancer Cachexia in the Age of Obesity: Skeletal Muscle Depletion is a Powerful Prognostic Factor, Independent of Body Mass Index". J Clin Oncol 31:1539-1547. 2013 (Year: 2013).*

Muscaritoli M., PN in cancer 2014; "What is the role of PN in nutritional support of cancer patients"; Baxter Global Oncology Advisory Board Meeting, Barcelona, Spain Apr. 25-26, 2014—48 pages.

Baracos, "What are the most valuable nutrition assessment indicators to determine need for nutrition support of cancer patients," Department of Oncology, University of Alberta—33 pages.

"Muscle assessment in advanced cancer patients", Am J. Clin Nutr, 1992 Baxter oncology advisory board meeting Barcelona Apr. 25, 2014—40 pages.

Jann Arends, "PN in Cancer Patients Evidence Gaps and How to Fill Them," Tumor Biology Center Freiburg Germany;—84 pages.

Michael J. Tisdale, "Cachexia in Cancer Patients," Nature Reviews Cancer, vol. 2, Nov. 2002, 2002 Nature Publishing Group, www.nature.com/reviews/cancer—pp. 862-871.

Kent Lundholm, et al., "Palliative Nutritional Intervention in Addition to Cyclooxygenase and Erythropoietin Treatment for Patients with Malignant Disease Effects on Survival, Metabolism, and Function," Cancer May 1, 2004, vol. 100, No. 9—pp. 1967-1977.

Carlo Prado, et al., "Body Composition as an independent Determinant of 5-Fluorouracil-Based Chemotherapy Toxicity," Clin Cancer Res (2007) vol. 13, No. 11 Jun. 1, 2007—pp. 3264-3268.

Kevin D. Hall et al., "Computational modeling of cancer cachexia," Current opinion in Clinical Nutrition and Metabolic Care (2008), vol. 11—pp. 214-221.

S. Antoun et al., "Low body mass index and sarcopenia associated with dose-limiting toxicity of sorafenib in patients with renal cell carcinoma," Annals of Oncology, vol. 21, No. 8, Aug. 2010—pp. 1594-1598.

Carla M.M. Prado, "Sarcopenia as a Determinant of Chemotherapy Toxicity and Time to Tumor Progression in Metastatic Breast Cancer Patients Receiving Capecitabine Treatment," Clin Cancer Res (2000), vol. 15, No. 8, Apr. 15, 2009, www.aacrjournals.org— pp. 2920-2926.

Kenneth Fearon et al., "Definition and classification of cancer cachexia: an international consensus," www.thelancet/oncology, vol. 12, May 2011—pp. 489-495.

Robert H. Coker et al., "Bedrest and sarcopenia," Ageing: biology and nutrition, vol. 15, No. 1, Jan. 2012, www.co-clinicalnutrition.com—pp. 7-11.

Olivier Mir, et al., "Sarcopenia Predicts Early Dose-Limiting Toxicities and Pharmacokinetics of Sorafenib in Patients with Hepatocellular Carcinoma," vol. 7, Issue 5, May 2012, www.plosone.org—pp. 1-7.

Dechaphunkul et al., "Malnutrition assessment in patients with cancers of the head and neck: A call to action and consensus," Critical Reviews in Oncology/Hematology 88 (2012)—pp. 459-476.

Huillard et al., Sarcopenia and body mass index predict sunitinib-induced early dose-limiting toxicities in renal cancer patients, British Journal of Cancer, www.bjcancer.com/DOI:10.1038/bjc.2013.58—pp. 1034-1041.

Sharma et al., Association of Sarcopenia with eGFR arid Misclassification of Obesity in Adults with CKD in the United States, Clinical Journal of the American Society of Nephrology, vol. 9, Dec. 2014, www.cjasn.org—pp. 2079-2088.

Hebuterne, "Prevalence of Malnutrition and Current Use of Nutrition Support in Patients With Cancer," Journal of Parenteral and Enteral Nutrition, vol. 38, No. 2, Feb. 2014, pp. 196-204.

Vivane Angelina de Souza et al., "Sarcopenia in Chronic Kidney Disease," J Bras Nefro. vol. 37, No. 1, (2015)—pp. 98-105.

Johansen et al., "Body composition in chronic kidney disease," Curr Opin Nephrol Hypertens, vol. 24, No. 3, May 2015—pp. 268-275.

Broers et al., Body Composition in Dialysis Patients: a Functional Assessment of Bioimpedance Using Different Production Models, Journal of Renal Nutrition, vol. 25, No. 2, Mar. 2015—pp. 121-128.

Cohen et al., "Muscle wasting in disease: molecular mechanims and promising therapies," Nature Reviews/Drug Discovery, vol. 14, Jan. 2015, www.nature.com/reviews/drugdisc—pp. 58-74.

Drissi et al., "Nutrition care in patients with cancer: a retrospective multicenter analysis of current practice—indications for further studies?," Clinical Nutrition vol. 34 (2015)—pp. 207-211.

Martin et al., "Diagnositc Criteria for the Classification of Cancer-Associated Weight Loss," J Clin Oncol, vol. 33, No. 1 Jan. 1, 2015—pp. 90-99.

(56) References Cited

OTHER PUBLICATIONS

ERS European Respiratory Society, ERJ open research, "A practical measurement of thoracic sarcopenia: correlation with clinical parameters and outcomes in advanced lunch cancer, Original Research Letter" vol. 2, (2015)—pp. 1-3.

Buch et al., "Muscle function and fat content in relation to sarcopenia, obesity and frailty of old age—An overview," Experimental Gerontology, vol. 76 (2016)—pp. 25-32.

Huang et al., "Impact of different sarcopenia stages on the postoperative outcomes after radical gastrectomy for gastric cancer," Article in Press (Surgery 2016)—pp. 1-14.

Ilich et al., "Osteosarcopenic Obesity Syndrome: What Is It and How Can It Be Identified and Diagnosed," Current Gerontology and Geriatrics Research, vol. 2016, Article ID 73216973, http://dx.doi.org/10.1155/2016/7325973—7 pages.

Kalinkovich, Alexander, Livshits, Gregory, Sarcopenic obesity or obese sarcopenia: a cross talk between age-associated adipose tissue and skeletal muscle inflammation as a main mechanism of the pathogenesis, Ageing Research Reviews, http://dx.doi.org/10.1016/j.arr.2016.09.008, Accepted Manuscript—pp. 1-80, title page and 4 figures.

Kizilarslanoglu et al., "Sarcopenia in critically ill patients" Japanese Society of Anesthesiologists, vol. 30., Published online: Jul. 4, 2016—pp. 884-890.

McCullough et al., "Nutritional Deficiencies and Sarcopenia in heart Failure: A Therapeutic Opportunity to Reduce Hospitalization and Death," Reviews in cardiovascular Medicine, vol. 17, Suppl. 1 (2016)—pp. S30-S39.

Mitchell et al., "Human Skeletal muscle Protein Metabolism Responses to Amino Acid Nutrition," American Society for Nutrtion, Adv. Nutr 2016 (Suppl.), downloaded from advances.nutrition.org at University of California Davis on Oct. 21, 2016—pp. 828S-838S.

Nishida et al., "Preoperative Sarcopenia Strongly Influences the Risk of Postoperative Pancreatic Fistual Formation After Pancreaticoduodenectomy," J Gastrointest Surg, vol. 20—pp. 1586-1594.

Paknikar et al., "Psoas muscle size o=as a frailty measure for open and transcatheter aortic valve replacement," The Journal of Thoracic and Cardiovascular Surgery, vol. 151, No. 3—pp. 745-751.

Romanello et al., "Mitochondrial Quality Control and Muscle Mass Maintenance," Frontiers in Physiology, vol. 6, Article 422 (2016), www.frontiersin.org—pp. 1-21.

Ren et al., "Sarcopenia in patients undergoing maintenance hemodialysis: incidence rate, risk factors and its effect on survival risk," Renal Failure, vol. 38, No. 3 (2016), http//:dx.doi.org/10.3109/0886022X.2015.1132173—pp. 364-371.

Thomas et al., "Protein Supplementation Does Not Significantly Augment the Effects of Resistance Exercise Training in Older Adults: A Systematic Review," JAMDA vol. 17 (2016)—959.e1-959.e9.

Mourtzakis M. et al., "A practical and precise approach to quantification of body composition in cancer patients using computed tomography images acquired during routine care," Appl. Physiol. Nutr Metab., vol. 33, (2008) pp. 997-1006.

Lieffers J. et al., "A viscerally driven cachexia syndrome in patients with advanced colorectal cancer: contributions of organ and tumor mass to whole-body energy demands," Am J. Clin Nutr 2009, vol. 89, pp. 1173-1179.

Pupim, L. et al., "Accelerated lean body mass loss in incident chronic dialysis patients with diabetes mellitus," Kidney International, vol. 68 (2005), pp. 2368-2374.

Safer U. et al., "Accurate diagnosis of sarcopenia in the elderly requires correct measurement of muscle mass," Clinical Nutrition, vol. 32 (2013), p. 662.

Puthucheary, Z. et al., "Acute Skeletal Muscle Wasting n Critical Illness," JAMA, vol. 310, No. 15, Oct. 16, 2013, pp. 1591-1600.

Englesbe, M. et al., "Analytic Morphomics, Core Muscle Size, and Surgical Outcomes," Annals of Surgery, vol. 256, No. 2, Aug. 2012, www.annalsofsurgery.com, pp. 255-261.

Chung, H. et al., "Automated segmentaton of muscle and adipose tissue on CT images for human body composition analysis", White Paper, 8 pages.

Visser, M. et al., "The bioelectrical impedance phase angle as an indicator of undernutrition and adverse clinical outcome in cardiac surgical patients," Clinical Nutrition, vol. 31 (2012), pp. 981-986.

Wirth, R. et al., Bioelectric impedance phase angle is associated with hospital mortality of geriatric patients, Archives of Gerontology and Geriatrics, vol. 51 (2010), pp. 290-204.

Cristina, Maria et al., "Bioelectrical impedance analysis: population reference values for phase angle by age and sex," American Journal of Clinical Nutrition, vol. 82 (2005), pp. 49-52.

Vledder, M. et al., "Body composition and outcome in patients undergoing resection of colorectal liver metastases," British Journal of Surgery, vol. 99 (2012), pp. 550-557.

Popuri, K. et al., "Body Composition Assessment in Axial CT Images using FEM-based Automatic Segmentation of Skeletal Muscle," IEEE Transaction of Medical Imaging, submission date Sep. 11, 2015, pp. 2-13.

Mehlig et al., Body composition by Dual-energy X-ray spectrometry and Bioelectrcial Impedenace Spectroscopy in a health population at age 75 and 80, e-SPEN Journal (2014), doi: 10.1016/j.clnme.2014.11.001, 25 pages.

Kyle, U. et al., "Body Composition Interpretation: Contributions of the Fat-Free Mass Index and the Body Fat Mass Index," Nutrition, vol. 19, Nos. 7/8 (2003), 8 pages.

Bourdel-Marchasson, I. et al., "One-Year Mortality in Older Patients with Cancer: Development and External Validation of an MNA-Based Prognostic Score," PLOS ONE / DO1L10.1371/journal.pone.0148523, Feb. 9, 2016, pp. 1-16.

Brewster, D. et al., "Measuring visceral fat, subcutaneous fat and skeletal muscle area changes by computed tomography in acute pancreatitis: a retrospective, single-centre study," Critical Care and Resuscitation, vol. 16, No. 1, Mar. 2014, pp. 42-48.

Barbosa-Silva, M. et al., "Can Bioelectrical Impedance Analysis Identify Malnutrition in Preoperative Nutrition Assessment," Nutrition, vol. 19 (2003), pp. 422-426.

Kyle, U. et al., "Can phase angle determined by bioelectrical impedance analysis assess nutritional risk? A comparison between healthy and hospitalized subjects," Clinical Nutrition 31 (2012), pp. 875-881.

Prado, C. et al., "Central tenet of cancer cachexia therapy: do patients with advanced cancer have exploitable anabolic potential?," American Journal of Clinical Nutrition, vol. 98 (2013), pp. 1012-1019.

Cerri, AP. et al., "Sarcopenia and Malnutrition in Acutely Ill Hospitalized Elderly: Prevalence and Outcomes," Clinical Nutrition (2014), doi: 10.1016/j.clnu.2014.08.2015, 27 pages.

McLean et al., "Criteria for Clinically Relevant Weakness and Low Lean Mass and Their Longitudinal Association With Incident Mobility Impairment and Mortality: The Foundation for the National Institutes of Health (FNIH) Sarcopenia Project," J Gerontol A Biol Sci Med Sci, vol. 69, No. 5, May 2014, pp. 576-583.

Muscaritoli et al., "Consensus definition of sarcopenia, cachexia and pre-cachexia: Joint document elaborated by Special Interest Groups (SIG) "cachexia-anorexia in chronic wasting diseases" and "nutriion geriatrics"" Clinical Nutrition vol. 29 (2010), pp. 154-159.

Hasselager et al., "Core muscle size assessed by perioperative abdominal CT scan is related to mortality, postoperative complications, and hospitalization after major abdominal surgery: a systematic review," Langenbecks Arch Surg, vol. 399 (2014), pp. 287-295.

Sheetz et al., "Cost of Major Surgery in the Sarcopenic Patient," J Am Coll Surg, vol. 217, No. 5, Nov. 2013, pp. 813-818.

Cawthon et al., "Cutpoints for Low Appendicular Lean mass That Identify Older Adults With Clinically Significant Weakness," J Gerontol A Biol Sci Med Sci, vol. 69, No. 5, May 2014, pp. 567-575.

Quality Assurance and Training Manual—Body Composition Analysis Using Compute Tomography (CT) Imaging Version 1.4, Jan. 1, 2014 pp. 1.1-5.2.

MacDonald et al., "CT Derived Measures of Muscle Mass are Associated With Functional Ability but Not Strength and Power in Patients With Upper GI Cancer," Nutrition and Cancer, p. S53.

(56) References Cited

OTHER PUBLICATIONS

International Search Report PCT/US2018/031093 dated Aug. 1, 2018—6 pages.
Written Opinion of the International Search Authority PCT/US2018/031093 dated Aug. 1, 2018—14 pages.
Rooyackers et al., "Imaging opens possibilities both to target and to evaluate nutrition in critical illness," Critical Care, vol. 18, No. 144 (2014)—3 pages.
Van der Werf, et al., "Percentiles for skeletal muscle index, area and radiation attenuation based on computed tomography imaging in a health Caucasian population," European Journal of Clinical Nutrition, vol. 72 (2018), pp. 288-296, https://doi.org/10.1038/s41430-017-0034-5.
Hanai et al., "Sarcopenia impairs prognosis of patients with liver cirrhosis", Nutrition (2014) Accepted Manuscript—43 pages.
Tan et al., "Sarcopenia in an Overweight or Obese Patient is an Adverse Prognostic Factor in Pancreatic Cancer," Clin Cancer Res (2009) vol. 15, No. 22, Nov. 15, 2009, pp. 6973-6980.
Du et al., "Sarcopenia is a predictor of outcomes in very elderly patients undergoing emergency surgery," Society of University of Surgeons, Surgery, Sep. 2014, pp. 521-527.
Lieffers et al., "Sarcopenia is associated with postoperative infection and delayed recovery for colorectal cancer resection surgery," British Journal of Cancer (2012) vol. 107, pp. 931-936.
Barret et al., Sarcopenia is Linked to Treatment Toxicity in patients With Metastatic Colorectal Cancer, Nutrition and Cancer, vol. 66, No. 4, pp. 583-589.
Cosqueric et al., "Sarcopenia is predictive of nosocomial infection in care of the elderly," British Journal of Nutrition (2006) vol. 96, pp. 895-901.
Antoun et al., "Skeletal Muscle Density Predicts Prognosis in Patients With Metastatic Renal Cell Carcinoma Treated with Targeted Therapies," Cancer, Sep. 15, 2013, pp. 3377-3384.
Correa-de-Araujo et al., "Skeletal Muscle Function Deficit: A New Terminology to Embrace the Evolving Concepts of Sarcopenia and Age-Related Muscle Dysfunction," J Gerontol A Biol Sci Med Sci, vol. 69, No. 5 (2014), pp. 591-594.
Cardinal et al., "Standardized phase angle indicates nutritional status in hospitalized preoperative patients," Nutrition Research, vol. 30 (2010), pp. 594-600.
Khursheed Jeejeebhoy, MBBS, PhD, "Subjective Global Assessment versus Sarcopenia Detected by Computed Tomography", Journal of Parenteral and Enteral Nutrition, vol. 39, No. 3, Mar. 2015, pp. 271-272.
Lee et al, "Surgical Site Infection and Analytic Morphometric Assessment of Body Composition in Patients Undergoing Midline Laparotomy", J Am Coll Surg, vol. 213, No. 2, Aug. 2011.
Studenski et al., "The FNIH Sarcopenia Project: Rationale, Study Description, Conference Recommendations, and Final Estimates", J Gerontol A Biol Sci Med Sci, May 2014, vol. 69, No. 5, pp. 547-558.
Malietzis et al., "The role of body composition evaluation by computerized tomography in determining colorectal cancer treatment outcomes: A systematic review", EJSO the Journal of Cancer Surgery, vol. 41 (2015), pp. 186-196.
Gibson et al., "The role of computed tomography in evaluating body composition and the influence of reduced muscle mass on clinical outcome in abdominal malignancy: a systematic review", European Journal of Clinical Nutrition (2015, pp. 1-8.
Shen et al., "Total body skeletal muscle and adipose tissue volumes: estimation from a single abdominal cross-sectional image," J Appl Physiol, vol. 97 (2004), pp. 2333-2338.
Mijnarends et al., Validity and Reliability of Tools to Measure Muscle Mass, Strength, and Physical Performance in Community-Dwelling Older People: A Systematic Review, JAMDA, vol. 14 (2013), pp. 170-178.
Prado et al., "Lean Tissue Imaging: A New Era for Nutritional Assessment and Intervention", Journal of Parental and Enteral Nutrition, http://pen.sagepub.com/content/early/2014/09/17/0148607114550189, pp. 1-14.

Weijs et al., "Low Skeletal muscle area is a risk factor for mortality in mechanically ventilated critically ill patients", Critical Care (2014), vol. 18:R12, pp. 1-7.
Vandewoude et al., "Malnutrition-Sarcopenia Syndrome: Is This the Future of Nutrition Screening and Assessment for Older Adults", Journal of Aging Research, vol. 2012, Article ID 651570, 8 pages.
Martin, "Cancer Cachexia in the Age of Obesity: Skeletal Muscle Depletion is a Powerful Prognostic Factor, Independent of Body Mass Index", J Clin Oncol, vol. 31, No. 12, Apr. 20, 2013, pp. 1539-1547.
Bunce et al., "Measurement of abdominal muscle thickness using M-mode ultrasound imaging during functional activities", Manual Therapy, vol. 9 (2004), pp. 41-44.
Englesbe et al., "Morphometric Age and Surgical Risk", J Am Coll Surg, vol. 216, No. 5, May 2013, pp. 976-985.
Mostafa et al., "Morphometries as a predictor of perioperative morbidity after lumbar spine surgery", Neurosurg Focus, vol. 39, No. 4:E5, Oct. 2015, pp. 1-9.
Carrero et al., "Muscle atrophy, inflammation and clinical outcome in incident and prevalent dialysis patients", Clinical Nutrition, vol. 27, (2008), pp. 557-564.
M. Jeffrey Mador, M.D., "Muscle Mass, Not Body Weight, Predicts Outcome in Patients with Chronic Obstructive Pulmonary Disease", American Journal of Respiratory and Critical Care Medicine, vol. 166 (2002)—pp. 787-788 (editorials).
Montano-Loza et al., Clinical Gastroenterology and Hepatology, vol. 10, No. 2, pp. 166-173.
Constantin et al., "Novel events in the molecular regulation of muscle mass in critically ill patients", J Physiol 589, vol. 15, vol. 589, No. 15 (2011), pp. 3993-3895.
Pichard et al., "Nutritional assessment: lean body mass depletion at hospital admission is associated with an increased length of stay", Am J Clin Nutr, vol. 79 (2004), pp. 613-618.
Honda, "Obese sarcopenia in patients with end-stage renal disease is associated with inflammation and increased mortality", Am J Clin Nutr (2007) vol. 86 (2007) pp. 633-638.
Caccialanza et al., "Nutrients", vol. 7 (2015) ISSN 2072-6643, www.mdpi-com/journal/nutrients, pp. 1828-1840.
Prado et al., Prevalence and clinical implications of sarcopenic obesity in patients with solid tumours of the respiratory and gastrointestinal tracts: a population-based study, vol. 9, Jul. 2008, pp. 629-635, http://oncology.thelancet.com.
Villasenor et al., "Prevalence and prognostic effect of sarcopenia in breast cancer", J. Cancer Surviv. vol. 6, No. 4, pp. 398-406 Author manuscript; available in PMC Dec. 1, 2013, pp. 1-17.
Cruz-Jentoft et al., "Prevalence of an interventions for sarcopenia in ageing adults: a systematic review. Report of the International Sarcopenia Initiative (EWGSOP and IGS)", Age and Ageing, (2014) vol. 43, pp. 748-759.
Sheean et al., "The Prevalance of Sarcopenia in Patients With Respiratory Failure Classified as Normally Nourished Using Computed Tomography and Subjective Global Assessment", vol. 38, No. 7, Sep. 2014, pp. 873-879.
Arbeille et al.,"Quantificiation of Muscle Volume by Echography: Comparison With MRI Data on Subjects in Long-Term Bed Rest", Ultrasound in Medicine and Biology, vol. 35, No. 7, (2009), pp. 1092-1097.
M.D. Sur et al., "Radiographic Sarcopenia and Self-reported Exhaustion Independently Predict NSQIP Serious Complications After Pancreaticoduodenectomy in Older Adults", Ann Surg Oncol, vol. 22 (2015), pp. 3897-3904.
Englesbe et al.,"Sarcopenia and Mortality after Liver Transplantation", J am Coll Surg, vol. 211, No. 2, Aug. 2010, pp. 271-278.
M.D., Hanna Joseph S., "Sarcopenia and Critical Illness: A Deadly Combination in the Elderly", Journal of Parenteral and Enteral Nutrition, vol. 39, No. 3 Mar. 2015, pp. 273-281.
Laviana et al., "Sarcopenia and Nutrition", Advances in Food and Nutrition Research, vol. 71, Chapter 3, pp. 101-136.
Fukushima et al. "Sarcopenia as a Prognostic Biomarker of Advanced Urothelial Carcinoma", Prognostic Role of Sarcopenia in Advanced UC, PLOS ONE, Jan. 22, 2015, pp. 1-11.

(56) References Cited

OTHER PUBLICATIONS

Sabel et al., "Sarcopenia as a Prognostic Factor among Patients with Stage III Melanoma", Ann Surg Oncol, vol. 18 (2011), pp. 3579-3585.
Sheetz et al., "Decreased core muscle size is associate with worse patient survival following esophagectomy for cancer," Diseases of the Esophagus (2013) vol. 26, pp. 716-722.
Bijlsma et al., "Defining sarcopenia: the impact of different diagnostic criteria on the prevalence of sarcopenia in a large middle aged cohort," AGE vol. 35, pp. 871-881.
Fearon et al., "Definition and classification of cancer cachexia: an international consensus," www.thelancet.com/oncology, vol. 12, May 2011, pp. 489-495.
Vellas et al., Designing Drug Trials for Sarcopenia in Older Adults with Hip Fracture—A Task Force from the International Conference on Frailty and Sarcopenia Research (ICFSR), The Journal of Frailty & Aging, Accepted for Publication May 19, 2014, pp. 1-6.
Fischer et al., "Evaluation of Muscle and Fat Loss as Diagnostic Criteria for Malnutrition," Techniques and Procedures, Nutrition in Clinical Practice, vol. XX, No. X Month 201X, pp. 1-10.
Seki et al. "Evaluation of the technical difficulty performing laparoscopic resection of a rectosigmoid carcinoma: viseral fat reflects technical difficulty more accurately than body mass index," Surg Endosc, vol. 32 (200&0, pp. 929-934.
Dam et al., "An Evidence-Based Comparison of Operational Criteria for the Presence of Sarcopenia," J Gerentol A Biol Sci Med Sci vol. 69, No. 5, May 2014, pp. 584-590.
Braunschweig et al., "Exploitation of Diagnostic Computed Tomography Scans to Assess the Impact of Nutrition Support on Body Composition Changes in Respiratory Failure Patients," Journal of Parenteral and Enteral Nutrtion, vol. 38, No. 7, Sep. 2014, pp. 880-885.
Wouters, "Feast or Famine in the Intensive Care Unit: Does It Really Matter?", Department of Respiratory Diseases Maastricht University Medical Center Maastricht, The Netherlands, American Thoracic Society (Editorials), pp. 523-525.
Jay Soong-Jin Lee et al., "Frailty, core muscle size, and mortality in patients undergoing open abdominal aortic aneurysm repair," J Vasc Surg 2011, vol. 53, pp. 912-917.

Alfonso J. Cruz-Jentoft, "Sarcopenia," Clinical Medicine (2014) vol. 14, No. 2, pp. 183-186.
Alley et al., "Grip Strength Cutpoints for the identification of Clinically Relevant Weakness," J Gerontol A Biol Sci Med Sci, vol. 69, No. 5, pp. 559-566.
Casaer et al., "Impact of Early Parenteral Nutrition on Muscle and Adipose Tissue Compartments During Critical Illness," Critical Care Medicine, vol. 41, No. 10, Oct. 2013, pp. 2298-2309, www.comjournal.org.
Peng et al., "Impact of Sarcopenia on Outcomes Following Resection of Pancreatic Adenocarcinoma," J Gastrointest Surg (2012), vol. 16, pp. 1478-1486 (original article).
Peng et al., "Impact of Sarcopenia on Outcomes Following Resection of Pancreatic Adenocarcinoma," J Gastrointest Surg (2012) August, vol. 16, No. 8, pp. 1-15 (Author Manuscript).
Friedman et al., "Implications of Sarcopenia in Major Surgery," Nutrition in Clinical Practive, vol. 30, No. 2, Apr. 2015, pp. 175-179.
Prado et al., "Lean Tissue Imaging: A New Era for Nutritional Assessment and Intervention," Journal of Parenteral and Enteral Nutrition—http://mc.manuscriptcentral.com/jpen, pp. 1-43.
Bohe et al., "Latency and duration of stimulation of human muscle protein synthesis during continuous infusion of amino acids," Journal of Physiology (2001), vol. 532, No. 2, pp. 575-579.
Wilson et al., "Relation of Lean Body Mass to Health-Related Quality of Life in Persons with HIV," JAIDS Journal of Acquired Immune Deficiency Syndrome, vol. 24, pp. 137-146 (2000).
Huang et al., "Lean Body Mass Predicts Long-Term Survival in Chinese Patients on Peritoneal Dialysis," PLOS ONE vol. 8, Issue 1, Jan. 2013, pp. 1-6.
Han et al., "Lean Mass Index: A Better Predictor of Mortality than Body Mass Index in Elderly Asians," Lean Mass Index and Mortality, vol. 58, No. 2, Feb. 2010, pp. 312-317.
Notice of Reasons for Rejection for JP Application No. 2019-561758 dated Mar. 22, 2022.
India Examination Report for Appln No. 201917048138 dated Feb. 23, 2022.

\* cited by examiner

PARENTERAL NUTRITION DIAGNOSTIC SYSTEM, APPARATUS, AND METHOD

PRIORITY

This application claims priority to and the benefit as a non-provisional application of U.S. Provisional Patent Application No. 62/503,670, filed May 9, 2017, the entire contents of which is hereby incorporated by reference and relied upon.

BACKGROUND

A body's metabolic response to surgery, cancer treatment, injury, infection, or premature birth oftentimes depends upon the transfer of amino acids from lean body mass storage locations to sites of active protein synthesis. In addition, the toxicity of some chemotherapy medications for cancer treatment can depend on the distribution of the medications between fat and lean body mass tissue. Studies have found that deficiencies of total body muscle mass, presumably indicating a deficit in amino acid reserves, may impair the healing supply line, thereby impeding the body's ability to maintain adequate rates of protein synthesis in surgical sites or injured areas. Deficiencies of amino acids can decrease muscle mass, which can impair a body's metabolic response to surgery, treatment, or injury and lead to longer recovery times and an increased postoperative (or post-procedural) risk of developing complications, infections, etc. Altogether, the deficiencies may lead to more hospital return visits, longer hospital stays, and/or less favorable outcomes.

Currently, clinicians are not capable of quantitatively and objectively defining a patient's nutritional status. Oftentimes before a medical procedure is performed, a clinician performs an "eyeball test" or semi-subjective assessment, where a patient's overall nutritional status is determined from visual observation. For instance, a clinician may pinch certain skin areas to determine dehydration and fat content. A clinician may also observe how much fat is around a patient's rib cage to gauge malnutrition or starvation or calculate a patient's body mass index ("BMI") based on weight and height (a patient's weight in kilograms divided by the square of height in meters). In addition to a patient's visual appearance, the clinician may also consult critical physiological parameters such as weight, temperature, and heart rate. In some cases, the clinician may further query a patient regarding how they are feeling (e.g., self-reported exhaustion) to determine an approximate nutritional status.

Unfortunately, the eyeball test and BMI calculation do not provide a medically conclusive nutritional status of a patient since these evaluations are heavily influenced by total body fat mass, and cannot accurately assess muscle mass or muscle quality. Additionally, both of the evaluations rely on determining a patient's fat content, not muscle quantity or muscle quality because skeletal muscle and connective tissue cannot be easily observed. Both of these known assessments may therefore provide a false impression that a patient has an acceptable nutritional status when in fact the patient may have a significant decrease in muscle mass. Further, the eyeball test is based on the subjective evaluation of the clinician and may result in inconsistent application among different clinicians. Another drawback of known evaluation methods is that under certain time-sensitive circumstances, a clinician may not have the opportunity to perform the eyeball test or semi-subjective assessment before a critical medical procedure is performed.

SUMMARY

The example system, apparatus, and method disclosed herein are configured to automatically determine or evaluate internal indicators of a patient's nutritional status to ascertain whether the patient should be considered for nutritional therapy (e.g., a parenteral nutrition therapy) prior to or soon after undergoing an intensive medical procedure. The example system, apparatus, and method disclosed herein generate a measurement of body muscle mass as an indicator of total body protein stores. The muscle mass measurement provides an objective index, value, or indicia that are used to evaluate a patient's individual risk of suffering postoperative complications as a result of a deficiency of amino acids stores.

The example system, apparatus, and method generate a muscle mass measurement(s) by analyzing a cross-sectional slice of a patient's abdomen or mid-section. The cross-sectional slice may comprise a two-dimensional image recorded by a computed tomography ("CT") imaging device. The image shows, for example, radiodensity levels of tissue. The example system, apparatus, and method disclosed herein use the radiodensity levels to determine surface areas of distinguishable tissue types including bone tissue, muscle tissue, fat tissue (e.g., visceral adipose tissue and/or subcutaneous adipose tissue), transitional soft tissue (e.g., transitional epithelium, intramuscular adipose tissue, muscle tissue infiltrated by fat tissue), and organ tissue. The example system, apparatus, and method determine total cross-sectional areas for the different tissue types and determine an amount of muscle tissue relative to fat and transitional soft tissue. The example system, apparatus, and method may identify a patient as likely nutritionally deficient if the amount of muscle tissue relative to fat or transitional soft tissue is below a specified threshold. In some instances, the threshold may be adjusted based on patient demographics, disease state, and/or physiological parameters. The example system, apparatus, and method disclosed herein accordingly provide a diagnostic system to quickly and efficiently determine or evaluate a nutritional status of a patient, which may be used to treat malnourishment prior to or after a surgical procedure or chemotherapy.

In addition to evaluating a nutritional status of a patient, the example system, apparatus, and method disclosed herein are configured to determine, recommend, or select a parenteral nutritional treatment based on the amount of muscle tissue relative to fat or transitional soft tissue. The example system, apparatus, and method may recommend the parenteral nutritional treatment by selecting nutritional administration parameters to program a parenteral nutrition pump. In addition, the example system, apparatus, and method may prepare or recommend the preparation of a nutritional substance (or select a premixed nutritional substance) based on the amount of muscle tissue relative to fat or transitional soft tissue, among other information.

In an example embodiment, a parenteral nutritional diagnostic system includes a CT imaging device configured to perform a scan on a mid-section of a patient and produce a set of two-dimensional images each of a slice at a different cross-sectional height of the mid-section, each two-dimensional image including radiodensity data related to imaged tissue of the patient. The example system also includes a soft tissue analysis server communicatively coupled to the CT imaging device. The soft tissue analysis server is configured to select a target two-dimensional image among the set of two-dimensional images by using the radiodensity data to determine which of the two-dimensional images includes a lowest amount of bone tissue and use the target two-dimensional image to determine a tissue surface or cross-sectional area for each different value or level of radiodensity. The soft tissue analysis server may additionally create a distribution plot of the tissue surface or cross-sectional area for each radiodensity value in Hounsfield Units ("HU"), locate a soft tissue peak within the distribution plot that corresponds to a local peak in the range of −50 HU and 80 HU, and transmit an indication of the soft tissue peak.

The system of the example embodiment further includes a pharmacy preparation system communicatively coupled to the soft tissue analysis server. The pharmacy preparation system is configured to recommend if a parenteral nutritional treatment is to be performed before a medical procedure is to be performed for the patient if the data related to the soft tissue peak is below a predetermined threshold, recommend a nutritional order parameter of the parenteral nutritional treatment based at least in part on the data related to the soft tissue peak, and transmit the recommended nutritional order parameter of the parenteral nutritional treatment. Moreover, the example system includes a parenteral nutrition pump communicatively coupled to the pharmacy preparation system. The parenteral nutrition pump is configured to program a parenteral nutrition infusion therapy based on the received recommended nutritional order parameter of the parenteral nutritional treatment and provide the parenteral nutrition infusion therapy to the patient.

In another example embodiment, a parenteral nutritional diagnostic apparatus includes an image interface communicatively coupled to at least one imaging device. The image interface is configured to receive a set of two-dimensional images each of a slice at a different cross-sectional of a mid-section of a patient. Each two-dimensional image includes radiodensity data related to imaged tissue of the patient. The example apparatus also includes at least one processor configured to select a target two-dimensional image among the set of two-dimensional images that corresponds to a desired area (e.g., an area between a third lumbar vertebra and a fourth lumbar vertebra) of the patient. The at least one processor is also configured to use the target two-dimensional image to determine a tissue area for each different level or value of radiodensity and determine a distribution of the tissue surface or cross-sectional area for each radiodensity value. The at least one processor is also configured to locate a soft tissue peak within the distribution that corresponds to a local peak in a region related to muscle tissue and intramuscular adipose tissue and determine or recommend a nutritional status of the patient based on soft tissue peak and potentially other information.

Additional features and advantages of the disclosed system, method, and apparatus are described in, and will be apparent from, the following Detailed Description and the Figures.

DETAILED DESCRIPTION

The example system, apparatus, and method disclosed herein are related to diagnostically determining or evaluating a nutritional status of a patient. More particularly, the example system, apparatus, and method are directed to evaluating muscle quality and muscle quantity from at least one medical image to assess a patient's post-procedural risk before or after undergoing a medical procedure. In some instances, the example system, apparatus, and method may be used to provide a recommendation that a patient is to receive a nutritional therapy, such as a parenteral nutritional therapy, before or shortly after beginning a medical procedure. The example system, apparatus, and method may also provide recommendations or be used to determine parameters for the nutritional therapy based on muscle quality and/or muscle quantity data.

Studies have shown that body composition (i.e., the proportion of fat and muscle tissue) is related to risk factors associated with medical conditions. Bodies that have relatively less muscle tissue are usually deficient in protein or amino acid reserves, which are used to fuel a body's response to surgery, injury, medical treatment, or disease. Low levels of muscle mass in a body have been found to prolong recovery time and/or increase complications. In addition, low levels of amino acids, or more generally, muscle quantity, have also been linked to increases in toxicity from chemotherapy because the reserves determine the volume of distribution for water-soluble drugs. Lower volumes of muscle mass may cause a standard chemotherapy dose to result in toxic tissue levels. Older patients with sarcopenia, a muscle wasting syndrome that involves the loss of muscle tissue, are especially susceptible to postoperative complications. Additionally, infants and patients that are malnourished, fragile, or anorexic typically have low amino acid reserves.

Figure 1:
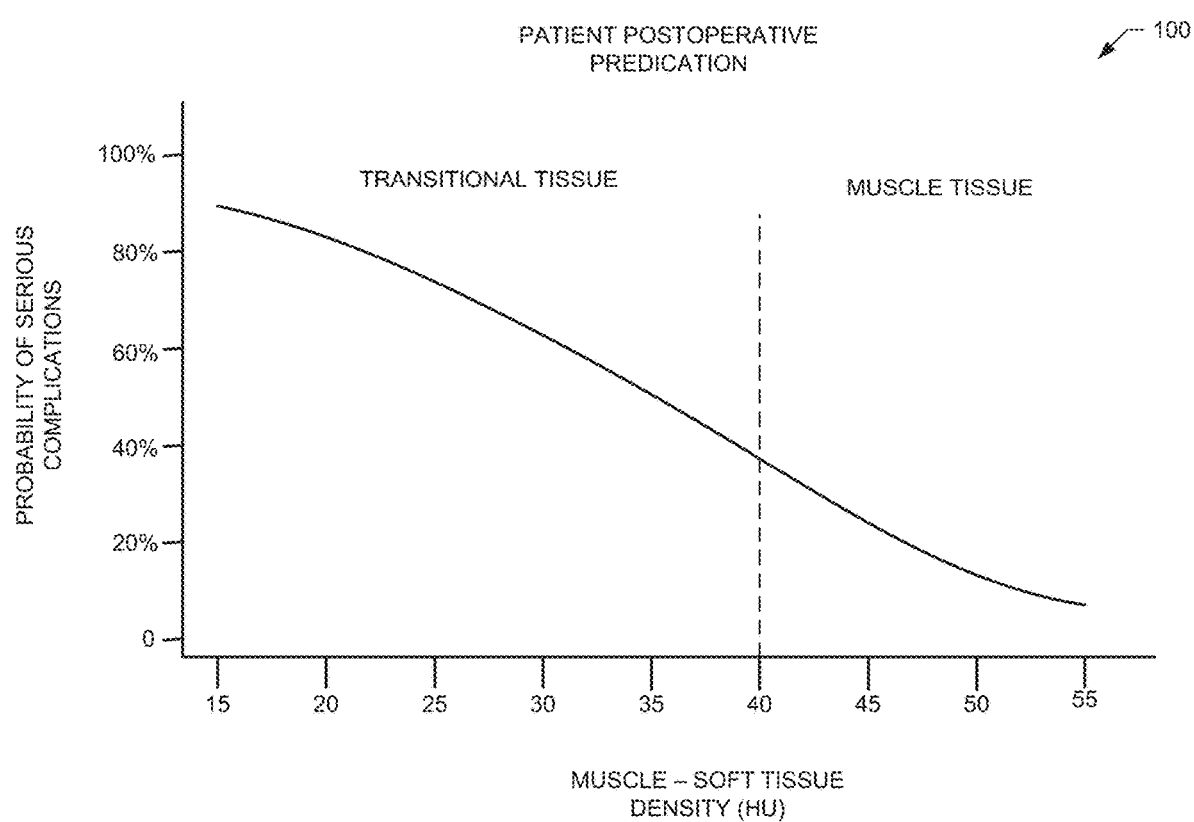
FIG. 1 illustrates a diagram of a graph that conceptually illustrates a relationship between muscle quality and postoperative issues.

FIG. 1 shows a diagram of a graph 100 that illustrates a conceptual relationship between muscle quality and postoperative issues. Specifically, the graph 100 shows a general relationship between a probability of a patient developing a postoperative complication and muscle density (i.e., radiodensity) measured in Hounsfeld Units ("HU"), which are units of radiation attenuation. The graph 100 is based on a generalization of known studies that have determined a significant correlation between muscle density and a probability of a patient developing a complication. Muscle generally has a radiodensity between 40 HU and 80 HU. Transitional soft tissue, such as transitional epithelium, intramuscular adipose, and/or muscle tissue infiltrated by fat tissue has a radiodensity between −50 HU and 40 HU. By comparison, fat (e.g., visceral adipose tissue and/or subcutaneous adipose tissue) has a radiodensity between −190 HU and −50 HU.

The graph 100 shows that a probability of complications increases as muscle radiodensity decreases. In other words, as muscle tissue (such as the psoas muscle) degrades or becomes infiltrated with fat, the chances of postoperative complications dramatically increase. Further, as tissue radiodensity decreases, the amount of storage available for amino acids decreases. In contrast, muscle tissue with a radiodensity greater than 55 HU (where there is significantly more muscle mass compared to other soft tissue) is associated with relatively low probabilities of a patient developing a complication.

Unfortunately, there are no known methods to objectively quantify amino acid reserves or muscle quality by physical examination alone. As mentioned before, clinicians may perform an eyeball test to gauge a patient's nutritional status. There also exist some preoperative risk stratification tools, such as the American College of Surgeons National Surgical Quality Improvement Program ("ACS NSQIP") surgical calculator. These risk tools help estimate complication rates from various factors. However, the data is estimated based upon information a patient gives to the healthcare provider about prior health history and does not take into account patient-specific measures of vulnerability, frailty, or overall nutritional status.

In contrast to subjective methods, there exist manual time-consuming objective methods to perform a body composition analysis. For instance, researchers can manually select a two-dimensional CT image taken at either the third lumbar vertebra ("L3") and/or the fourth thoracic vertebra ("T4"). These specific skeletal landmarks have been found to correlate well with whole body muscle-to-fat ratios. After selecting the images, researchers painstakingly segment muscle and fat tissue regions using available software products such as, for example, the SliceOmatic™ from TomoVision®. The software requires that a user manually trace a cursor over boundaries of the desired regions, which have fairly complex shapes. While relatively accurate, the manual process takes roughly 10 to 20 minutes per image. Given the urgency of some medical emergencies and the workload of current hospital imaging departments, the lengthy time to determine a patient's body composition usually results in the manual muscle quantification analysis to be skipped or not even considered.

There are also known experimental methods that attempt to automatically segment muscle tissue from fat tissue. These methods attempt to overcome issues in which muscle tissue cannot be distinguished from organ tissue or transitional soft tissue as a result of overlapping radiodensity properties. As mention above, muscle tissue has a radiodensity between 40 and 80 HU while organ tissue has a radiodensity between 30 to 60 HU. The overlap between muscle tissue and organ tissue is due to the inclusion of some muscle tissue within organ tissue. The experimental methods attempt to segment between muscle and organ tissue using statistical shape-matching, shape-deformation, and/or template-deformation to identify surface boundaries of muscle tissue. However, these known methods use shape modeling and assume that muscle shape is consistent among different patients. While the assumption may be accurate for healthy patients, the studies show errors for malnourished patients, where degradation in skeletal muscle mass usually results in asymmetric or random changes in the muscle shape (which can be even more pronounced in a two-dimensional image). The result is that the actual muscular shape for malnourished patients may not match the predefined shapes or templates.

In addition, known studies have focused primarily on segmenting only muscle tissue, such as psoas muscle tissue. The studies did not adequately quantify transitional soft tissue or muscle tissue infiltrated with fat tissue. Transitional soft tissue may be unevenly distributed around muscle tissue, which makes any type of shape-based segmentation difficult, if not impossible. Additionally, muscle tissue infiltrated with fat tissue may be incorrectly identified as pure muscle tissue. Some known studies focused on segmentation between external boundaries of muscle tissue and do not consider situations in which interior portions of the shape may not contain exclusively muscle. The result is that some of the known studies may overestimate muscle quantity in instances in which muscle tissue has significant fat infiltration. Accordingly, these known techniques may be inadequate regarding malnourished or fragile patients that have significant muscle degradation or fat infiltration.

Figure 2:
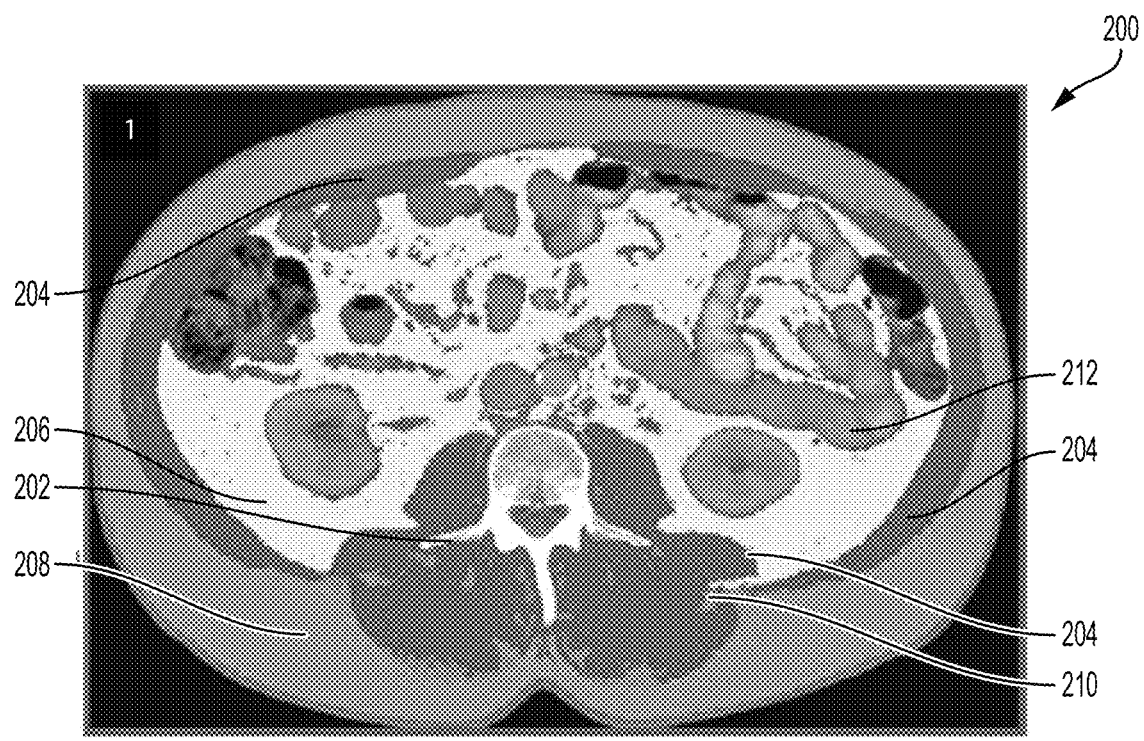
FIGS. 2 and 3 illustrate diagrams of two-dimensional cross-sectional CT images that illustrate muscle degradation in a patient.
Figure 3:

FIGS. 2 and 3 show diagrams of two-dimensional cross-sectional CT images 200 and 300 that illustrate muscle degradation in a patient. The two-dimensional cross-sectional CT images 200 and 300 were recorded at the L3 region of a patient with lung cancer. The image 200 was recorded 390 days before the patient died. In comparison, FIG. 3 was recorded 58 days prior to death. The images 200 and 300 show the patient's backbone 202 at L3 in addition to skeletal psoas muscle 204. The images 200 and 300 also show visceral adipose tissue 206, subcutaneous adipose tissue 208, and intramuscular adipose tissue 210 (muscle infiltrated with fat and/or connective tissue) in addition to internal organs 212, which themselves may include muscle tissue or muscle cells. Between the time image 200 was recorded and image 300 was recorded, the patient experienced a decrease in skeletal muscle from 173 cm$^2$ to 86.7 cm$^2$. During this time, the patient also experienced an increase in the amount of intramuscular adipose tissue 210 and visceral adipose tissue 206.

It should be noted that above-mentioned known studies that use shape or template matching may count the intramuscular adipose tissue 210 as muscle tissue 204 since at least some of the tissue 210 is within the external boundaries of the muscle tissue 204. In other words, the template shapes of solid patterns that assume everything with the boundaries is muscle tissue. The templates do not account for any fat tissue interspaced with muscle tissue. Using the known muscle segmentation methods, the examples illustrated in FIGS. 2 and 3 appear to show minor decreases in muscle area. However, when considering intramuscular adipose tissue 210, the amount of muscle loss is relatively more pronounced.

In addition, while the known studies discuss the quantification of muscle tissue, they are limited in their correlation of an overall nutritional status of a patient. Knowing a patient's muscle quantity is beneficial but it provides little context without additional information. For example, shorter patients may generally have less skeletal muscle than taller patients. In another example, older patients experiencing sarcopenia naturally have less skeletal muscle compared to younger patients. The difference in muscle quantity among different patients means that, absent another metric, the muscle quantity determined by the known studies has to be compared to muscle quantities of similar populations of patients to determine if the patient is nutritionally healthy compared to patients with similar demographic characteristics.

The example system, apparatus, and method disclosed herein attempt to overcome the above-described limitations of known studies by differentiating between intramuscular adipose tissue and muscle tissue (e.g., between the tissue 204 and 210 of FIGS. 2 and 3) to determine muscle quality. In other words, the example system, apparatus, and method not only quantify an amount of muscle in a patient, but also determine a relative muscle quality for that patient. In some instances, the patient's muscle quality may be compared to population data to determine or evaluate a patient's nutritional status relative to known nutritional statuses of patients with similar demographic characteristics. While the quantification and qualification of skeletal muscle is discussed throughout, in some instances, the example system, apparatus, and method may quantify and/or qualify connective skeletal tissue.

As described in more detail below, muscle quality is determined as a relation between muscle tissue and intramuscular adipose tissue. Experimentation has shown that there exists a localized soft tissue peak in a Hounsfield distribution of muscle quantity. The location of the soft tissue peak is related to or indicative of the nutritional status of the patient. For instance, experiments have demonstrated that patients with a muscle mass deficiency have a soft tissue peak that is less than 40 HU (i.e., a peak that is outside the Hounsfield range associated with muscle tissue). By comparison, the experiments have demonstrated that patients with a normal muscle mass have a soft tissue peak that is greater than 40 HU (i.e., a peak that is within the Hounsfield range associated with muscle tissue). The location of the soft tissue peak on the Hounsfield distribution provides an indication of a nutritional status of the patient. In addition, information related to the soft tissue peak, such as peak height, standard deviation from the peak height, skew of the soft tissue peak, a percentage of pixels or soft tissue to the right of the soft tissue peak, a ratio of peak height to muscle height, and/or muscle quantity may provide further information regarding the nutritional status of the patient. As provided below, in some embodiments, the soft tissue peak and related information may also be used to determine or recommend parameters for a nutritional therapy and/or a composition of a nutritional solution.

Certain terms are used throughout this disclosure. As provided herein, nutritional status may refer to an overall nourishment of a patient as determined from a quantity and/or quality of muscle in a specified region. Nutritional status indicates, for example, whether a patient has a normal amount of muscle mass. More generally, nutritional status indicates whether a patient is malnourished, undernourished, starved, or healthy. As disclosed herein, the nutritional status of a patient is used as an indicator as to whether a patient has sufficient amino acid reserves (and/or energy reserves) to undergo an intensive medical procedure without excessive risk of complications thereafter. The nutritional status is based upon or otherwise includes a soft tissue peak value and/or soft tissue peak information. The nutritional status may be specified as a numerical score (e.g., from 0 to 100) or textural descriptor (e.g., malnourished, starved, etc.) based on a soft peak tissue value and/or soft peak tissue information.

Reference is made throughout to soft tissue, soft tissue peak, and soft tissue information. As described below, soft tissue (or transitional tissue) includes intramuscular adipose tissue, connective tissue, and other types of adipose tissue having a radiodensity between −50 HU and 40 HU. Soft tissue generally does not include visceral adipose tissue and subcutaneous adipose tissue, which have radiodensities below −50 HU.

Soft tissue peak may refer to a localized peak within a Hounsfield distribution that illustrates radiodensity of a defined quantity of tissue within a medical image (e.g., a two-dimensional CT scan image). The peak identifies a radiodensity level of a median value of soft tissue including muscle tissue, fat tissue, and intramuscular adipose tissue within a defined area or segmented region of the medical image. In addition, the soft tissue peak is indicative as to whether a majority or significant portion of a patient's soft tissue comprises muscle tissue, intramuscular adipose tissue, or a combination thereof.

Generally, the soft tissue peak is located between −10 HU and 60 HU based on the health of a patient. Muscle tissue has a radiodensity between 40 HU and 80 HU, while intramuscular adipose tissue has a radiodensity between −50 HU and 40 HU. Connective tissue has a radiodensity between 10 HU and 40 HU. Patients that are classified as malnourished, starving, or frail typically have soft tissue peaks between −10 HU and 40 HU, which indicates that a significant portion of the muscle has been infiltrated with intramuscular adipose tissue or there is more connective tissue and adipose tissue compared to muscle tissue. In other words, susceptible patients have less muscle mass or muscle mass that has been replaced by fat (e.g., lower quality muscle), which means that those patients have significantly less amino acid reserves to assist in recovery. In contrast, patients that are classified as nutritionally normal have soft tissue peaks greater than 40 HU, which indicates that the muscle tissue does not contain much, if any, intramuscular adipose tissue. The relatively higher quality muscle typically contains sufficient amino acid reserves to assist in a patient's recovery.

Soft tissue peak information may refer to data or information that is determinable from a soft tissue peak. Generally, a soft tissue peak has a Gaussian-type distribution on a Hounsfield scale. On a typical distribution, a soft tissue peak has a HU value in addition to a muscle (or soft tissue) quantity value (e.g., a number of pixels in a medical image that have a specific HU value and/or an area). The soft tissue peak also has a slope on either side of the peak, which takes into account standard deviations. In some instances, the soft tissue peak may be skewed towards muscle tissue or fat tissue. Certain information can be determined from a soft tissue peak, including a HU value associated with a center or a peak, HU values associated with first and second standard deviations from the peak, and/or muscle or soft tissue quantity associated with the peak, muscle or soft tissue quantity associated with standard deviations of the peak. In addition, soft tissue peak information may include a ratio of the soft tissue peak to values of soft tissue valleys (e.g., fat or thin tails) along the distribution. Further, the soft tissue peak may indicate an amount of skew or muscle reach (e.g., a percentage of soft tissue to the right of the peak).

As provided herein, the soft tissue information may be used in conjunction with the soft tissue peak to determine or evaluate a nutritional status of a patient. The soft tissue information and soft tissue peak may also be used to determine or recommend parameters for a parenteral nutritional therapy and/or contents for a parenteral nutritional solution. For example, a difference between a soft tissue peak and 40 HU may be used to determine an infusion duration or an amount of amino acids to be added to a parenteral nutritional solution. In some embodiments, the example, system, apparatus, and method may use the soft tissue peak and related information to determine that patients identified as being significantly malnourished are to be prescribed parenteral nutritional therapies having greater durations and are to be provided solutions that have 25% to 40% more amino acid or protein content.

The example system, apparatus, and method are described herein as determining a quality and quantity of skeletal muscle. As mentioned above, skeletal muscle typically has a radiodensity between 40 HU and 80 HU. The present disclosure uses the psoas muscles as an example throughout because a cross-sectional area of the psoas muscles (or the thoracic muscles) are generally representative of skeletal muscle quality in other parts of the body. Since amino acid reserves are typically located in skeletal muscle and connective tissue, quantifying psoas skeletal muscle provides an indication of a patient's overall amino acid reserves (and indicate a patient's postsurgical risk). While the present disclosure focuses on the psoas muscle, it should be appreciated that the example system, apparatus, and method may evaluate muscle quality and/or quantity of other skeletal muscles including, for example, triceps muscle, biceps muscle, deltoid muscle, oblique muscle, abdominal muscle, sternum muscle, pectineus muscle, adductor muscle, sartorius muscle, thoracic muscles, etc. It should be further appreciated that the example system, apparatus, and method may evaluate muscle quality and/or quantity for groups of muscles or muscle mass in an entire section of a medical image(s) having validated correlations between patient muscle mass and nutritional status.

It should be appreciated that the example system, apparatus, and method may be used to determine or evaluate risks for many types of medical procedures. For instance, examples below discuss the use of a nutritional status of a patient to determine or evaluate risks for chemotherapy, radiation, and/or traumatic injury treatment. The system, apparatus, and method may also be used for other treatments including pancreatic cancer therapies, prostate cancer therapies, ovarian or breast cancer therapies, organ transplants, hip or joint replacement procedures, gene therapy, blood transfusions, hemodialysis treatments, peritoneal dialysis treatments, etc. Further, the system, apparatus, and method may use a patient's nutritional status to treat patient conditions, such as premature birth, anorexia, malnutrition, or disease. Accordingly, the example system, apparatus, and method disclosed herein may be incorporated into a patient's treatment plan, medical management, and/or medical workflow to manage post-procedural risks and improve the patient's outcome.

Medical Environment Embodiments

Figure 4:
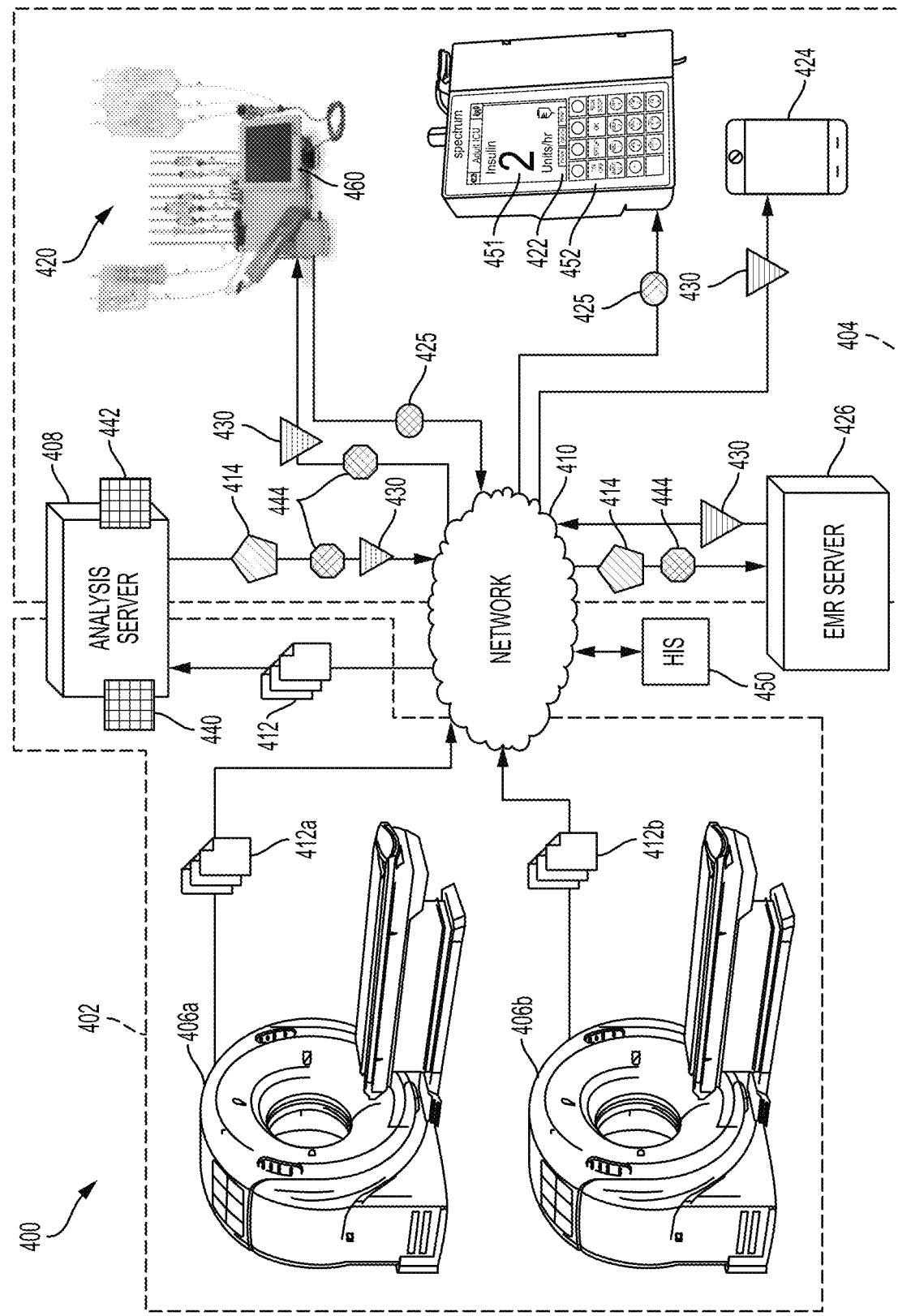
FIGS. 4 and 5 illustrate diagrams of a hospital environment including an analysis server configured to determine a nutritional status of a patient and create/administer a nutritional treatment for the patient based on muscle quality and muscle quantity, according to example embodiments of the present disclosure.

FIG. 4 illustrates one embodiment of a medical environment 400 of the present disclosure configured to determine and/or evaluate a nutritional status of a patient and recommend/create/administer a nutritional treatment for the patient. The example environment 400 includes two primary components: a nutritional status diagnostic component 402 and a nutritional therapy component 404. Both of the components 402 and 404, and more generally, the medical environment 400 may be part of a hospital, a hospital system, a clinic, a doctor's office, an emergency care facility, etc. In some instances, the components 402 and 404 may be physically separated. For instance, the nutritional status component 402 may be located at an imaging center while the nutritional therapy component 404 (or portions of the component 404) is located at a hospital, clinic, or a patient's home.

The example nutritional status diagnostic component 402 is configured to determine and/or evaluate a nutritional status of a patient from one or more medical images. The component 402 includes imaging devices 406a and 406b (referred to herein collectively as imaging device 406 or generally individually as imaging device 406) communicatively coupled to an analysis server 408 via a network 410. While FIG. 4 shows two medical imaging devices 406a and 406b, it should be appreciated that there may be fewer or additional imaging devices.

The imaging devices 406 are configured to transmit medical images 412 to the analysis server 408. The images 412 may include, for example, measured radiodensity data associated with each pixel within the image. The analysis server 408 may be configured to use medical images 412 to determine and/or evaluate a nutritional status of a patient. The nutritional status is transmitted in one or more message(s) 414 from the analysis server 408 to the nutritional therapy component 404. In some instances, the message(s) 414 may be indicative of a soft tissue peak and/or include data related to a determined soft tissue peak including soft tissue peak information.

The example nutritional therapy component 404, in one embodiment, is configured to determine (or recommend) whether a patient is to be provided with a nutritional therapy prior to undergoing another medical procedure based on the nutritional status determined in the nutritional status diagnostic component 402. The nutritional therapy component 404 may also determine parameters for a nutritional pump based, at least in part, on the determined nutritional status of the patient. The parameters may be included within a nutritional therapy pump prescription message 425, which may be electronically transmitted to program a nutritional pump 422. The nutritional status diagnostic component 402 may further determine components of a nutritional solution (or recommend a premixed nutritional solution) based, at least in part, on the determined nutritional status of the patient.

As illustrated in FIG. 4, the nutritional therapy component 404 may include at least one pharmacy preparation system 420 and at least one nutritional infusion pump 422. As provided in more detail below, the pharmacy preparation system 420 is configured to, in one embodiment, among other things, prepare a nutritional solution for administration to a patient. The example infusion pump 422 is configured to administer a nutritional solution (or any other fluid) to a patient. The pharmacy preparation system 420 and the at least one infusion pump 422 are communicatively coupled together via the network 410.

In addition to the pharmacy preparation system 420 and the infusion pump 422, the example nutritional therapy component 404 also includes one or more clinician devices 424 and an electronic medical record ("EMR") server 426. The clinician devices 424 may include any smartphone, tablet computer, workstation (e.g., nurse station computer or bedside computer), laptop computer, server, processor, etc. The clinician devices 424 may also be configured to operate one or more application(s) configured to obtain and display patient data, including a nutritional status of a patient (and any related alerts/alarms) determined by the nutritional status diagnostic component 402 and/or the nutritional therapy component 404. The clinician devices 424 may also include applications that enable nutritional prescriptions to be created and transmitted to the pharmacy preparation system 420.

The example EMR server 426 is configured to store patient medical records, including a nutritional status of a patient determined by the nutritional status diagnostic component 402. In some embodiments, the EMR server 426 is configured to receive and store alarms and/or alerts generated by the analysis server 408 regarding a nutritional status of a patient. In other embodiments, the EMR server 426 uses a received nutritional status of a patient in conjunction with soft tissue peak data and/or related soft tissue peak information to determine one or more alarms/alerts. The EMR server 426 may be configured to transmit alarms/alerts in one or more messages 430, via the network 410, to the clinician device 424 and/or the pharmacy preparation system 420.

In some embodiments, the analysis server 408 is shared logically and/or physically between the nutritional therapy component 404 and the nutritional status diagnostic component 402. In these embodiments, the analysis server 408 may be part of both components 402 and 404. For instance, the analysis server 408 may include a soft tissue engine 440 configured to determine and/or evaluate a nutritional status of a patient and a nutritional analysis engine 442 configured to determine and/or recommend if a patient is to undergo a nutritional therapy and if so, parameters of the therapy and/or components of a solution. In these examples, the nutritional analysis engine 442 determines (or recommends) whether a patient is to undergo a nutritional therapy based on the determined nutritional status. The nutritional analysis engine 442 may also determine and/or recommend parameters of the therapy and/or components of a nutritional solution, which are transmitted in one or more message(s) 444 to the pharmacy preparation system 420. The parameters of the therapy may be incorporated by the pharmacy preparation system 420 into the nutritional therapy pump prescription message 425. Additionally, the pharmacy preparation system 420 may prepare a nutritional solution based on components or therapy parameters provided by the nutritional analysis engine 442.

Figure 5:
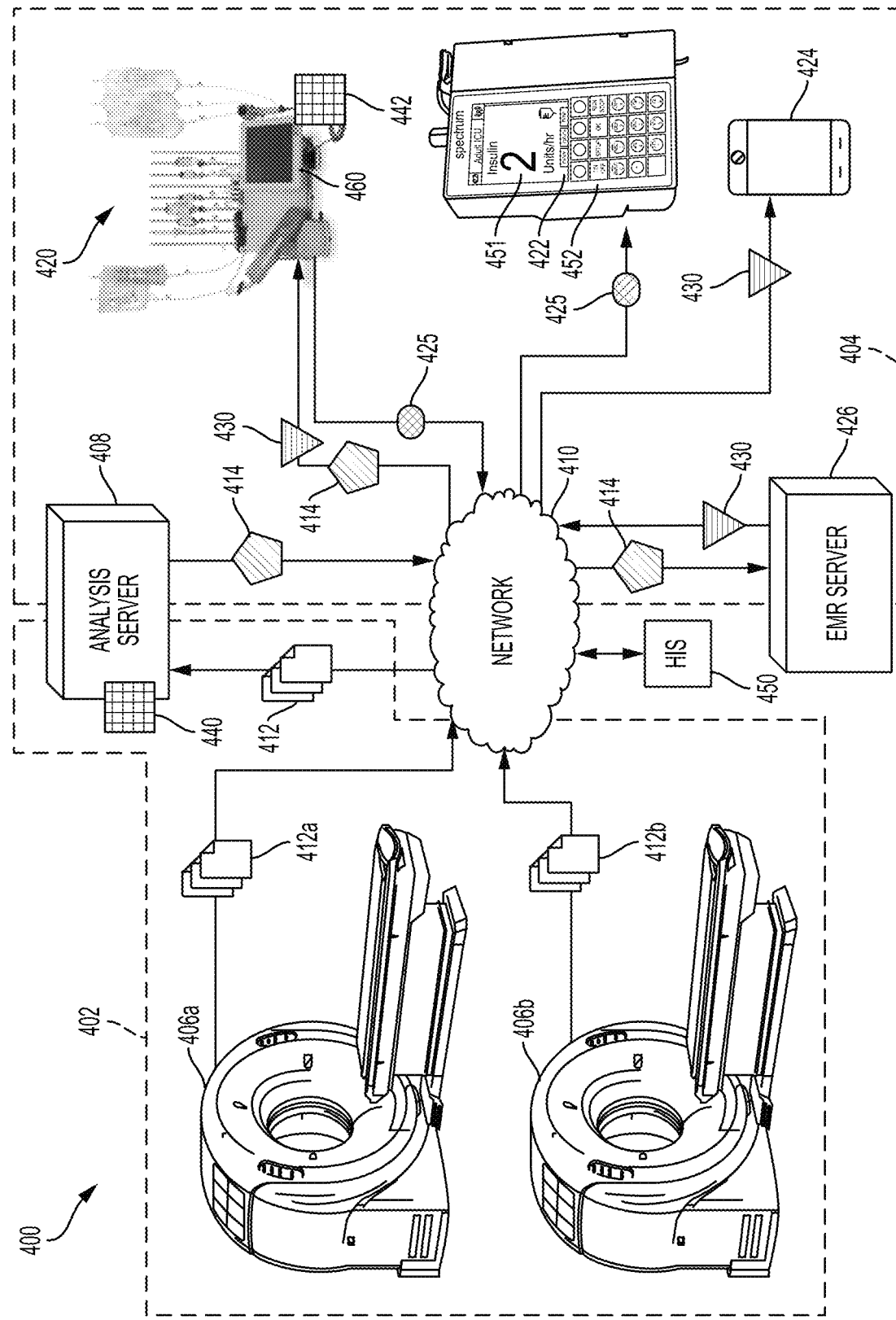

FIG. 5 shows an alternative embodiment of the medical environment 400 of FIG. 4. In FIG. 5, the analysis server 408 is configured to include only the soft tissue engine 440, according to an example embodiment of the present disclosure. In this alternative embodiment, the nutritional analysis engine 442 is configured, or otherwise provided within a pharmacy computer 460 of the pharmacy preparation system 420. The placement of the nutritional analysis engine 442 means that nutritional parameters are determined at the pharmacy preparation system 420 rather than the analysis server 408. Similar to the environment 400 of FIG. 4, the analysis server 408 is configured to provide the nutritional status of the patient (and/or soft tissue peak information) in one or more message(s) 414. However, in the environment 400 of FIG. 5, the pharmacy preparation system 420 uses the information in the messages 414 to determine pump parameters and/or components of a nutritional solution.

In yet alternative embodiments, the nutritional analysis engine 442 may be included within the EMR server 426. In these instances, the analysis server 408 is configured to provide the nutritional status of the patient (and/or soft tissue peak information) in one or more message(s) 414 to the EMR server 426. After receiving the data, the nutritional analysis engine 442 at the EMR server 426 determines if and/or evaluates whether a patient is a candidate to undergo a nutritional therapy and if so, determine and/or recommend appropriate pump parameters and/or solution components. The EMR server 426 then provides the pump or solution information to the pharmacy preparation system 420 to program the pump 422 and prepare the solution. In some instances, the EMR server 426 may transmit the parameters directly to the pump 422 (after receiving approval from the clinician device 424 or the pharmacy preparation system 420), thereby bypassing transmission of the nutritional therapy pump prescription message 425 through the pharmacy preparation system 420. Transmission of the parameters may include the EMR server 426 being configured to create the nutritional therapy pump prescription message 425 for transmission to the pump 422.

The medical environments 400 of FIGS. 4 and 5 also include a hospital information system ("HIS") 450. The example HIS 450 is configured to manage the aspects of a hospital's operation, such as medical, administrative, financial, and legal issues, and the processing of services. The HIS 450 may manage or create secure tunnels or paths to communicate sensitive medical data in instances in which at least some portions of the components 402 and 404 are external to a local hospital network. For example, the HIS 450 may create a virtual private network to enable external clinician devices 424 to view patient data stored at the EMR server 426. The HIS 450 may also facilitate the exchange of patient data stored in medical records with the various departments or functional areas of the medical environment 400.

The network 410 illustrated in FIGS. 4 and 5 may include a wide area network ("WAN") such as the Internet. The network 410 may also include a local area network ("LAN") and/or a wireless LAN. In some embodiments, the network 410 may include a combination of a WAN and LAN. Further, the network 410 may include one or more firewalls, gateways, routers, switches, etc., for routing communications among the devices 406, 408, 420, 422, 424, and 426. The network 410 may also be configured to enable the HIS 450 to create secure connections to enable devices external to a secure medical network to receive and transmit messages with devices within the secure medical network.

I. Nutritional Status Diagnostic Component Embodiment

As discussed above, the medical environments 400 of FIGS. 4 and 5 include the nutritional status component 402 to determine and/or evaluate a nutritional status of a patient from one or more medical images 412. As described below, the nutritional status component 402, including the soft tissue engine 440, is configured to generate a measurement or characterization of total lean body mass, referred to herein as the nutritional status of a patient. To determine a patient's nutritional status, the nutritional status component 402 may determine and/or evaluate a quality and quantity of a patient' muscle tissue. In many embodiments, the nutritional status component 402 determines a quality and quantity of skeletal muscle (e.g., the psoas muscle), which provides an indicator of total body protein or amino acid stores. Given the relation of amino acid stores in the body to postoperative success rates and complications (as shown in the graph 100 of FIG. 1), the measurement of a patient's nutritional status provides an objective indicator of postoperative risk. The nutritional status indication may be used by the nutritional therapy component 404 to determine and/or recommend at least one nutritional therapy to increase amino acid availability and improve a patient's postoperative outcome. The following section provides information regarding how a patient's nutritional status is determined and/or evaluated using at least one medical image 412 according to the present disclosure.

The example imaging devices 406 are configured to acquire at least one medical image 412 of a patient. The at least one image 412 is used by the soft tissue engine 440 of the analysis server 408 to determine and/or evaluate a nutritional status of the patient. The imaging, and hence the determination of nutritional status, may occur before a patient is to undergo a medical procedure, such as chemotherapy. In some instances, the imaging may occur when a patient is brought into a hospital or clinic after experiencing a traumatic injury or after developing a serious disease.

In some embodiments, the imaging devices 406 are CT scanners, such as the Iqon Spectral™ or Ingenuity Flex™ CT scanners manufactured by Phillips® or the Revolution™, Optima™, or BrightSpeed™ CT scanners manufactured by the General Electric Company®. In these instances, the imaging devices 406 are configured to take combinations of X-ray images from one or more angle(s) to produce cross-sectional (e.g., tomographic) images or virtual slices of a patient's anatomy. The images 412 are recorded of a specific portion of a patient's anatomy, such as a thorax region, abdomen region, a pelvic region, etc. The cross-sectional images 412 may be lateral or axial, showing patient anatomy at different north-south elevations. The cross-sectional images 412 may alternatively or additionally be longitudinal, showing patient anatomy at different east-west sections.

While the imaging devices 406 are referred to herein as X-ray-type CT scanners, it should be appreciated that other medical imaging devices may be used. For example, the imaging devices 406 may include positron emission tomography ("PET") scanners, single-photon emission computed tomography ("SPECT") scanners, computed axial tomography ("CAT") scanners, and computer-aided/assisted tomography scanners. In some instances, the imaging devices 406 may include magnetic resonance imaging ("MRI") scanners.

The imaging devices 406 may additionally or alternatively be configured to perform radiodensity measurements on a patient's tissue using contrast (e.g., an intravenously injected radiocontrast agent) or without contrast. In some instances, the medical images 412 provided to the soft tissue engine 440 may include a combination of contrast and non-contrast images. In these examples, the imaging device 406 may determine and/or evaluate a patient's nutritional status using contrast and non-contrast medical images 412 of the same area. In these examples, the soft tissue peak data and soft tissue information determined from the contrast and non-contrast images may be averaged or otherwise combined.

Each of the example medical images 412 shows a radiodensity level of patient tissue. The medical images 412 may comprise a two-dimensional cross-sectional slice (such as the images 200 and 300 of FIGS. 2 and 3). Each image 412 may have a size between 256×256 pixels to 2040×2040 pixels, for example. Preferably, each two-dimensional image may have 512×512 pixels with two bytes of color data per pixel. Accordingly, each two-dimensional image 412 may contain about 3.3 gigabytes ("GB") of radiodensity data. Each pixel of the medical images 412 may be color coded by radiodensity level. Further, the medical image 412 may include metadata that specifies a radiodensity level for each pixel. The metadata may also identify the patient, a time/date that the scan was performed, and an identifier of the imaging device 406 that performed the scan.

Each of the medical images 412 may be stored in a file. For instance, each medical image 412 may be stored as a Digital Imaging and Communications in Medicine ("DICOM") image. In these instances, the metadata specifying the radiodensity values may be stored within a header of the file, while the image information is stored within a payload section of the file. In other embodiments, the medical image 412 may include another file type, such as a Neuroimaging Informatics Technology Initiative ("NIfTI") file, a Minc file, and/or an Analyze file.

The imaging devices 406 may be configured to record between about 50 to about 150 images per scan of a patient. Scans of the abdominal region generally yield about 75 images. However, the exact number of images is set by technicians operating the imaging devices 406. In some instances, one or only a few images may be required since the nutritional status analysis may be conducted on a single image of, for example, the psoas muscle in the L3 or L4 region. Reducing the number of images recorded reduces a patient's radiation exposure.

Figure 6:
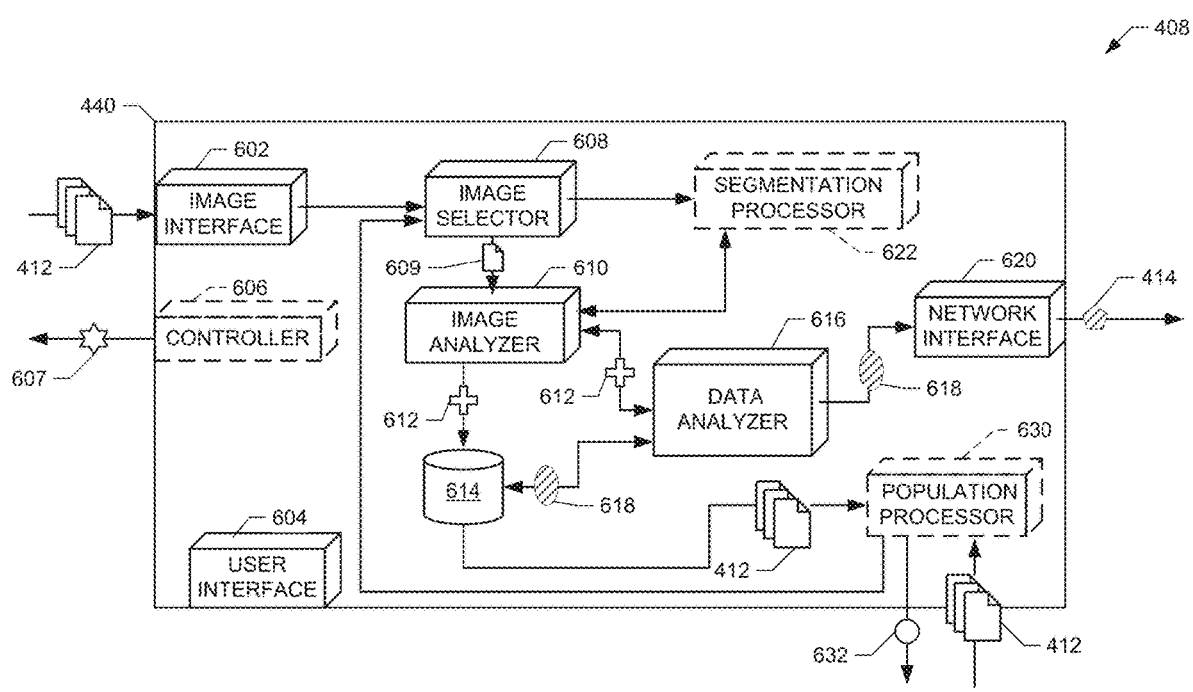
FIG. 6 illustrates a diagram of a soft tissue engine included within the analysis server of FIGS. 4 and 5, according to an example embodiment of the present disclosure.

The example soft tissue engine 440 is configured to analyze the medical images 412 to determine and/or evaluate muscle quality and/or quantity for approximating a nutritional status of a patient. FIG. 6 shows a diagram of the soft tissue engine 440 of FIGS. 4 and 5, according to an example embodiment of the present disclosure. The blocks shown in FIG. 6 may be implemented as software modules, applications, algorithms, and/or routines operating within the soft tissue engine 440. It should be appreciated that some of the blocks may be combined and/or omitted, such as segmentation processor 622. Further, some of the blocks may be implemented in different physical locations on the analysis server 408. For instance, the analysis server 408 may include blade servers or processors distributed across a computing environment such as a cloud computing environment. Each of the blocks illustrated in FIG. 6 may accordingly be hosted or implemented in different physical and/or virtual locations within a distributed environment. Each of the blocks shown in FIG. 6 may therefore be implemented or operated by separate (or the same) processors. Moreover, separate instances of each of the blocks may be initiated for each set of images 412 analyzed.

a. Image Interface

To receive medical images 412 from the imaging devices 406, the example soft tissue engine 440 of FIG. 6 includes an image interface 602. The example image interface 602 may be configured to passively receive the medical images 412 from the imaging devices 406. For instance, after a scan has been completed, the imaging device 406 transmits the medical images 412 to the image interface 602. Alternatively, the image interface 602 may periodically poll the imaging device 406 to determine if new images are available. In some instances, the imaging device 406 may transmit the medical images 412 to a workstation. In these instances, an operator reviews the medical images to confirm they are visually clear and that a patient did not move during the scan. After the images 412 are indicated as being acceptable, the workstation transmits the images to the image interface 602.

The image interface 602 is configured in one embodiment to queue medical images 412 until they are to be analyzed and/or processed. The image interface 602 may provide status information to a user interface 604. The status may include an indication as to which medical images 412 are awaiting analysis, scheduled to be analyzed, and/or are in the process of being analyzed. For example, a technician may view a status of the medical images 412 through the user interface 604.

b. User Interface

The example user interface 604 is configured to provide administrative access and control to process and analyze the medical images 412. The user interface 604 may be configured to render requested information into a format for display. Such information can include a status of medical images 412, soft tissue peak information, Hounsfield distribution data, image segmentation information, and/or image radiodensity information. The user interface 604 may also include a viewer configured to render the medical images 412 for display. The user interface 604 may also include features that enable a technical to manually process and analyze an image to determine muscle quality and/or quantity. However, while the user interface 604 enables a manual processing, it should be appreciated that the features of the soft tissue engine 440 described herein are completed without user intervention.

In some embodiments, the clinician device 424 may access the user interface 604 to view the medical images 412 and target medical images 609. In addition, the clinician device 424 may access the user interface 604 to view muscle quality and/or quantity data (and/or a nutritional status of a patient) determined from the medical images. In these examples, the user interface 604 may present a list of patients for selection. Upon receiving a selection from the clinician device, the user interface 604 may determine which images and/or data is available within the soft tissue engine 440. A clinician may view the images and/or data on the clinician device 424. Further, the user interface 604 may interact with the clinician device 424 to enable a clinician to modify, amend, and/or make notes to the images and/or data.

c. Controller

The example soft tissue engine 440 of FIG. 6 includes a controller 606 configured to provide instructions to the imaging devices 406. In some instances, only a single medical image (or a few medical images) is needed to determine a patient's nutritional status. Instead of subjecting the patient to x-rays to acquire approximately 100 images and selecting the desired image, the example controller 606 instructs the imaging devices 406 as to which specific location on a patient is needed for imaging. Such a configuration reduces the amount of radiation to which a patient is exposed.

In an example, the soft tissue engine 440 may receive, via the user interface 604 for example, an indication of a specific patient that is to undergo a CT scan to determine a nutritional status of a patient. The controller 606 determines a specific region on the patient where the CT scan is to be completed. The specific region may include, for example a scan of the patient's psoas muscle between the L3 and L4 vertebra. The controller 606 may also receive an indication as to which imaging device 406 is to image the patient. For instance, an identifier of the imaging device may be input into the user interface 604. Alternatively, the controller 606 may access the patient's medical record stored in a database accessible by the EMR server 426. After determining which imaging device 406 is to image a patient, the controller 606 transmits a message 607 to the imaging device 406 indicative of the region on the patient to be imaged.

In some examples, the controller 606 may be omitted or not used. For example, in many instances, patients are given a CT scan as a standard practice upon entering an emergency care area or before a significant medical procedure. In these circumstances, an entire region of interest is scanned for medical diagnosis. Here, the image interface 602 receives a copy of the medical images 412. In this manner, a separate CT scan does not need to be completed to determine a nutritional status of a patient. Instead, medical images already acquired for other purposes may be used to determine the patient's nutritional status.

d. Image Selector

The soft tissue engine 440 includes an image selector 608 for instances in which more than one medical image 412 is received in the image interface 602. Here, the image selector 608 determines or identifies a target medical image 609 for further analysis. Specifically, the image selector 608 may be configured to analyze multiple medical images 412 to determine which medical image contains sufficient patient anatomy to determine skeletal muscle quality and/or quantity. For example, the image selector 608 may identify a medical image that includes the psoas muscle or the thoracic muscle.

The example image selector 608 determines a target image 609 by identifying locations and quantities of bone tissue. For instance, the image selector 608 may identify locations of rib and hip bone tissue to determine a location between the L3 and L4 vertebra. In some embodiments, the image selector 608 is configured to identify within each two-dimensional image pixels that correspond to a radiodensity above 300 HU, which is the radiodensity associated with bone tissue. Counting pixels with a radiodensity above 300 HU provides a relatively precise estimation of bone tissue surface or cross-sectional area per each two-dimensional medical image.

Figure 7:
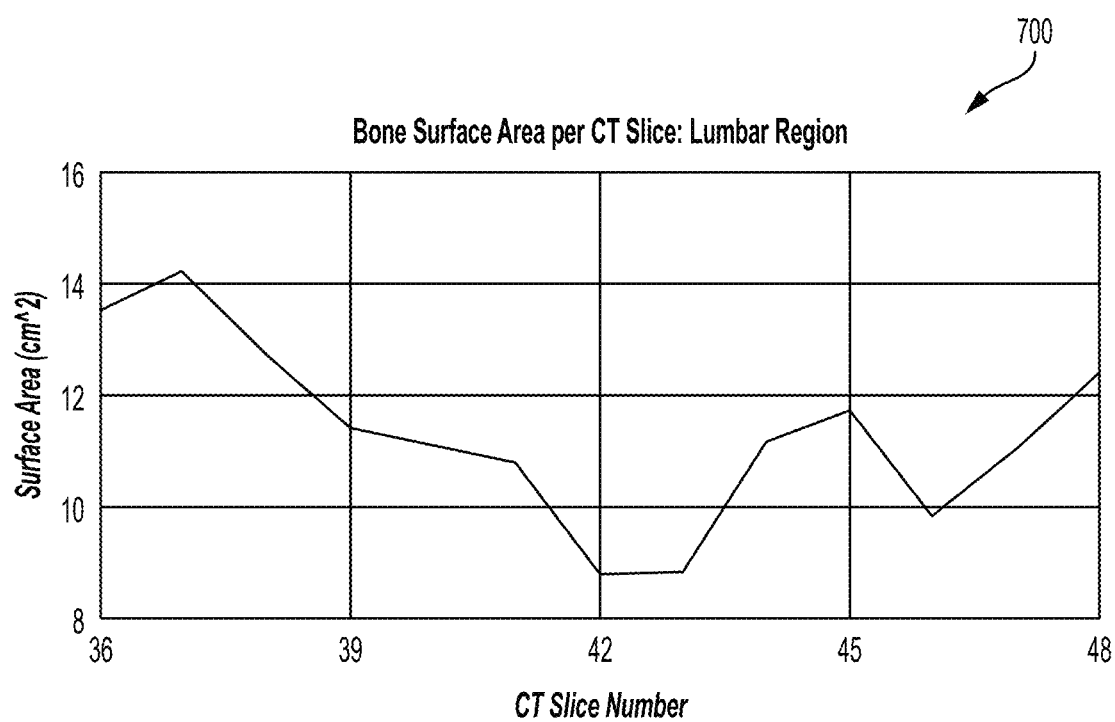
FIG. 7 illustrates a graph that illustrates bone surface area in square centimeters in a patient's lumbar region for determining a medical image to analyze for muscle quality and muscle quantity, according to an example embodiment of the present disclosure.

FIG. 7 shows a graph 700 that illustrates bone surface or cross-sectional area in square centimeters ("cm$^2$") for a patient's lumbar region. The surface or cross-sectional area in centimeters may be determined by summing the total number of pixels, where each pixel has a known surface area in centimeters. The graph 700 shows that it is limited to medical images 36 (left end) to 48 (right end) in a set of medical images that ranges from, for example, 1 to 80. In the example graph 700, images 36 and 37 include the L3 vertebra and the last floating rib, which corresponds to a larger bone surface area of around 14 cm$^2$. Images 42 and 43 include an area between the L3 and L4 vertebras, which include less bone surface area of around 9 cm$^2$. Images 44 to 46 include the L4 vertebra, which shows an increase in bone surface area to about 11 cm$^2$. Image 48 includes a top of the pelvic wing, which is usually coplanar with the L4 vertebra. The inclusion of the pelvic wing causes the bone surface area to increase to above 12 cm$^2$.

The example image selector 608, in the example of FIG. 7, is configured to progress through the medical images 412 to determine the lumbar region between the L3 and L4 vertebras. The image selector 608 then determines a bone surface or cross-sectional area by counting a number of pixels in each of the medical images 36 to 48 that have a radiodensity greater than 300 HU. The image selector 608 identifies, as the target medical image, the medical image that has a lowest bone tissue surface area in the lumbar region. In other words, the image selector 608 determines which of the medical images represented in graph 700 has a minimum tissue surface area.

The example image selector 608 is configured to identify the lumbar region based on the relation between the medical images. For example, the image selector 608 may be configured to analyze medical images numbered 25 to 45 for any CT scan of a patient's mid-section, which generally correspond to the lumbar region for virtually all patients. In other examples, the image selector 608 is configured to identify the pelvic wing tip and/or last floating rib, which are relatively easy to identify within a set of medical images of a patient's midsection. For instance, the image selector 608 may search certain anatomical areas in a sequence of images 412 (corresponding to locations of the wing tips) to determine which images have radiodensity values around 300 HU in those areas. Once the pelvic wing tip is identified, the image selector 608 identifies the previous 10 to 15 medical images, or approximately 7.5 cm up from the pelvic wing tip, to determine which medical images are to be analyzed for bone surface or cross-sectional area.

In some examples, the image selector 608 may segment or otherwise identify a specified portion of each medical image to identify a target medical image. In these examples, the image selector 608 determines a center of mass in the patient's lumbar region. For instance, the image selector 608 may select any medical image numbered 25 to 50, which generally correspond to the lumbar region for most (if not all) patients. The image selector 608, for the selected image, determines a center of mass by determining a center, or approximate center within the patient's anatomy shown within the selected medical image.

Figure 8:
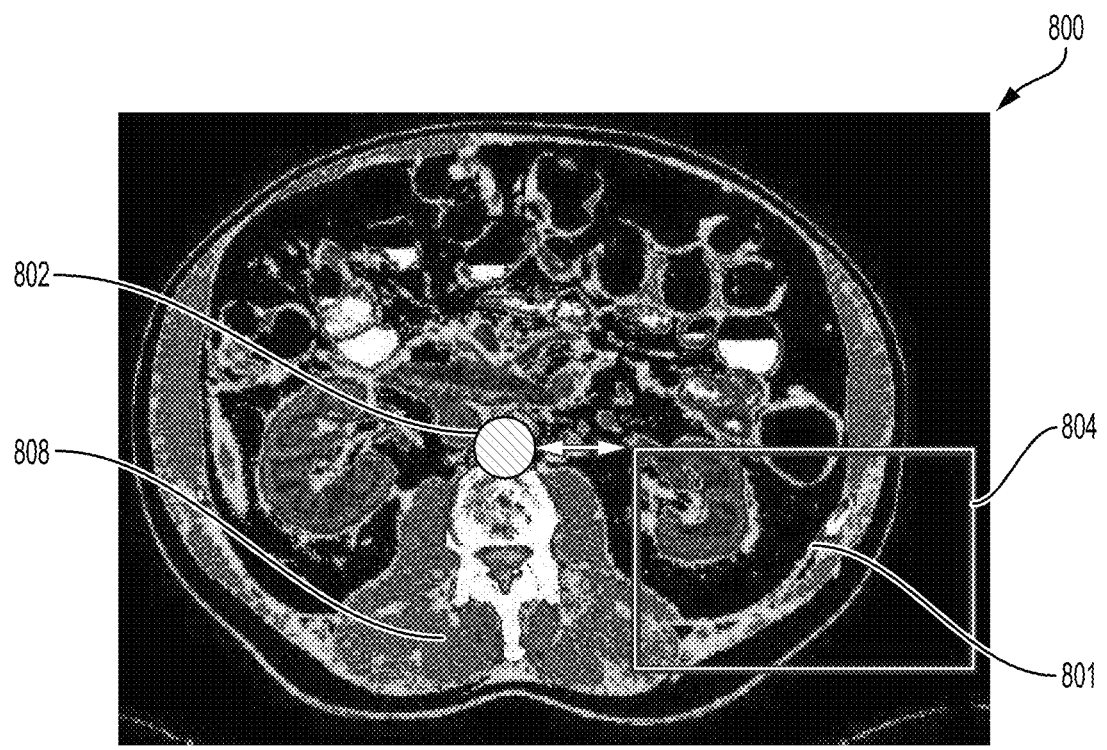
FIGS. 8 and 9 illustrate center-of-masses within medical images that were determined by the soft tissue engine of FIG. 6, accordingly to example embodiments of the present disclosure.
Figure 9:
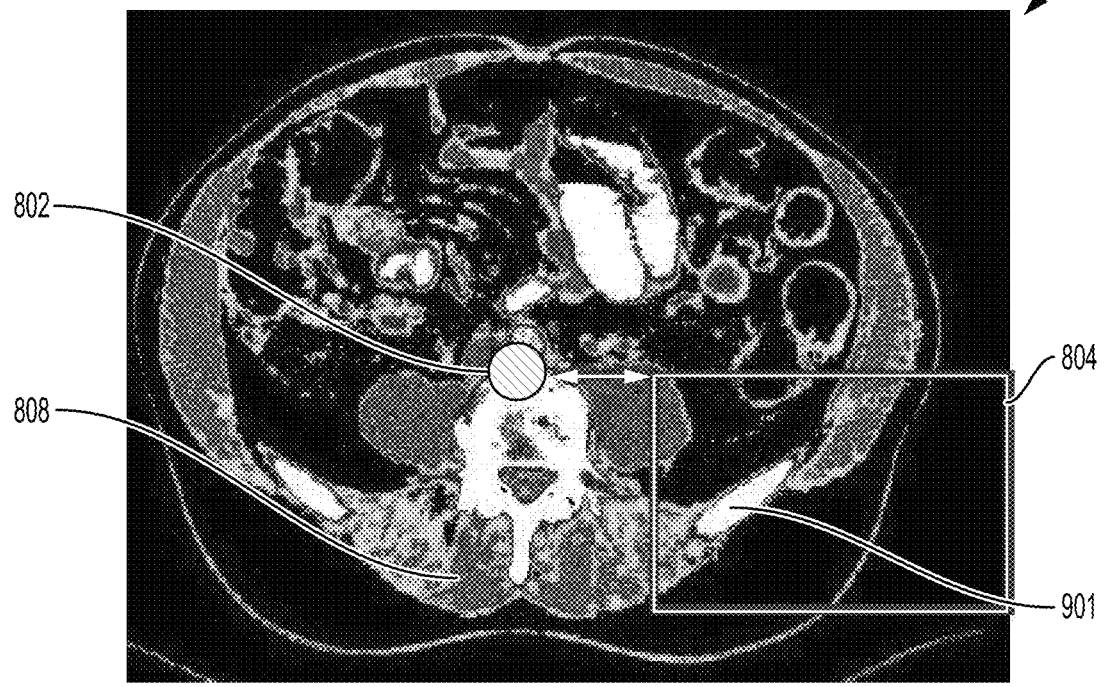

For example, medical images 800 and 900 respectively of FIGS. 8 and 9 show a determined center-of-mass 802 (or center-of gravity), accordingly to example embodiments of the present disclosure. The center-of-mass 802 may be determined for one medical image, such as image 800 and then applied to subsequent medical images, such as the medical image 900. In other examples, the image selector 608 is configured to determine a center-of-mass for each image. The medical images 800 and 900 are of the same patient at two different cross-sectional slices. The medical image 800 of FIG. 8 shows an end of a last floating rib 801. By comparison, medical image 900 of FIG. 9 shows the emergence of the pelvic wing 901.

The image selector 608 uses the center-of-mass 802 in FIGS. 8 and 9 as a point of reference. The image selector 608 creates a polygonal region 804 that has a top-left corner located at a defined distance horizontally offset outwardly from the center-of-mass 802. The defined distance may be between one cm and eight cm. In some instances, the image selector 608 may determine the defined distance based on a height of the patient, where a greater distance is selected for larger patients. The purpose of the offset is to exclude the backbone and vertebra from the bone surface or cross-sectional area analysis.

The polygonal region 804 of FIGS. 8 and 9 may be sized to encompass the right-side ribs and pelvic wing of the patient. As mentioned above, the medical image 800 of FIG. 8 shows an end of a last floating rib 806, while the medical image 900 of FIG. 9 shows the emergence of the pelvic wing 902. Medical images in numerical order between medical images 800 and 900 should contain no bone tissue within the polygonal region 804 because there is generally no bone (other than the vertebra) located between the last floating rib 806 and the top of the pelvic wing 902 in this region.

The image selector 608 is configured to apply the same polygonal region 804 to the medical images associated with the lumbar region (e.g., medical images of slices between the L3 and L4 vertebras). The image selector 608 then determines tissue radiodensity for the pixels within the polygonal region 804. Medical images that contain substantially no bone tissue (e.g., images with substantially no radiodensities above 300 HU in the polygonal region 804) correspond to images that may be selected for further analysis (e.g., target medical images). Since the psoas muscle 808 naturally decreases in size further down the backbone (as shown in medical images 800 and 900), the image selector 608 is configured to select the medical image with the highest sequence number that does not contain bone tissue within the polygonal region 804 (e.g., the medical image right after the last floating rib).

After identifying the target medical image 609, the image selector 608 is configured to provide or transmit the image automatically for further processing. In some instances, the entire medical image may be analyzed to determine muscle quality and quantity. In other instances, only a specified portion of the medical image is analyzed to determine muscle quality and quantity. While the image selector 608 is disclosed above as selecting one target image 609, it should be appreciated that the image selector 608 may select multiple images for analysis. For instance, the image selector 608 may provide multiple images between the L3 and L4 vertebras. Further, the image selector 608 may provide a non-contrast medical image and a contrast medical image.

In some instances, the image selector 608 may transmit a message to the user interface 604 that is indicative of the selected target image(s) 609. The user interface 604 may display a message to a technician including the identified image(s) 609. The technician may then review the medical image(s) 609 to determine if the images are acceptable for determining muscle quality and/or quantity. After receiving an indication of approval from the user interface 604, the image selector 608 transmits the medical image for further analysis. If a disapproval indication is received (in instances where a technician may desire a different image or find fault with the selected image), the image selector 608 may select another image using the methods described above, in which the disapproved image is removed from consideration. Additionally or alternatively, the image selector 608 may provide a small subset of medical images for the technician to choose from to determine muscle quality and/or quantity.

e. Image Analyzer

The example soft tissue engine 440 of FIG. 6 includes an image analyzer 610 configured to determine a distribution of radiodensity for the tissue shown within the pixels of the target medical image 609 provided by the image selector 608. The example image analyzer 610 is also configured to determine muscle and/or tissue quantity provided within the target medical image 609 by analyzing the pixel data within the image and/or the radiodensity data within the metadata. The image analyzer 610 is configured to generate a distribution of radiodensity density at different levels or bins to enable muscle quality to be determined.

Figure 10:
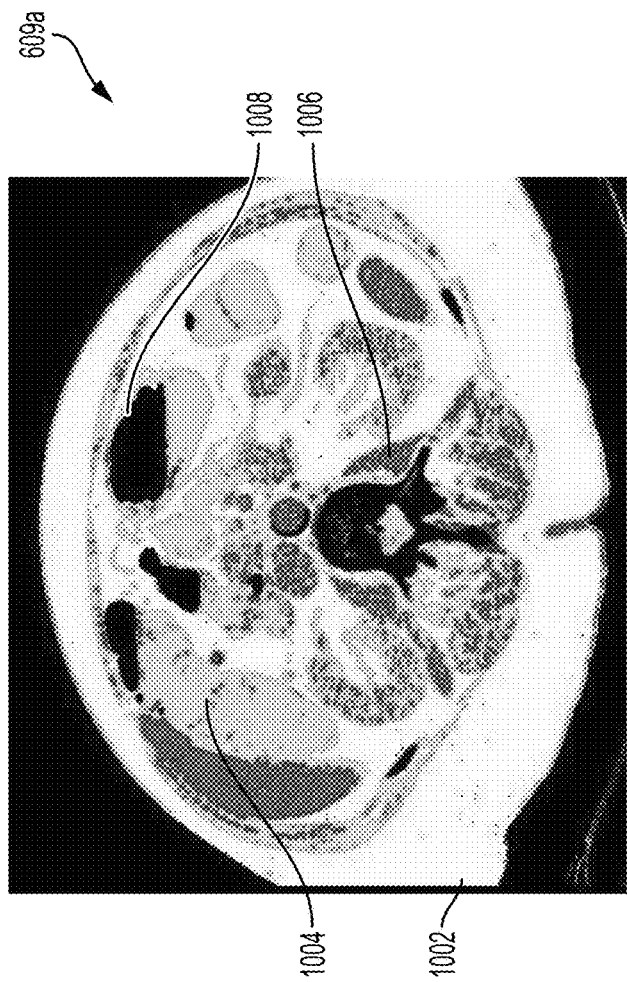
FIGS. 10 and 13 illustrate diagrams of target medical images that may be analyzed by the soft tissue engine of FIG. 6 to determine muscle tissue quantity, accordingly to example embodiments of the present disclosure.

FIG. 10 shows a diagram of a target medical image 609a that may be analyzed by the image analyzer 610 to determine tissue quantity. The target medical image 609a includes pixels that are color-coded based on a radiodensity value detected in the corresponding region of the patient. The target medical image 609a counts a total number of pixels that have the same radiodensity value or level. The image analyzer 610 may then convert the pixel count to surface or cross-sectional area in squared centimeters based on known dimensions of each pixel. The image analyzer 610 then creates a distribution of the of the total tissue surface area for each radiodensity value or level. A 512×512 pixel medical image has approximately 262,000 pixels of data, which provides sufficient resolution to adequately determine tissue quantity.

Figure 11:
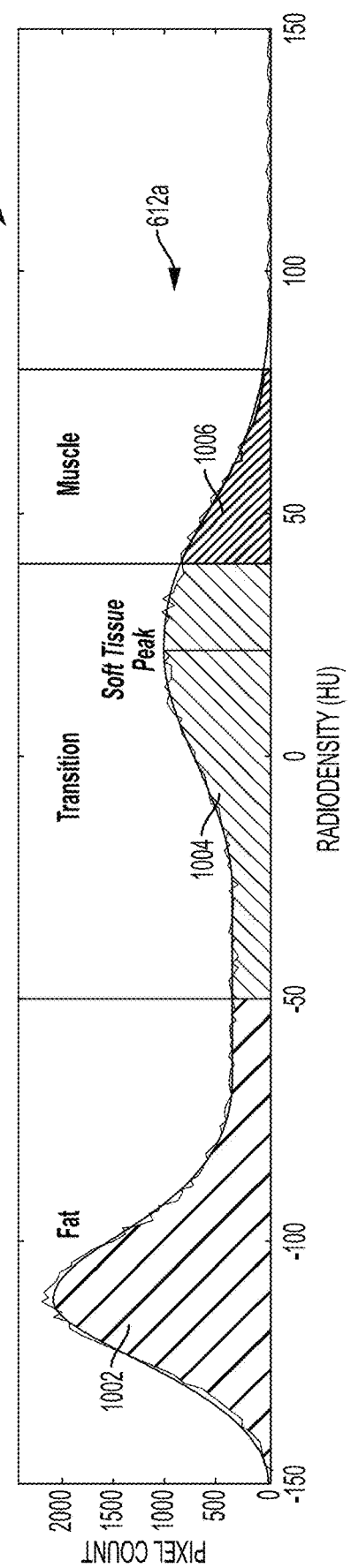
FIGS. 11 and 14 illustrate diagrams of distribution graphs that show total tissue pixel counts for each radiodensity value in HU from the respective target medical images of FIGS. 10 and 13, according to example embodiments of the present disclosure.

FIG. 11 shows a diagram of a distribution graph 1100 (e.g., a soft tissue nutritional histogram ("nutrition-gram") illustrating total tissue pixel counts for each radiodensity value in HU from the target medical image 609a of FIG. 10, according to an example embodiment of the present disclosure. The distribution graph or nutrition-gram 1100 may accordingly be referred to as a Hounsfield distribution or data distribution 612a. It should be appreciated that in other embodiments, the surface or cross-sectional area may be represented in squared centimeters. The nutrition-gram 1100 may only be illustrative of a distribution created by the image analyzer 610. For example, during use, the image analyzer 610 may compute a distribution for each radiodensity level that comprises a series of numbers stored in a file or database. Each row may represent a different radiodensity value and include a number of corresponding pixels and/or computed surface area.

In the example discussed in connection with FIGS. 10 and 11, the image analyzer 610 identifies pixels that have a radiodensity value within a specified range, such as for example, −150 HU to 150 HU. This example range encompasses all muscle and fat tissue. This range, however, excludes bone tissue and some organ tissue, which is shown in FIG. 10 as dark pixels 1008. Limiting the analysis to a certain radiodensity range reduces the amount of pixels that need to be analyzed or counted without affecting the results.

In the example discussed in connection with FIGS. 10 and 11, the color-coding of the pixels has been simplified for readability where designated region 1002 corresponds to fat tissue (i.e., visceral adipose tissue and subcutaneous adipose tissue), designated region 1004 corresponds to transitional tissue (i.e., intramuscular adipose tissue), and designated region 1006 corresponds to muscle tissue. It should be appreciated, however, that in many embodiments, the shading or coloring of the pixels may be as complex as 2 bytes.

In some embodiments, the image analyzer 610 is configured to use binning to create the distribution 612a illustrated in the nutrition-gram 1100 of FIG. 11. For example, the image analyzer 610 may create radiodensity bins that have a width between 0.1 HU to 2 HU. The image analyzer 610 determines which radiodensity values fall within each bin. The image analyzer 610 then counts the number of pixels in each bin to create the distribution.

In some embodiments, the image analyzer 610 is configured to use one or more filter(s) to smooth the distribution data 612a. For example, the image analyzer 610 may be configured to apply a Savitzky-Golay digital filter to smooth the data 612a of the nutrition-gram 1100. In other instances the image analyzer 610 may use a moving-average filter, a multipass filter, or other type of convolution filter. The smoothing of the distribution data enables the data to be more easily analyzed to search for localized peaks, such as a soft tissue peak. Without data smoothing, there is a high frequency of miniature peaks that make searching for a larger local peak more difficult. The filter accordingly removes a noise-element from the data to enable more efficient downstream data processing. The use of the filter also increases the probability of identifying the soft tissue peak.

Figure 12:
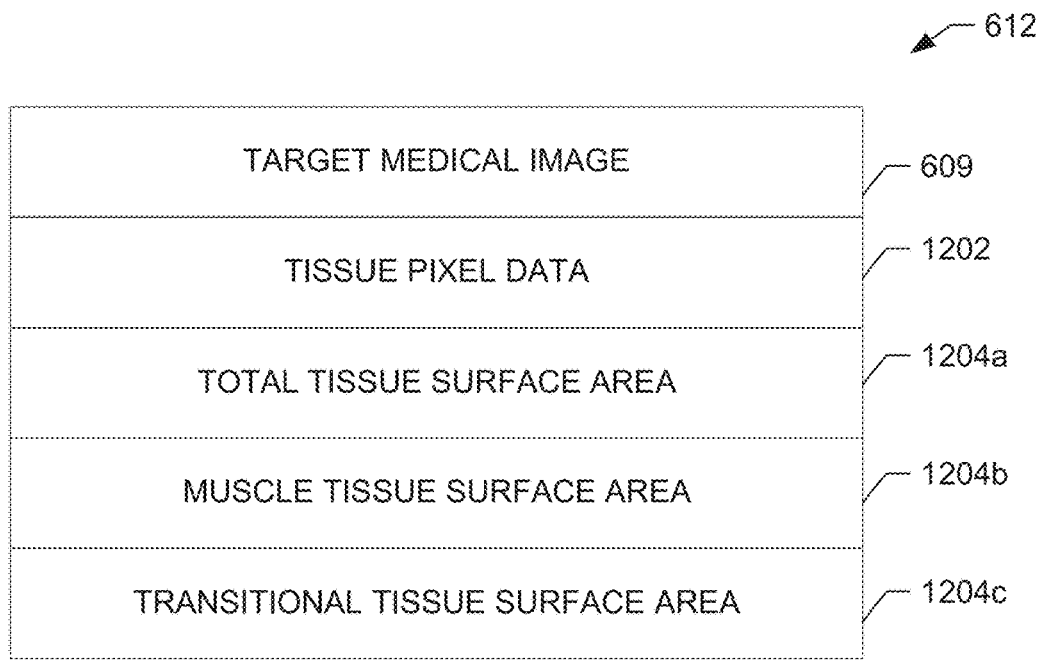
FIG. 12 illustrates a diagram representative of muscle quality and/or quantity data that may be determined, stored, and transmitted by the soft tissue engine of FIG. 6 based on the distribution graphs of FIGS. 11 and 14, according to an example embodiment of the present disclosure.

The example image analyzer 610 is configured to output certain distribution data 612 for further processing to determine, for example, a soft tissue peak and related information. FIG. 12 shows a diagram illustrative of muscle quality and/or quantity distribution data 612 that may be determined, stored, and transmitted by the image analyzer 610. The distribution data 612 may be stored in one or more files to memory 614. For example, the target medical image 609 may be stored in a first file, while tissue pixel data 1202 and surface area data 1204 are stored in a second file. In some instances, the second file storing the tissue pixel data 1202 and surface area data 1204 may include a link or reference to the target medical image 609 stored in the first file. Distribution data 612 that may be determined by the image analyzer 610 includes, for example, tissue pixel data 1202 for all tissue types in the target medical image 609 (or all tissue within a specified range), a total tissue surface area 1204a, a muscle surface area 1204b, and/or a transitional tissue surface area 1204c. The surface area may be expressed as a pixel count or squared centimeters. Further, the data 612 may be binned and/or stored within a distribution graph, such as nutrition-gram 1100.

The example user interface 604 is configured to make the distribution data 612 available for display. For instance, the user interface 604 may display the nutrition-gram 1100 in conjunction with the medical image 609*a*. Further, the surface area data 1204 may be displayed in specified fields. Such information enables a technician to view the analyzed data as it is being processed or after it has been processed.

Figure 13:
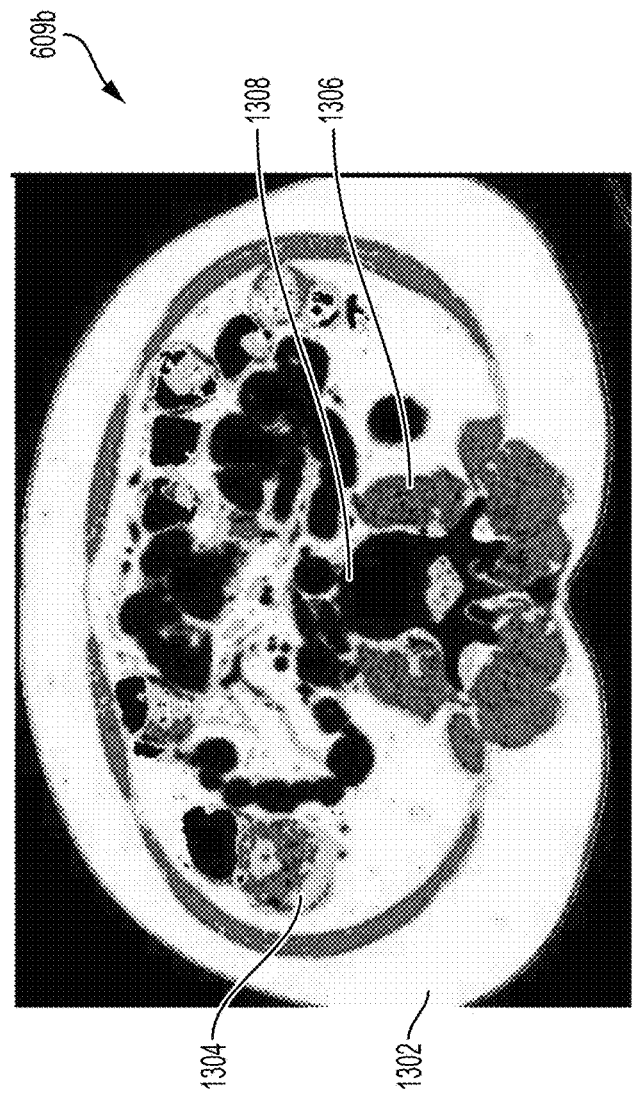
Figure 14:
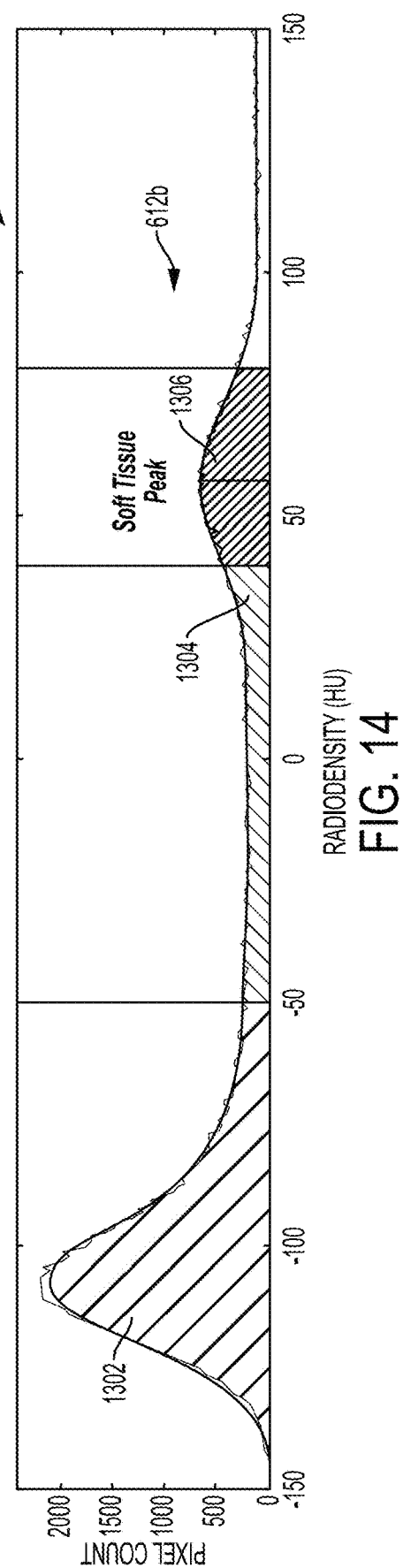

FIG. 13 shows another target medical image 609*b* for a different patient, according to an example embodiment of the present disclosure. Additionally, FIG. 14 shows a diagram of a distribution graph or nutrition-gram 1400 with data distribution 612*b*, which illustrates total tissue pixel counts for each radiodensity value in HU from the target medical image 609*b* of FIG. 12, according to an example embodiment of the present disclosure. In the example described in connection with FIGS. 13 and 14, the image analyzer 610 analyzes the medical image 609*b* to create the distribution nutrition-gram 1400 similar to the methods discussed above in conjunction with FIGS. 10 and 11.

In comparing FIGS. 10 and 11 with FIGS. 13 and 14, before CT scans, the patient associated with medical image 609*a* was medically diagnosed as being frail, while the patient associated with the medical image 609*b* was medically diagnosed as being healthy. The differences in data 612 between FIGS. 10 and 11 with FIGS. 13 and 14 confirm the actual physical differences between the patients and show that the frail patient did indeed have less muscle and/or a greater replacement of muscle by intramuscular adipose tissue. For instance, while the amount of fat tissue 1002, 1302 are about the same between the two patients, the patient associated with medical image 609*a* has significantly less muscle tissue 1006 and more transitional tissue 1004 (e.g., intramuscular adipose tissue). In particular, there is significant fat infiltration into the muscle tissue, which is shown as the transitional tissue 1004. In contrast, the patient associated with medical image 609*b* of FIG. 13 has more muscle tissue 1306 and less transitional tissue 1304 (e.g., muscle tissue infiltrated by fat tissue). The examples shown in FIGS. 10 and 11 and FIGS. 13 and 14 accordingly verifies that the distribution of radiodensity values and soft tissue peaks is correlated with the infiltration of muscle tissue by fat tissue, which can be automatically quantified for accurate analysis.

f. Data Analyzer

The example soft tissue engine 440 of FIG. 6 includes a data analyzer 616 to determine a soft tissue peak and related information from the distribution data 612. The example data analyzer 616 is configured to receive the distribution data 612 from the image analyzer 610 or access the distribution data from the memory 414. To determine a soft tissue peak, the example data analyzer 616 is configured to search for a local data peak located between −50 HU and 100 HU in the data distribution 612. The data analyzer 616 is configured to search only a subset of the entire distribution since the soft tissue peak will only have a radiodensity characteristic of muscle (having a radiodensity between 40 HU and 80 HU) or intramuscular adipose tissue (having a radiodensity between −50 HU and 40 HU). This subset also ignores visceral adipose tissue and subcutaneous adipose tissue (i.e., fat tissue), which may have a higher peak compared to the soft tissue peak. In addition, including a fat tissue peak in the analysis may complicate the search for the soft tissue peak.

After locating the soft tissue peak, the data analyzer 616 stores the radiodensity value of the soft tissue peak to a nutritional status record 618. The data analyzer 616 may also determine a number of pixels or a tissue surface area that corresponds to the soft tissue peak. In some outlier examples, the distribution data 612 may include bimodal soft tissue peaks. In these instances, the data analyzer 616 may record both peaks. Additionally or alternatively, the data analyzer 616 may average the bimodal distribution to determine an average peak, which is then recorded.

In an example, the data analyzer 616 is configured to analyze the data distribution 612*a* illustrated in the nutrition-gram 1100 of FIG. 11. In this example, the data analyzer 616 analyzes the distribution data between −50 HU and 100 HU. The data analyzer 616 determines that a soft tissue peak exists at about 20 HU, which corresponds to a large amount of transitional or muscle tissue within a relatively tight radiodensity range compared to other amounts of tissue that have radiodensity values greater or less than the range. The data analyzer 616 also determines a surface or cross-sectional area or pixel count value associated with the soft tissue peak. In this example, the soft tissue peak at 20 HU corresponds to a pixel count of about 1000 pixels.

FIG. 14 shows another data distribution 612*b* in a data distribution nutrition-gram 1400 that may be analyzed by the data analyzer 616. In this example, the data analyzer 616 determines that the soft tissue peak is located at about 55 HU. Additionally, the data analyzer 616 determines that the soft tissue peak corresponds to a pixel count of about 600 pixels.

In addition to soft tissue peak, the data analyzer 616 may also determine information related to the soft tissue peak. For example, since the soft tissue peak is usually in a Gaussian-type of distribution, the data analyzer 616 may determine tissue surface or cross-sectional area within a first and/or second deviation from the peak. In instances where the peak is skewed, the data analyzer 616 may determine how much tissue and/or how many pixels are within a defined radiodensity distance from the peak (e.g., a soft tissue reach). This may include determining a percentage of tissue or pixels that are to the right of the soft tissue peak and/or a percentage of tissue or pixels that have a radiodensity corresponding to muscle. Such information is indicative of a width of the peak, thereby indicating how much soft tissue has a radiodensity similar to the soft tissue peak. The data analyzer 616 may also determine radiodensity values at the first or second standard deviations and/or average radiodensity values between the first and second deviations.

The example data analyzer 616 may also determine ratios between the soft tissue peak and adjacent valleys (e.g., fat or thin tails). For example, in reference to the nutrition-gram 1100 of FIG. 11, the data analyzer 616 may determine a tissue surface or cross-sectional area or a pixel count of transition tissue at −30 HU and a tissue surface area or a pixel count of the muscle tissue at 80 HU. The data analyzer 616 then creates the ratio by comparing the tissue surface area or pixel count at the peak to the tissue surface area or pixel count at the valley. The ratios may indicate, for example, how much tissue is clumped at the soft tissue peak compared to tissue at other radiodensities. For example, the data distribution 612*a* shown in FIG. 11 has significant tissue peak to valley ratios, indicative that most of the muscle tissue has been infiltrated with fat tissue. The data distribution 612*a* also shows that the soft tissue peak is skewed to the left, with a small percentage of pixels to the right of the peak. This skew is also indicative that most of the muscle tissue has been infiltrated with fat tissue. By comparison, the data distribution 612*b* shown in FIG. 14 has lower soft tissue peak to valley ratios, indicative that the muscle is relatively free from intramuscular adipose tissue. The data distribution 612b also shows tissue with more evenly spaced radiodensity values. In addition, there is less, if any, skew in the soft tissue peak. The lack of skew means that there is a greater percentage of soft tissue to the right of the peak, indicative that the muscle tissue is relatively healthy.

Figure 15:
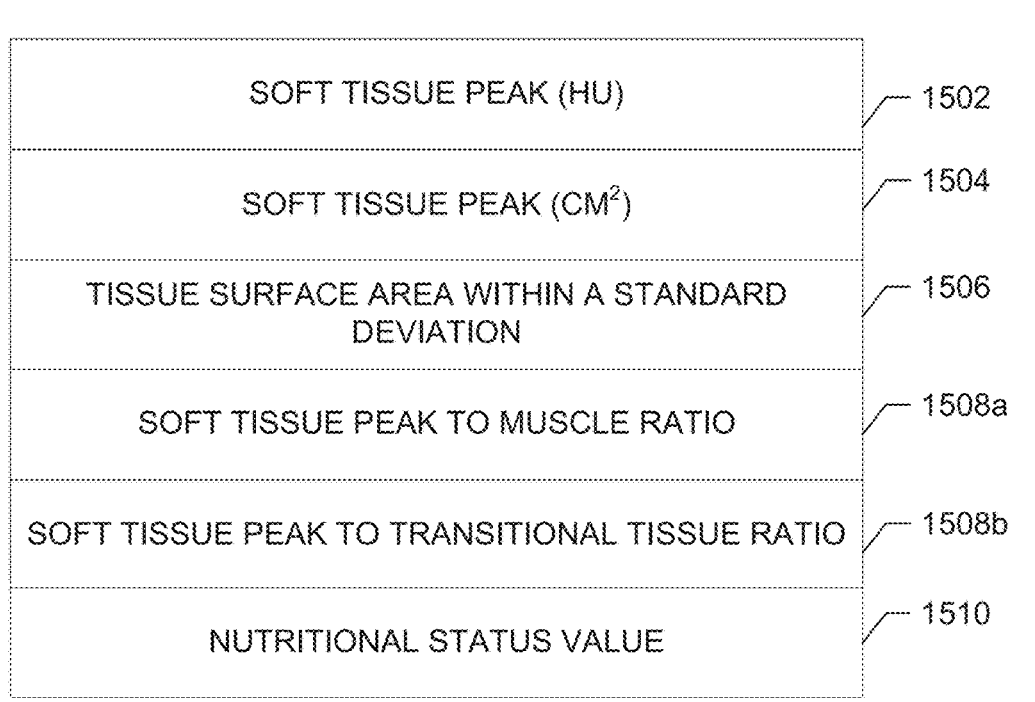
FIG. 15 illustrates a diagram of an example nutritional status record that may be created by the soft tissue engine of FIG. 6, according to an example embodiment of the present disclosure.

FIG. 15 shows a diagram of an example nutritional status record 618 that may be created by the data analyzer 616, according to an example embodiment of the present disclosure. After determining the soft tissue peak, the data analyzer 616 stores the soft tissue peak to the record 618. As indicated above, this includes the soft tissue peak radiodensity data 1502 and tissue surface area 1504. Further, the data analyzer 616 may be configured to store the standard deviation data 1506 (including soft tissue, skew, reach, and/or percentage of soft tissue to the right of the peak) and the ratio data 1508. In some instances, the data analyzer 616 may store at least some of the information from the distribution data 612 to the record 618, including tissue surface area data 1204.

The data stored to the record 618 is indicative of a nutritional status of a patient. Specifically, the soft tissue peak, standard deviation data 1506 (including soft tissue, skew, reach, and/or percentage of soft tissue to the right of the peak), and ratio data 1508 provide indications regarding the muscle quantity and quality of a patient in relation to intramuscular adipose tissue. A clinician may use the data stored in the record 618 to determine and/or recommend if a patient is nutritionally healthy or whether a nutritional therapy is needed. Additionally or alternatively, the nutritional therapy component 404 of FIGS. 4 and 5 may determine whether a nutritional therapy is to be administered based on the data within the record 618.

In some instances, the data analyzer 616 is configured to determine a numerical score or textural indication (referred to as a nutritional status value 1510) of a patient's nutritional status based on the radiodensity value of the soft tissue peak 1502, the tissue area of the soft tissue peak 1504, the standard deviation data 1506 (including soft tissue, skew, reach, and/or percentage of soft tissue to the right of the peak), and/or the ratio data 1508. For example, the data analyzer 616 may compare the radiodensity value of the soft tissue peak 1502 to a predetermined threshold (e.g., 40 HU, 45 HU, 50 HU, etc.). The data analyzer 616 may be configured to determine and/or recommend that a patient is nutritionally unhealthy if the soft tissue peak is below the predetermined threshold. In other examples, multiple thresholds may exist that correspond to different malnutrition levels. For instance, a soft tissue peak between 35 HU and 45 HU may be classified as 'slightly malnourished', while a soft tissue peak between 28 HU and 35 HU may be classified as 'moderately malnourished', and a soft tissue peak below 28 HU may be classified as 'severely malnourished'. In other examples, a nutritional score (on a scale of 1 to 100, for example) may be determined based on the radiodensity value of the soft tissue peak. For instance, a soft tissue peak radiodensity value between −50 and 80 may be scaled to a score between 1 and 100. Then, based on the scaled score, the data analyzer 616 may be configured to determine a textual nutritional characterization. The data analyzer 616 stores the scaled score and/or the textual characterization to the record as a nutritional status value 1510.

While the nutritional status value 1510 was described as being determined from the soft tissue peak 1502, it should be appreciated that the other soft tissue information 1504, 1506, and/or 1508 may also be used to determine and/or evaluate the nutritional status. For example, the nutritional status value 1510 may be determined based on a combination of a patient's first standard deviation 1506 (including soft tissue, skew, reach, and/or percentage of soft tissue to the right of the peak) of the soft tissue peak, a muscle surface area, a surface area associated with the soft tissue peak, and radiodensity value of the soft tissue peak. Each of the different data types may be assigned a weight, which when normalized, scaled, and/or combined, is compared to one or more predetermined thresholds to determine a nutritional status. In an example, a patient may have a soft tissue peak at 40 HU, which alone may indicate a patient is 'slightly malnourished'. However, the tissue surface area within a first standard deviation may show a wide distribution where a significant amount of tissue is muscle. The data analyzer 616 uses the standard deviation data to determine that the patient has instead a 'healthy' nutritional status.

The nutritional status value 1510 may also be determined by comparing the soft tissue peak 1502 and/or the related soft tissue peak information 612, 1504, 1506, and/or 1508 to thresholds that are adjusted based on patient demographic information. For instance, as patients age, muscle tissue tends to degenerate and be replaced by intramuscular adipose tissue. In some embodiments, the data analyzer 616 is configured to adjust one or more thresholds based on a patient's age. In the example above, the value of '35 HU' was described as being a threshold between slight and moderate malnourishment. The example data analyzer 616 may adjust this threshold (as well as the other thresholds) such that a detection of moderate malnourishment occurs at a lower radiodensity. The data analyzer 616 may be programed with an algorithm that specifies that the current age of the patient is subtracted from a reference value of '45 HU' and divided by 10. The result of this computation is then subtracted from the radiodensity threshold at 35 HU. For a 65 year old patient, the data analyzer 616 calculates an adjustment of 2 HU ((65 HU−45 HU)/10). Thus, the threshold between moderate and slight malnourishment is 33 HU instead of 35 HU.

In other examples, the data analyzer 616 may adjust the threshold(s) based on other patient demographic information, such as height, race, gender, disease affliction, injury type, subsequent scheduled medical procedure type, etc. For instance, the data analyzer 616 may access a patient's medical record and determine that the patient is to undergo chemotherapy, which is characterized as a relatively intensive procedure. The data analyzer 616 may accordingly adjust the threshold(s) based on medical procedure type to ensure the patient has sufficient amino acid reserves for responding to the cancer treatment. In such an embodiment, the data analyzer 616 may store to the record 618 an indication, for instance, that the patient is nutritionally acceptable for chemotherapy (and/or a certain class of medical procedures). In addition, the data analyzer 616 may determine and store an indication to the record 618 of procedures (e.g., surgery) or medical procedure classifications for which the patient is considered malnourished.

In some embodiments, it should be appreciated that the data analyzed by the data analyzer 616 is self-contained to muscle quality and/or quantity data determinable from the target medical image 609. In these embodiments, the patient's data is not compared to population data of other patients to determine a nutritional status. This may be beneficial since population data may not be complete or representative of the patient undergoing the nutritional analysis. In addition, not having to use population data reduces chances of uncharacteristic patients causing the data analyzer 616 to misidentify a nutritional status of a patient.

While the example soft tissue engine 440 can operate without population data, in some embodiments, the data analyzer 616 may be configured to use patient population data for determining and/or evaluating nutritional status. The use of population data may provide an indication of how a current patient relates to other patients with similar demographics and muscle quality metrics and whether those other comparable patients were nutritionally healthy. In an example, the data analyzer 616 is configured to determine, among a pool of population data, individuals that have similar demographic traits (e.g., height, weight, age, gender, etc.) as the patient under analysis. The data analyzer 616 then compares the soft tissue peak 1502 and/or the soft tissue peak information 612, 1504, 1506, and/or 1508 to the soft tissue peaks and/or related information of the identified individuals. The data analyzer 616 determines there is a match if, for example, the radiodensity value of the soft tissue peak 1502 between the patient and the identified individuals is within a predetermined threshold. The data analyzer 616 determines a nutritional status of the matching individuals and stores this nutritional status to the record 618. In some instances, the data analyzer 616 may average the nutritional status among the matching individuals and store the averaged value to the record 618. In these instances, the data analyzer 616 may weight the different nutritional statuses based on closeness of the soft tissue peaks of the matching individuals to the soft tissue peak 1502 of the patient and closeness of their demographic traits.

While the above disclosure focuses on the processing of a single medical image, it should be appreciated that the data analyzer 616 may be configured to determine a patient's nutritional status from two or more medical images. For instance, the data analyzer 616 (and the image analyzer 610) may determine soft tissue peaks 1502 and related information 1504, 1506, and/or 1508 from one or more data distribution(s) 612 of two or more medical images. The data analyzer 616 is configured to determine a soft tissue peak for each distribution. The data analyzer 616 then averages or otherwise combines the soft tissue peaks. Further, the data analyzer 616 determines a nutritional status of the patient based on the averaged and/or combined soft tissue peaks. The determined nutritional status 1510 as well as the combined or averaged soft tissue peaks 1502 are stored to the nutritional status record 618. In some instances, the individual soft tissue peaks may also be stored to the record 618.

In the examples in which more than one medical image is processed, the data analyzer 616 may use statistical analysis to determine if a soft tissue peak and/or related information is a statistical outlier. For instance, three medical images in a sequence may correspond to a soft tissue peak between 45 HU and 48 HU while a fourth medical in the same sequence image corresponds to a soft tissue peak at 32 HU. The data analyzer 616 determines that the soft tissue peak of the fourth medical image is a statistical outlier. In these instances, data analyzer 616 may discard the soft tissue peak information related to the fourth medical image g. Network Interface

The example soft tissue engine 440 of FIG. 6 includes a network interface 620 to transmit, for example, the nutritional status record 618 to the HIS 450, the EMR server 426, the pharmacy preparation system 420, the at least one nutritional infusion pump 422, and/or the clinician device 424. In instances in which the soft tissue engine 440 includes the nutritional analysis engine 442, the soft tissue engine 440 transmits the records internally to the nutritional analysis engine 442. In these instances, the soft tissue engine 440 may still transmit the nutritional status records 618 externally to the HIS 450, the EMR server 426, the pharmacy preparation system 420, the at least one nutritional infusion pump 422, and/or the clinician device 424.

To transmit the record 618, the example network interface 620 is configured to structure the information within the record 618 into one or more message(s) 414. In some embodiments, the network interface 620 may also structure the distribution data 612 and/or the related medical images 609 in the one or more message(s) 414. The network interface 620 may individually address the message(s) 414 to, for example, the EMR server 426 and/or the pharmacy preparation system 420. In other examples, the message(s) 414 may be transmitted to a gateway server, which determines a destination recipient. For instance, the clinician device 424 may subscribe with a gateway to receive information related to a specific patient. The gateway receives and determines that record 618 is associated with the subscribed patient and transmits the record to the clinician device 424. As provided in more details below, transmission of the nutritional status record 618 enables, for example, a nutritional therapy and/or components of a nutritional solution to be automatically determined. The transmission of the nutritional status record 618 (or individual information within the record 618, such as the nutritional status value 1510) also enables a clinician to determine an approximate lean body mass or nutritional health of a patient, which enables the clinician to determine if the patient may undergo an intensive medical procedure. At the least, the nutritional status value 1510 provides a post-procedural risk indicator. In some instances, a clinician may attempt to reduce a patient's risk and improve a procedural outcome by scheduling a nutritional feeding before and/or after the procedure.

h. Segmentation Processor

The example soft tissue engine 440 has been described herein as determining muscle quality and muscle quality from an entire two-dimensional medical image. In some embodiments, the soft tissue engine 440 may use a segmentation processor 622 configured to select a portion of a medical image (e.g., segment) to determine muscle quality and/or quantity. Segmentation focuses the quantification of muscle quality and quantity on a particular area (e.g., the skeletal psoas muscle) while disregarding internal organs, abdominal muscle, visceral adipose tissue, and/or subcutaneous adipose tissue. For instance, some internal organs have a radiodensity between 30 HU and 60 HU, which overlaps with muscle radiodensity between 40 HU and 80 HU. The result is that, in some instances, the image analyzer 610 may include organ tissue in the quantification of muscle tissue if an entire image is analyzed.

There are a number of methods that may be used to segment specific muscle tissue. The segmentation processor 622 described herein is configured to use one or more of these methods to isolate certain tissue. To segment muscle tissue, for example, the segmentation processor 622 is configured to receive one or more target medical images 609 from the image selector 608. In embodiments where the segmentation processor 622 is used, the image selector 608 may be programmed to send images to the segmentation processor 622 instead of directly to the image analyzer 610. In other embodiments, a technician may provide an indication, via the user interface 604, that one or more target medical images 609 are to be segmented. In these embodiments, the technician may select a segmentation method, if more than one is available. Further, the user interface 604 may be configured to display an image after segmentation and enable a technician to adjust the segmentation boundaries.

The segmentation processor 622 is configured to send the segmented image to the image analyzer 610 after segmentation is complete. A data distribution 612 is determined from the segmented image using the same techniques described above in conjunction with discussion regarding the image analyzer 610. However, the image analyzer 610, in these embodiments, is configured to analyze the pixels within the segmented boundary and disregard the other pixels. The segmentation processor 622 may use any one of the methods described below individually or in combination.

I. Internal Organ Segmentation

In one method, the example segmentation processor 622 is configured to remove internal organs and tissue from one or more target medical image(s) 609. In contrast to core or skeletal muscles, abdominal cavity organs and vasculature have relatively little symmetry with respect to the sagittal plane in an axial CT image. The segmentation processor 622 may be configured to perform statistical similarity quantification (e.g., determine an SSIM index) of the anatomic structure in a two-dimensional medical image. The segmentation processor 622 compares the statistical similarity quantification of the anatomy to a threshold. Here, the segmentation processor 622 may divide a medical image into two halves and compare the shapes of the tissue at the same location on each of the halves. Based on correlations between the shapes in each half, the segmentation processor 622 assigns a similarity value to each of the pixels. Anatomy or pixels that are below the threshold are removed, disregarded, or segmented by the segmentation processor 622. In contrast, anatomy or pixels that are greater than the threshold are retained within the medical image for processing by the image analyzer 610.

Figure 16:
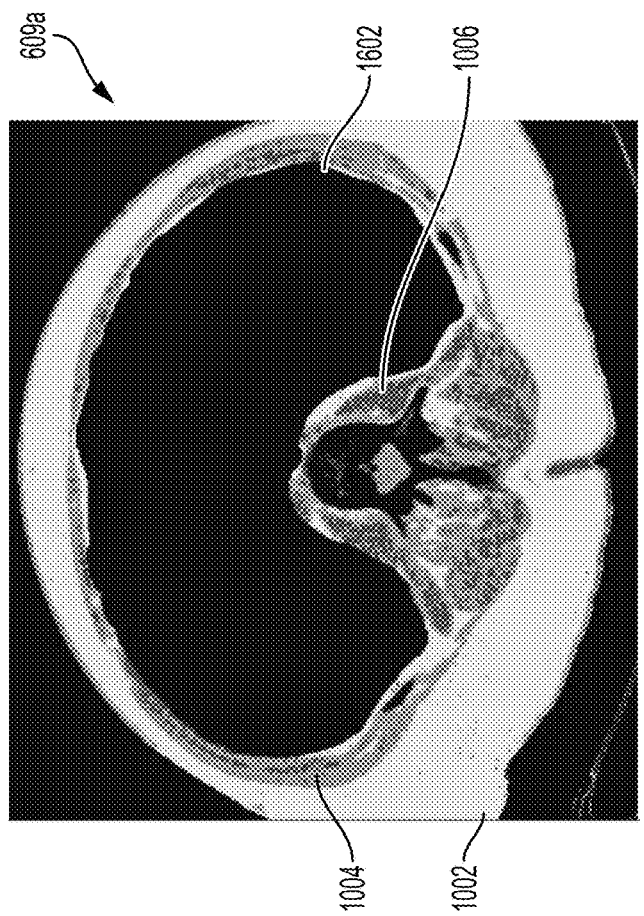
FIGS. 16 and 18 illustrate examples of segmentation capable of being performed by the soft tissue engine of FIG. 6 on the respective medical images of FIGS. 10 and 13, accordingly to example embodiments of the present disclosure.

FIG. 16 shows an example of segmentation capable of being performed by the segmentation processor 622 on the medical image 609a of FIG. 10. For clarity, the illustrated segmentation was performed manually. However, the illustrated segmentation is representative of tissue segmentation that may be performed by the segmentation processor 622. The medical image 609a of FIG. 16 shows region 1602 where the internal tissue (and bone tissue) has been removed and replaced with black pixels. As shown in the pre-segmented medical image 609a of FIG. 10, the internal organs and surrounding fat tissue are relatively asymmetric. In comparison, the skeletal and abdominal muscle tissue within regions 1004 and 1006 and surrounding fat tissue within the region 1002 are relatively symmetric. Segmentation accordingly causes the designated region 1002 corresponding to fat tissue (i.e., visceral adipose tissue and subcutaneous adipose tissue), the designated region 1004 corresponding to transitional tissue (i.e., intramuscular adipose tissue), and the designated region 1006 corresponding to the skeletal and abdominal muscle tissue to be retained in the medical image 609a (as shown in FIG. 15).

Figure 17:
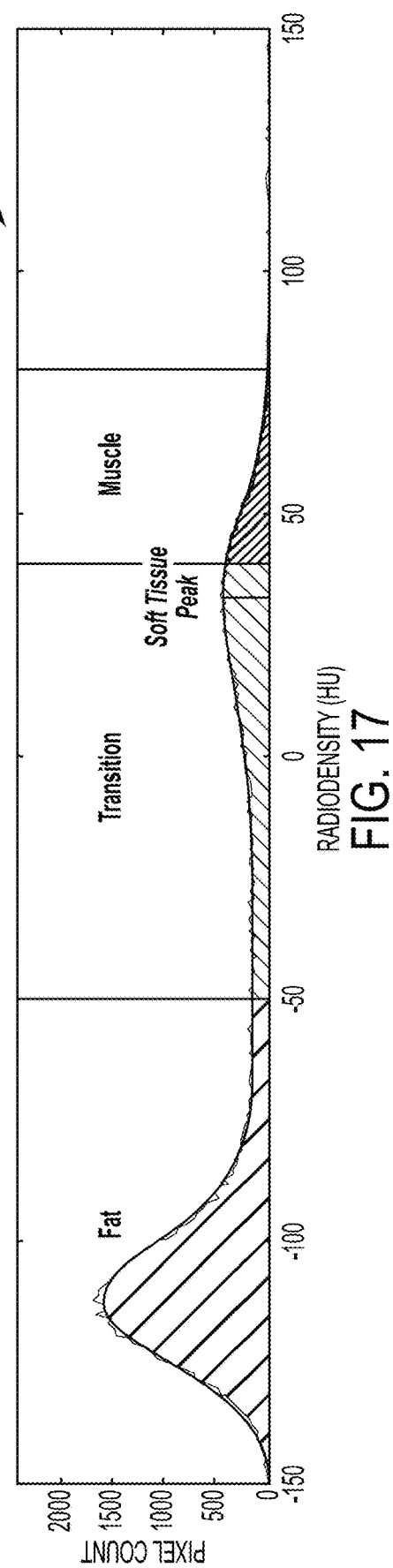
FIGS. 17 and 19 illustrate distribution graphs created by the soft tissue engine of FIG. 6 based on the respective segmented medical images of FIGS. 16 and 18, accordingly to example embodiments of the present disclosure.

FIG. 17 shows a distribution graph or nutrition-gram 1700 created by the image analyzer 610 based on the segmented medical image 609a of FIG. 16. Compared to the nutrition-gram 1100 of FIG. 11, the nutrition-gram 1700 has significantly less fat, transitional, and muscle tissue. However, the tissue remaining in the nutrition-gram 1700 corresponds to skeletal muscle and related intramuscular adipose tissue, which are more indicative of a patient's amino acid reserves and overall nutritional health. It should be noted that the soft tissue peak shown in FIG. 17 has a radiodensity that is about 10 HU greater than the radiodensity of the soft tissue peak shown in the nutrition-gram 1100 of FIG. 11. This difference indicates that quantification of the organs may skew results, which may mistakenly show that a patient is less healthy than in reality since the radiodensity of the organs overlaps with the radiodensity of intramuscular adipose tissue. Accordingly, segmentation performed by the segmentation processor 622 provides more accurate results regarding muscle quality. Further, segmentation reduces a number of pixels that have to be analyzed by the image analyzer 610.

Figure 18:
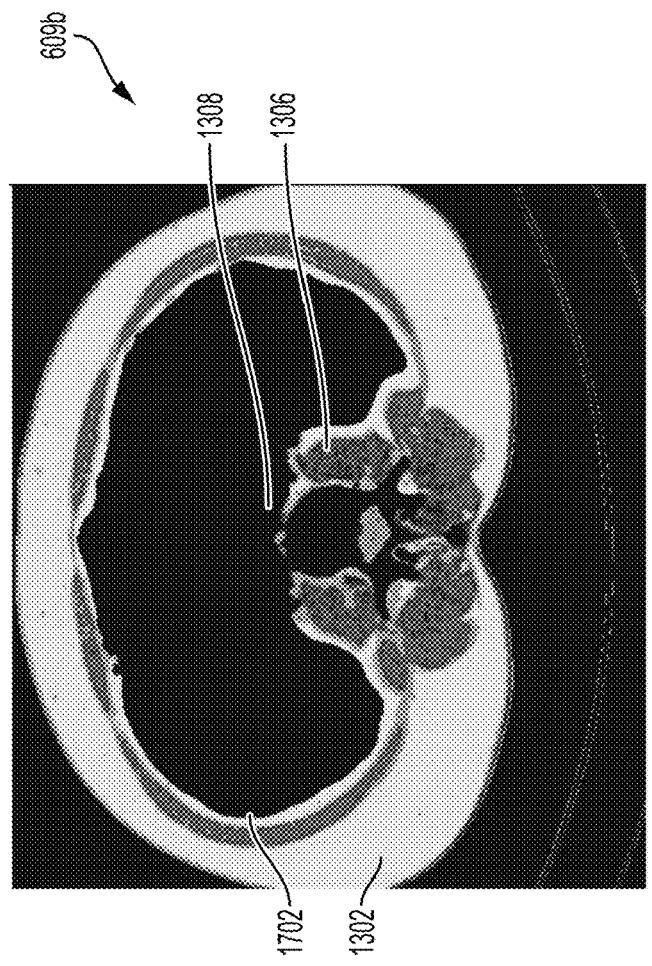
Figure 19:
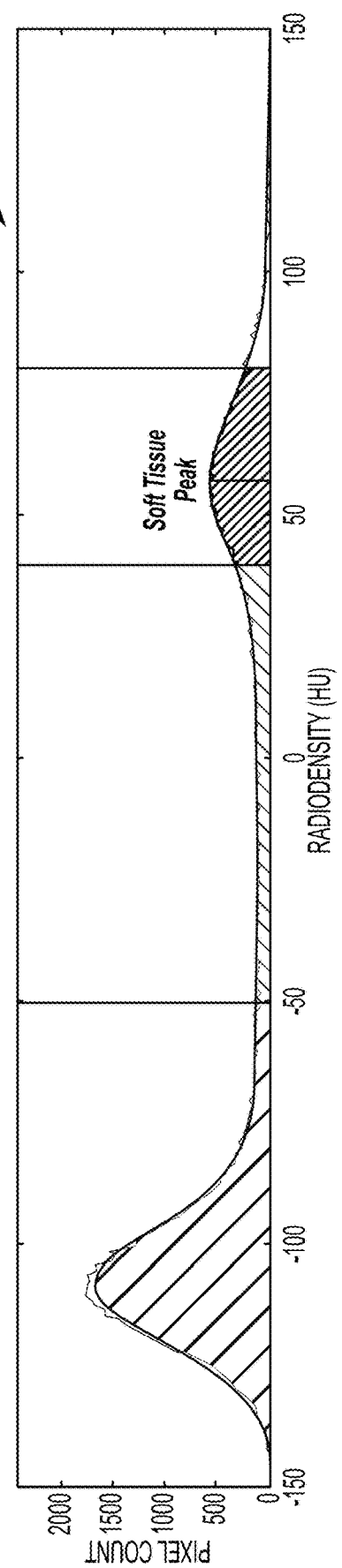

FIG. 18 shows an example of segmentation capable of being performed by the segmentation processor 622 on the medical image 609b of FIG. 13. Similar to FIG. 16, for clarity, the illustrated segmentation was performed manually. However, the illustrated segmentation is representative of tissue segmentation that may be performed by the segmentation processor 622. FIG. 19 shows a distribution graph or nutrition-gram 1900 created by the image analyzer 610 based on the segmented medical image 609b of FIG. 18. In the example described in connection with FIGS. 18 and 19, designated region 1802 has been segmented. Similar to the results shown in FIGS. 16 and 17, the medical image 609b of FIG. 18 and the nutrition-gram 1900 of FIG. 19 show that segmentation reduces the amount of non-critical tissue analyzed. Compared to the medical image 609b of FIG. 13 and the nutrition-gram 1400 of FIG. 14, the soft tissue peak in the nutrition-gram 1900 is relatively unchanged. This is a result of the patient having more skeletal muscle, which is not segmented out.

2. Center-of-Mass Segmentation

The segmentation processor 622 may also be configured to segment one or more medical image(s) using a center-of-mass or center-of-gravity routine or algorithm. Here, the segmentation processor 622 is configured to compute or determine a center-of-mass of a target medical image 609. To determine a center-of-mass, the segmentation processor 622 analyzes all of the tissue pixels within the two-dimensional medical image 609 to determine a lateral and longitudinal center. For instance, the segmentation processor 622 determines a width of a patient's anatomy in a medical image and divides the width in half. The longitudinal center corresponds to a middle of the width. An intersection of the lateral and longitudinal centers is the center-of-mass. It should be appreciated that other center-of-mass methods may also be used. For example, a weighted average of pixel two-dimensional coordinates in the medical image 609 may be analyzed to determine a center or origin.

After a center-of-mass is determined, the example segmentation processor 622 is configured to determine a region-of-interest, which corresponds to a polygon having a center located at the center-of-mass. For example, the segmentation processor 622 may be configured to create a rectangular-shaped region-of-interest with a specified length and width. In other examples, the region-of-interest may include a square, a triangle, an oval, a circle, a pentagon, a hexagon, etc.

The segmentation processor 622 positions, overlays, or otherwise imposes the region-of-interest with respect to the target medical image 609 by aligning a center of the region-of-interest with the determined center-of-mass. The segmentation processor 622 designates tissue within the region-ofinterest as segmented tissue to be analyzed by the image analyzer 610. Tissue outside the region-of-interest is segmented out from analysis by the segmentation processor 622.

In some instances, the segmentation processor 622 is configured to iteratively segment the target medical image 609 to more accurately include, for example, the psoas muscle. For instance, after using the method described above to segment, the segmentation processor 622 determines a new center-of-mass within the region-of-interest using only bone tissue. Using only the bone tissue in the center-of-mass analysis causes the center-of-mass to shift downward toward the L3 vertebra or spine. A second region-of-interest may then be created at the new center-of-mass. The second region-of-interest may also have a rectangular shape. However, the second region-of-interest may have smaller dimensions to further focus on or isolate the psoas muscles.

The segmentation processor 622 may perform another iteration on the second region-of-interest by calculating a third center-of-mass within the second region-of-interest using all tissue within the region. This additional iteration may move the center-of-mass to a center of the psoas muscles. In some embodiments, the bone tissue may be disregarded in the third center-of-mass analysis. After the third center-of-mass has been determined, the segmentation processor 622 creates a third region-of-interest that is dimensioned to include primarily the psoas muscles. The segmentation processor 622 then transmits the segmented medical image to the image analyzer 610 to determine muscle quality and quantity.

Figure 20:
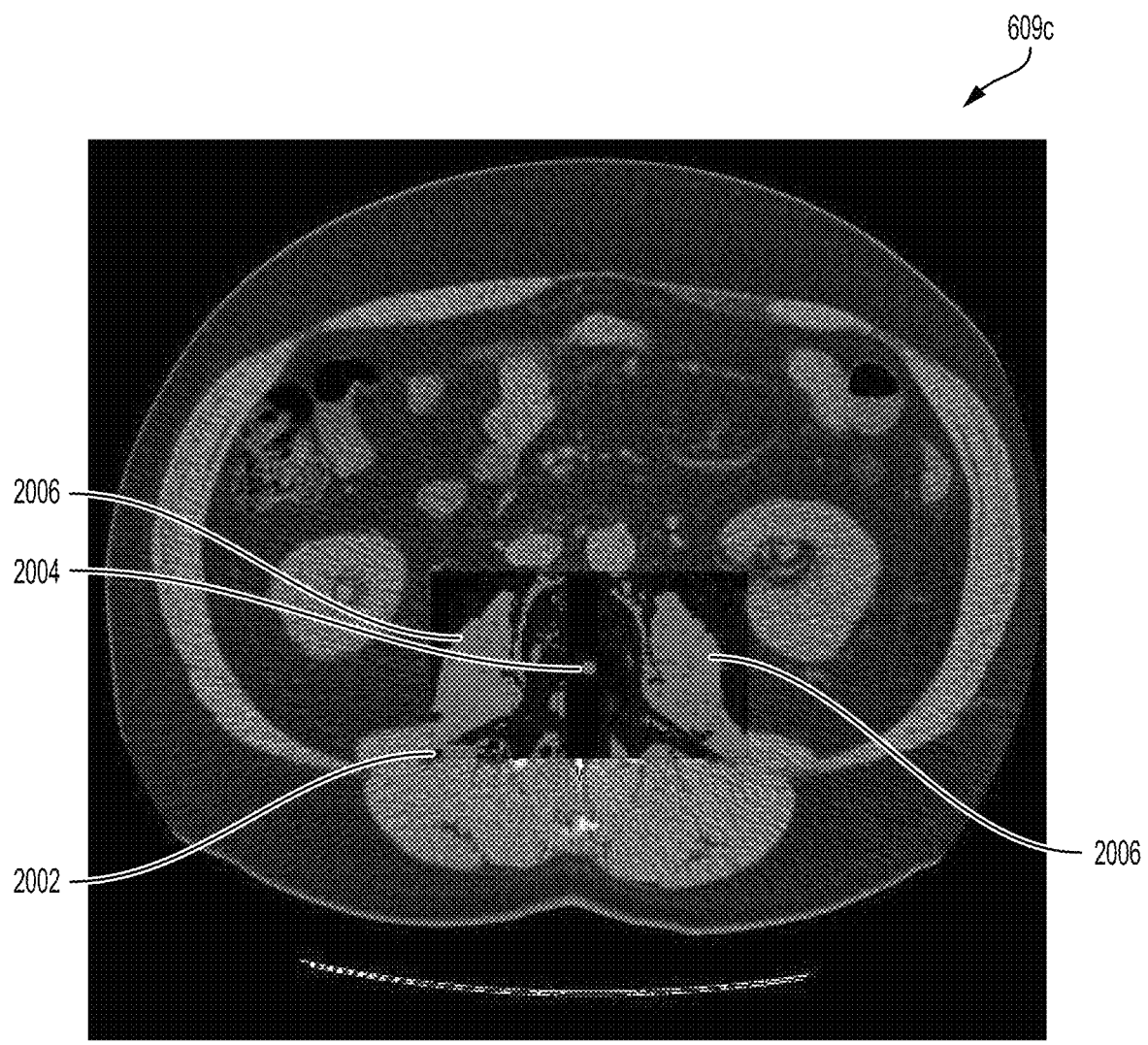
FIG. 20 illustrates a diagram of an example medical image that has been segmented using the center-of-mass approach by the soft tissue engine of FIG. 6, according to an example embodiment of the present disclosure.

FIG. 20 shows a diagram of an example a medical image 609*c* that has been segmented using a center-of-mass approach. The illustrated example shows a region-of-interest 2002 after the third iteration. The region-of-interest 2002 has a center-of-mass 2004 that is centered within the psoas muscles 2006. This segmentation isolates the muscle quality and quantity analysis to only the psoas muscles, which are accurate indicators of total body amino acid reserves (and overall patient nutritional status). This segmentation method also accounts for abnormalities in a patient, where muscle shape may be asymmetric or distorted due to injury or degradation of the muscles with age or disease. Further, computation of a center-of-mass is relatively computationally efficient compared to pattern or template matching, which is described below.

3. Shape and Template Matching Segmentation

The example segmentation processor 622 of FIG. 6 may also use one or more shape or template matching method(s) to perform segmentation. In some embodiments, the segmentation processor 622 may combine the methods disclosed below with the segmentation methods discussed above to further segment certain muscle tissue. For example, after a region-of-interest is determined, the segmentation processor 622 may apply one or more shape or template matching techniques to further segment muscle tissue.

A first method, described in a white paper by Chung at al. titled, "Automated Segmentation of Muscle and Adipose Tissue on CT Images for Human Body Composition Analysis", which is incorporated herein by reference, discloses segmentation of muscle tissue from fat and organ tissue using a shape deformation model and an appearance probability model. In the appearance model, Chung at al. disclose that muscle segmentation is performed by assigning a probability of a pixel in a two-dimensional image (or a greyscale conversion thereof) corresponding to muscle tissue. Probabilities exceeding a certain threshold are deemed to correspond to pixels representing muscle tissue. Chung at al. disclose that the pixels representing muscle tissue are then analyzed through a shape deformation model to approximate surface area. In particular, image deformations in the muscle pixel image are parametrized using a Free Form Deformation ("FFD") model consisting of a B-spline cubic interpolation of regular lattice points. Lattice point deformations are coded with respect to a mean shape estimated from a set of training images. The steps for computing shape parameters of muscle from manually segmented images included (1) performing an affine alignment and mean shape computation, (2) performing a non-rigid alignment using an FFD model, and (3) encoding incremental deformations using a Principal Component Analysis ("PCA").

A second method, described in a white paper by Popuri at al. titled, "Body Composition Assessment in Axial CT Images using FEM-based Automatic Segmentation of Skeletal Muscle", which is incorporated herein by reference, builds off of Chung at al. by limiting complex segmentation boundaries where a deformation analysis may be needed. Popuri at al. disclose the use of a template-based segmentation approach where a binary template defining an initial shape is deformed via non-rigid or deformable registration to match muscle tissue in a two-dimensional image. Popuri at al. use a finite element method ("FEM"), which uses a non-uniform mesh adapted to contour an initial shape of the template to parameterize the deformation field. For a two-dimensional image, Popuri at al. disclose that muscle segmentation is performed by computing an optimal segmentation boundary by optimally deforming a template such that the template substantially matches the two-dimensional image. Image deformations are defined using a FEM-based deformable registration framework that is adapted for template-based segmentation.

i. Population Processor

The example soft tissue engine 440 of the nutritional status diagnostic component 402 of FIG. 6 may also include a population processor 630 configured to analyze one or more medical images 412 stored in a warehouse or long-term storage to create correlations between population demographics and muscle mass or muscle quality. The example population processor 630 is configured to access or otherwise obtain medical images 412 stored in the EMR server 426, a medical warehouse accessibly through the HIS 450, the memory 614, or any other persistent storage medium configured to store patient medical records. In some instances, a user may specify, via the user interface 604, a directory or electronic address of the patient information to be analyzed. In addition to medical records, the population processor 630 may also receive corresponding patient demographic information, physiological information, disease information, treatment information, and/or treatment cost information.

The population processor 630 identifies the medical images 412 within the received information and transmits the images to the image selector 608 for processing. As discussed above, the image processor 608, the image analyzer 610, the data analyzer 616, and/or the segmentation processor 622 are configured to determine muscle quality and/or a nutritional status for each patient whom records are available. In instances where medical images have been recorded at different points of treatment, the population processor 630 is configured to request that muscle quality and/or a nutritional status is to be determined for each set of medical images. The process to determine muscle quality and/or nutritional status from medical images may take a few milliseconds for each patient. The example soft tissue engine 440 accordingly may determine the muscle quality and/or the nutritional status (e.g., the distribution data 612) of hundreds-of-thousands or millions of patients within a matter of minutes, or at least in less than an hour.

After determining the muscle quality and/or nutritional status, the example population processor 430 is configured to correlate the muscle quality and/or nutritional status to other patient information, such as demographics, treatment plan, and/or costs. The correlation provides meaningful data that may be used to determine a nutritional status of future patients or conditions for recommending nutritional therapies. In some instances, the distribution data 612 for all the patients may be analyzed to determine thresholds for creating labels or values for a nutritional status. For example, a distribution graph or nutrition-gram of soft tissue peaks may be charted in relation to patient health. The population processor 430 (or a statistician) may identify patient characteristics within medical records that are related to muscle quality, such as, medical diagnosis, semi-subjective analyses, BMI indices, physician notes, and/or combinations thereof. Soft tissue peaks associated with healthy patients having normal muscle mass generally cluster between 45 HU and 60 HU while soft tissue peaks associated with patient with decreased muscle mass, such as sarcopenia, generally cluster between 30 HU and 40 HU. Further, soft tissue peaks of patients with decreased muscle function (i.e., patients with severe sarcopenia) generally cluster between 15 HU and 25 HU. Such clusters may be analyzed by the population processor 430 to determine thresholds for determining values or indications of nutritional status.

In addition, the example population processor 430 may be configured to determine costs associated with mistreatment or delayed nutritional therapy. For example, the population processor 430 may identify patients with soft tissue peaks indicative of reduced muscle mass and/or reduced muscle function. For these patients, the population processor 430 may determine which medical procedures or treatments were performed. As mentioned above, patients with reduced muscle mass have less amino acid stores to aid in recovery. The population processor 430 can quantify the costs associated with a prolonged recovery for these patients based on how many days of post-procedural hospital stays were needed, post-procedural medical procedures performed to address complications, and/or whether (or when) a nutritional therapy was started. Regarding when a nutritional therapy is traditionally started, the American Society for Parenteral and Enteral Nutrition ("ASPEN") provides guidelines that specify a patient is not to receive a nutritional therapy until 7 to 14 days after a procedure. However, a patient may be malnourished before a procedure and will therefore continue to be malnourished after the procedure for one to two weeks before nutritional therapy is started if the guidelines are followed. The population processor 430 can determine the medical costs incurred, based on the medical procedures and costs in a patient's medical record, to determine how much the delayed nutritional therapy will cost the patient and the hospital. In instances where separate CT scans were performed during this prolonged recovery time for the patient, the population processor 430 may also correlate muscle mass decrease due to medical procedures and post-procedural treatments.

The example population processor 630 may also be configured to correlate patient muscle quality and/or nutritional status to post-procedural long term care or quality of life. A patient's medical record may indicate, for example, where a patient was discharged after a medical procedure. For instance, healthy patients may be discharged from a hospital to their homes with no follow-up care. By comparison, patients with complications from a procedure may be discharged to their homes with a prescription for home care or physical therapy. Patients with more serious complications may be discharged to a nursing home or an intensive care unit ("ICU"). The example population processor 630 is configured to determine the long term care type, duration, and costs. The population processor 630 then correlates the long term care, type, duration, and costs to the patient's muscle quality and/or nutritional status. These correlations may be useful for prescribing nutritional therapies to patients at risk of developing serious complications (e.g., patients with muscle masses that are similar to muscle masses of patients with similar demographics that received significant post-procedural care), thereby improving their discharge outlook and improving recovery times.

The example population processor 630 is configured to transmit one or more message(s) 632 to the EMR server 426 and/or the HIS 450 that includes a muscle quality and/or nutritional status for the analyzed patients. The messages 632 may also include thresholds for determining nutritional status and/or correlations between patient information and muscle quality and/or nutritional status. The messages 632 may further include correlations between muscle quality and post-procedural complications and associated costs. In some instances, the analysis server 408 and/or the EMR server 426 may use the information in the messages 432 to determine nutritional therapy treatment recommendations and/or guidelines.

j. Example Process to Determine or Evaluate a Patient's Nutritional Status

Figure 21:
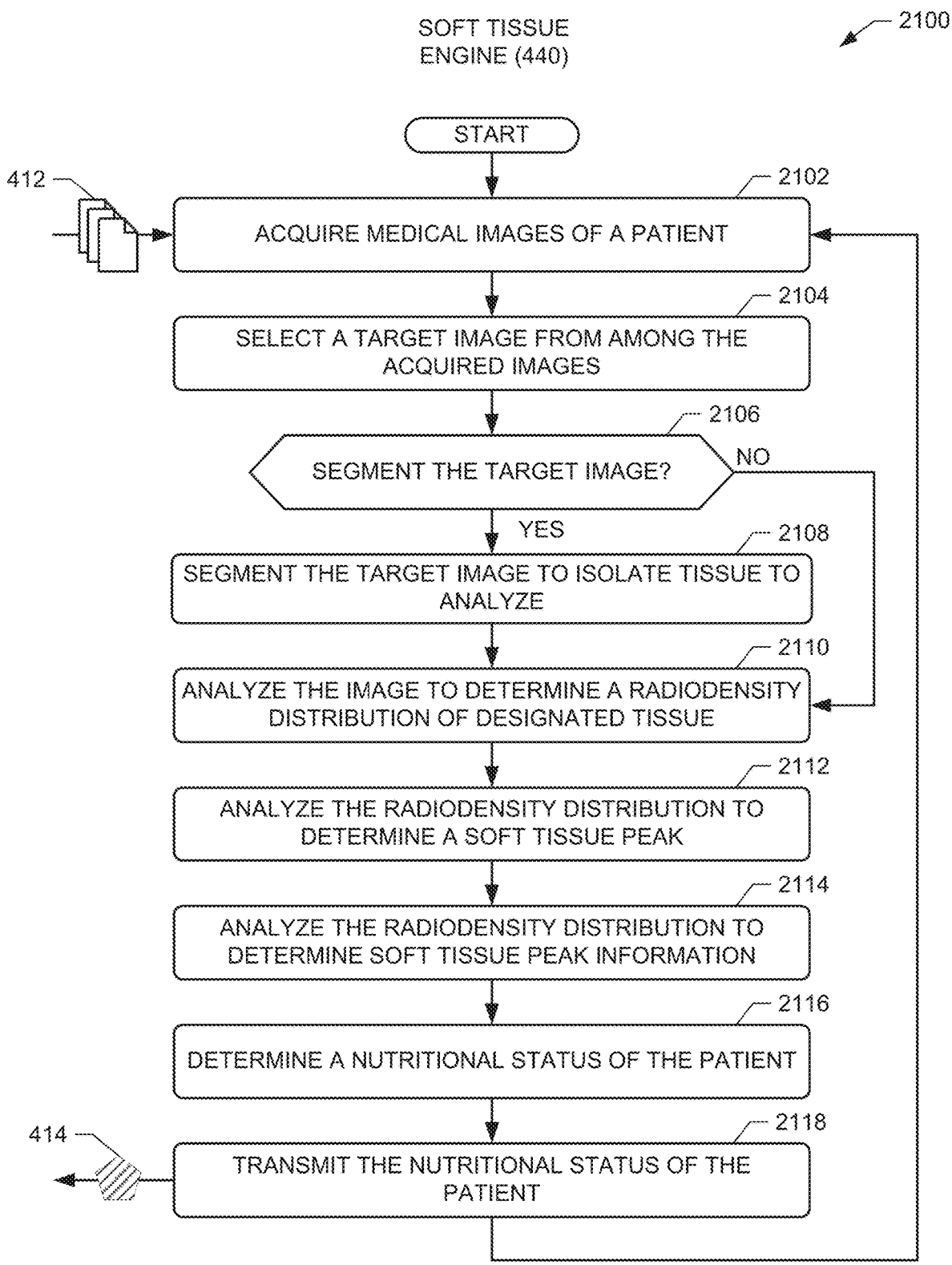
FIG. 21 illustrates a flow diagram representing an example procedure to determine a nutritional status of a patient from muscle quality and muscle quantity data obtained from one or more medical images, according to an example embodiment of the present disclosure.

FIG. 21 shows a flow diagram illustrating an example procedure 2100 to determine and/or evaluate a nutritional status of a patient from muscle quality and muscle quantity data obtained from one or more medical images, according to an example embodiment of the present disclosure. The example procedure 2100 may be carried out by, for example, the soft tissue engine 440 of the analysis server 408, as described in conjunction with FIGS. 4 to 20. Although the procedure 2100 is described with reference to the flow diagram illustrated in FIG. 21, it should be appreciated that many other methods of performing the functions associated with the procedure 2100 may be used. For example, the order of many of the blocks may be changed, certain blocks may be combined with other blocks, and many of the blocks described are optional. For example, in instances where the soft tissue engine 440 does not include the segmentation processor 622, the segmentation steps may be omitted.

Procedure 2100 begins when one or more medical image(s) 412 of a patient is acquired and/or received by the soft tissue engine 440 (block 2102). The medical images 412 may include, for example, CT slices of a mid-section of the patient. The medical images 412 include radiodensity for the tissue shown within the images 412. After acquiring the images, the soft tissue engine 440 is configured to select a target medical image 609 from among the acquired images (block 2104). As discussed in more detail above in connection with FIG. 6, the soft tissue engine 440 may select an image by identifying which image contains the least (or less) bone tissue between an area corresponding to the patient's L3 and L4 vertebras.

After at least one target image 609 is identified, the example soft tissue engine 440 determines if the target image(s) are to be segmented (block 2106). If the images are to be segmented, the soft tissue engine 440 uses one or more routines and/or algorithms to segment a portion of the target image(s) for further analysis (block 2108). As discussed above, the soft tissue engine 440 may segment out internal organs using a symmetry routine. The soft tissue engine 440 may also segment bone tissue by filtering pixels based on radiodensity values. Further, the soft tissue engine 440 may use an iterative center-of-mass routine and/or one or more shape/template matching routines to isolate certain muscle tissue (e.g., skeletal muscle tissue) for further analysis.

After segmentation, the soft tissue engine 440 analyzes the segmented target medical image(s) to create a radiodensity distribution of tissue within the segmented region or area (block 2110). In instances where segmentation is not performed, the soft tissue engine 440 creates a radiodensity distribution for the entire target medical image(s). In some embodiments, the soft tissue engine 440 may create a distribution for only pixels within a certain predefined radiodensity range (e.g., −150 HU to 150 HU or −100 HU to 100 HU). The soft tissue engine 440 then analyzes the radiodensity distribution to locate or identify a soft tissue peak (block 2112). The soft tissue engine 440 may also determine information related to the soft tissue peak, such, as for example, standard deviations or muscle tissue area (block 2114).

The soft tissue engine 440 stores the soft tissue peak and related information to a nutritional status record 618. In addition, the soft tissue engine 440 uses at least some of the information in the record 618 to determine and/or evaluate a nutritional status of the patient (block 2116). The nutritional status may be a numerical indicator, a textural indicator, or more generally, a radiodensity value of the soft tissue peak. The soft tissue engine 440 stores the nutritional status of the patient to the record 618. Further, the soft tissue engine 440 transmits the record 618, or more generally, the nutritional status of the patient in one or more message 414 to, for example, the nutritional analysis engine 442, the HIS 450, the EMR server 426, the clinician device 424, and/or the pharmacy preparation system 420. The example procedure 2100 may then return to block 2102 for the next patient.

k. Example Results

Figures 22, 23:
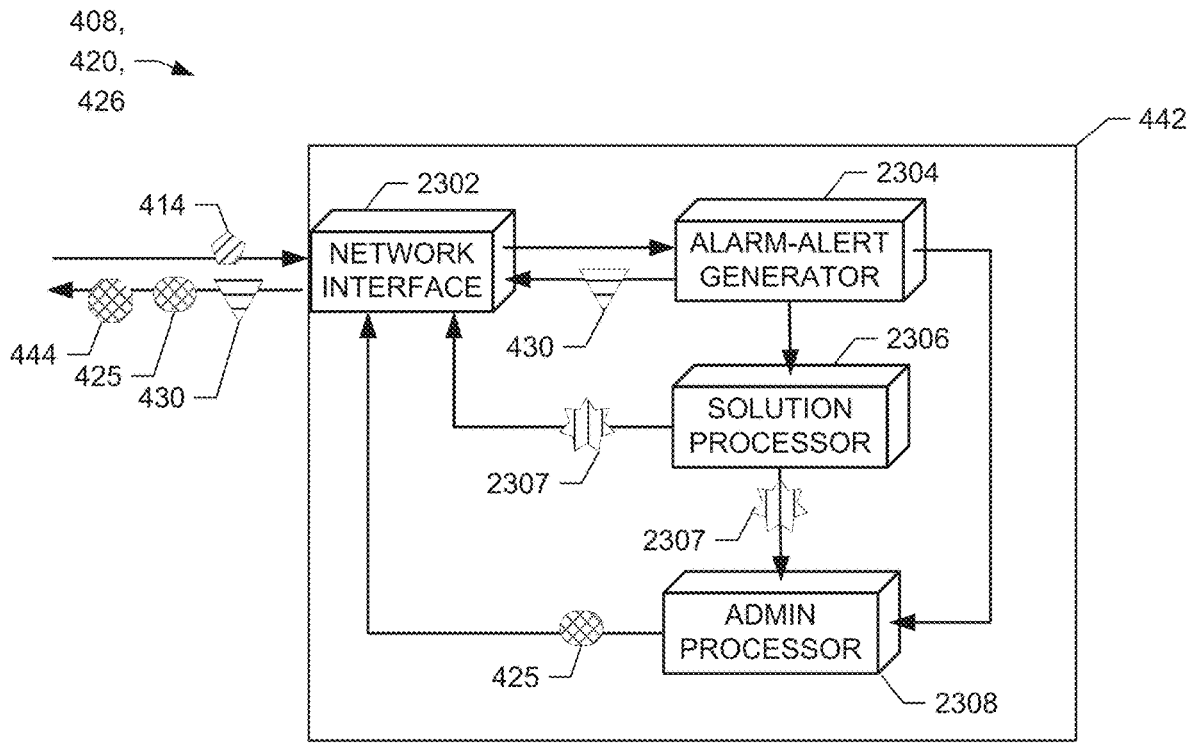
FIG. 22 illustrates a diagram of a table illustrating muscle quality experimental results using the soft tissue engine of FIG. 6, according to an example embodiment of the present disclosure.
FIG. 23 illustrates a diagram of a nutritional analysis engine that operates in conjunction with the analysis server of FIGS. 4 and 5, according to an example embodiment of the present disclosure.

FIG. 22 shows a diagram of a table 2200 illustrating experimental results using the soft tissue engine 440 described in conjunction with FIGS. 4 to 21, according to an example embodiment of the present disclosure. In an experiment, CT medical images from seventy-six different patients were analyzed to determine muscle quality and quantity. The patients had an average age of 64.3 years, with a standard deviation of +/−11.4 years. Thirty-two of the patients were male and forty-four of the patients were female. The CT images were acquired by scanning a mid-section of each of the patients.

As a control, the medical images for each patient were manually reviewed to search for a slice that represents an area between the L3 and L4 vertebrae. A technician then manually segmented the psoas muscle tissue. The segmented muscle tissue was analyzed to determine a soft tissue peak. Through this manual method, it was determined that, on average, the patients have 15.6 cm$^2$ of psoas muscle surface area, with a standard deviation of 5.7 cm$^2$. This translates into about 2927+/−997 pixels. The average soft tissue peak for these patients was determined to be about 42 HU+/−8 HU.

Next, the same medical images were analyzed using the soft tissue engine 440. For each patient, the soft tissue engine 440 automatically determined a target image for analysis using bone tissue radiodensity data. In a first run, the images were not segmented. It was determined for the first run that there was an average total tissue surface area of 262.3+/−69.5 cm$^2$ in each image. This corresponds to a total pixel count of 49,365+/−12,593 pixels. The average soft tissue peak determined from the entire images for the first run was calculated to be about 39.9+/−10.1 HU.

In a second run, the targeted medical images were segmented using a center-of-mass iterative routine. The segmented region-of-interest had an average area of 39.7+/−9.3 cm$^2$. This corresponds to about 8,397+/−1,278 pixels in the region of interest. The tissue within the segmented region-of-interest had an average soft tissue peak of 42+/−10.2 HU.

In reviewing the results, it was determined that segmentation produced a result that is closer to the manual method of quantifying muscle tissue. However, there was slightly more variability in the segmentation run compared to the manual counting. This variability may have resulted from a more precise quantification of muscle and transitional tissue pixels using an automated approach. While analyzation of the full image in the first run produced a lower soft tissue peak, the closeness of the peak to the manual method indicates that this method may also be acceptable in practice, with no computational processing needed for segmenting. The data from the first run corresponds to overall tissue composition since the analyzed image included more fat or muscle infiltrated with fat tissue (having a lower radiodensity) compared to images that were manually or automatically segmented specifically on the psoas muscle. The experiment accordingly illustrated that the soft tissue engine 440 is capable of automatically determining muscle quality and quantity to determine a nutritional status of a patient.

II. Medical Application Embodiments

There are a number of medical applications that can incorporate a patient's determined nutritional status to improve outcomes or reduce risk of complications. The sections below provide examples of medical applications that can incorporate a patient's nutritional status or quantification of muscle mass. Examples discussed below include oncology assessment, oncology treatment, pre-procedural treatments, post-procedural treatments, and nutritional therapy administration location determinations. In addition, it should be appreciated that a patient's nutritional status and/or muscle quality may be used in other applications including disease management.

a. Oncology Assessment Example

When a patient has the unfortunate diagnosis of having cancer, a physician typically performs an outcome analysis to determine the patient's prognosis five years out. Typical prognosis includes considering the patient's age, overall health, cancer type, and stage of the cancer. Each assessment includes a cancer c-statistic that assigns a probability to the prognosis. Such information is used by the physician and patient in evaluating treatment options. Generally, cancer prognoses have a c-statistic that is between 60% and 75%. This mid-range percentage means that any given prognosis is more likely than not to be correct, but leave significant room for deviation. This is why there are stories of patients being told they have 1 year or less to live only to have the patients end up living a number of meaningful years.

The example analysis server 408 and/or a clinician may use a patient's nutritional status, muscle quality, and/or soft tissue peak information to determine a more accurate prognosis. For instance, patients with healthier muscle tend to respond better to cancer treatments. In comparison, patients with muscle infiltrated with fat tend to respond less well to cancer treatments. The analysis server 408 and/or a clinician may use the patient's nutritional status to improve the value of the c-statistic. In other words, knowing the muscle quality of a patient improves the probability of the prognosis being correct. In some examples, knowing a patient's nutritional status generated c-statistics around 90%. The muscle quality and/or nutritional status may accordingly be used to improve the reliability of patient cancer assessments.

b. Oncology Treatment Example

Typical oncology treatments, such as chemotherapy, infuse medications into a patient. The medications are oftentimes water-soluble or fat-soluble. Water-soluble medications are absorbed by muscle tissue. A volume of medication distribution is determined based on a patient's estimated lean body mass or body surface area, which take into account a patient's height and weight. Known calculations of medication distribution assume that every patient has a constant distribution between fat tissue and muscle tissue based on their height and weight. However, as discussed above, patients do not have the same muscle-to-fat ratios. Some patients, especially older patients, have muscle degeneration.

The differences between muscle-fat ratios for patients mean that patients will absorb different amounts of chemotherapy medication differently. For example, two patients may have identical, or very similar, heights and weights. However, one of the patients may have healthy muscle while the other patient has significant muscle degradation. Since the patients have the same height and weight, known calculations would recommend the same chemotherapy dosage for each patient. However, the unhealthy patient has less muscle mass to absorb the medication. This means that the muscle that is there absorbs more of the medication than intended. The result is that muscle of the unhealthy patient has higher concentrations of the medication. If the concentrations exceed certain levels, it is considered an overdose that results in a risk of the patient experiencing affects from toxicity. By comparison, the healthy patient has more muscle to absorb the same dosage of medication, which means lower concentrations of the medication per square centimeter of muscle.

The example analysis server 408 and/or a clinician may use a patient's nutritional status, muscle quality, and/or soft tissue peak information to determine that a lower (or higher) dosage of chemotherapy medication may be more beneficial. For instance, the analysis server 408 may determine that patients with less muscle mass are to be prescribed 10% to 20% less chemotherapy medication than otherwise recommended to avoid toxicity. In other examples, the analysis server 408 may provide an alert and/or alarm to a clinician indicating that the chemotherapy dosage should be revisited in view of a patient's muscle mass and/or nutritional status. The muscle quality and/or nutritional status may accordingly be used to improve chemotherapy treatment.

c. Pre-Procedural and Post-Procedural Examples

Oftentimes before undergoing an intensive medical procedure, such as abdominal surgery or aortic heart valve replacement, or beginning treatment for a disease, a clinician prescribes or recommends actions that a patient may take to improve the outcome. This includes exercising, eating healthy, and refraining from smoking and drinking. The example analysis server 408 and/or a clinician may use a patient's nutritional status, muscle quality, and/or soft tissue peak information to determine if a patient is to be prescribed a nutritional therapy before, during, or after a procedure or disease treatment to further improve a patient's outcome.

Currently, ASPEN recommends that a nutritional therapy is not to be administered until at least 7 to 14 days after a patient cannot feed themselves or after a medical procedure. During this time, the patient's metabolism increases to help the patient recover from the procedure or treatment. In addition, any inflammation from the procedure or treatment usually consumes muscle tissue and leads to fat infiltration. This means that today malnourished patients or patients that become malnourished are not given nutritional therapy until at least a week after a procedure. This delay enables the malnutrition to become worse, thereby slowing the patient's metabolism and ability to recover.

The example analysis server 408 and/or a clinician may use a patient's nutritional status, muscle quality, and/or soft tissue peak information to determine whether (and how much) nutritional therapy is needed based on a patient's degree of malnourishment. For example, during an initial assessment, in addition to recommending that a patient exercise, the analysis server 408 and/or a clinician may determine from a patient's nutritional status that the patient is to undergo some level of nutritional therapy. This could include a nutritional supplement consumed orally and/or provided subcutaneously, enterally, and/or parenterally. The goal is to establish a patient's nutritional status to enable proper nutritional treatments to be proactively prescribed to reduce changes of developing complications later.

To determine a nutritional therapy, the analysis server 408 may compare the patient's demographics, disease state, and nutritional status to population data. The analysis server 408 may determine potential outcomes based on medical histories of similarly situated patients. If the potential outcomes result in complications or low levels of recovery associated with malnourishment, the analysis server 408 may determine that the patient is to receive a nutritional therapy. The parameters of the therapy may be recommended based on a soft tissue peak in conjunction with the procedure, disease state, and patient demographics.

In addition, the analysis server 408 may also determine or recommend post-procedural care based on the nutritional status and/or muscle mass of the patient. For example, the analysis server 408 may recommend ICU care or nursing home care for patients with severe malnourishment. In contrast, the analysis server 408 may recommend at-home care for patients with moderate malnourishment. Such recommendations may be determined before the procedure, such that the clinician and patient are aware of most likely post-procedural care options and post-procedural quality of life. The nutritional information may also enable the clinician and/or patient to prearrange and take appropriate measures to setup this care. Accordingly, knowing a patient's nutritional status enables clinicians to be more proactive to help patients avoid (or reduce the effects from) post-procedural complications.

d. Nutritional Therapy Administration Location Determination Examples

In many instances, a patient may be prescribed a nutritional treatment that is not administered parenterally. For example, nutrition may be provided subcutaneously without an IV or catheter. Additionally, nutrition may be administered orally through a supplement. The example analysis server 408 may be configured to provide an administration location recommendation and/or determination based on a patient's nutritional status, muscle mass, disease state, and/or demographic information. For example, the analysis server 408 may determine that moderately malnourished patients may be prescribed a subcutaneous treatment where nutrition is provided underneath a patient's skin. While subcutaneous treatment cannot match parenteral or enteral in terms of the volume of nutritional solution that can be administered, it is significantly less invasive and may be administered by a less skilled profession in a patient's home or nursing home.

In other examples, the analysis server 408 may analyze population data to determine anticipated discharge conditions of patients similarly situated to the patient under analysis. The analysis server 408 determines, for example, that patients with the same demographics and disease state typically require a stay in the ICU for at least three days before regaining the ability to feed themselves. The analysis server 408 may recommend a nutritional therapy, such as parenteral or enteral, which can more easily be administered in the ICU. Accordingly, knowing a patient's nutritional status enables clinicians to be more proactive in determining how a nutritional therapy is to be administered.

III. Nutritional Therapy Component Embodiment

In some embodiments, alarms, alerts, and/or a recommendation may be generated based on a patient's nutritional status determined by the nutritional status diagnostic component 402. In addition, nutritional therapy parameters and/or components of a nutritional solution may be determined and/or recommended based on a patient's nutritional status in conjunction with other information, such as patient demographic information, physiological information, disease state, etc. The example nutritional therapy component 404 of the medical environments 400 of FIGS. 4 and 5 is configured to automatically manage the administration of a nutritional therapy to a patient based, at least in part, on a patient's determined nutritional status. The nutritional therapy component 404 includes the nutritional analysis engine 442, which may be configured to use the patient's nutritional status, soft tissue peak, and/or related soft tissue peak information in the nutritional status record 618 (and/or the distribution data 612) to determine a nutritional therapy for a patient. The nutritional analysis engine 442 may be located in and/or operate in conjunction with the analysis server 408, the EMR server 426, and/or the pharmacy preparation system 420.

Referring again to FIGS. 4 and 5, the nutritional therapy component 404 in the illustrated embodiments of FIGS. 4 and 5 includes one or more infusion pumps 422. The example infusion pump 422 may include any pump capable of delivering an intravenous and/or nutritional (e.g., a total parenteral nutrition ("TPN")) therapy to a patient via one or more line sets. Examples include a syringe pump, a linear peristaltic pump, a large volume pump ("LVP"), an ambulatory pump, multi-channel pump, etc. A syringe pump uses a motor connected to a drive arm to actuate a plunger within a syringe. A linear peristaltic pump uses a rotor to compress part of a tube while rotating. Oftentimes, one or more rollers of the rotor contact the tube for half a rotation. The compressed rotation causes a defined amount of fluid to pass through the tube. LVPs typically use one or more fingers or arms to compress a portion of intravenous therapy ("IV") tube. The timing of the finger actuation on the tube causes constant or near constant movement of a fluid through the tube.

The example infusion pump 422 may include, for example, the Baxter® SIGMA Spectrum™ pump, which is shown in FIGS. 4 and 5. The infusion pump 422 includes a display 451 and interfaces 452 that enable a clinician to specify or program an infusion or nutritional therapy. The display 451 may present a graphical code (e.g., a quick response ("QR") code, which may be scanned by a clinician to associate the pump 422 with a nutritional therapy pump prescription message 425 at the EMR server 426, the pharmacy preparation system 420, and/or the analysis server 408. The interfaces 452 may be configured to enable a clinician to program parameters from a nutritional therapy pump prescription message 425 into the pump 422. Other examples of infusion pumps include a linear volume parenteral pump described in U.S. Publication No. 2013/0336814, a syringe pump described in U.S. Publication No. 2015/0157791, an ambulatory infusion pump described in U.S. Pat. No. 7,059,840, an infusion pump described in U.S. Pat. No. 5,395,320, and an infusion pump described in U.S. Pat. No. 5,764,034, the entirety of each are incorporated herein by reference. The infusion pump 422 may also include the Baxter® Colleague™ volumetric infusion pump.

The example pharmacy preparation system 420 includes any system that is configured to manage and prepare compound solutions (e.g., TPN solutions and other multi-ingredient solutions) for administration to a patient. For example, the pharmacy preparation system 420 may include the Baxter® EXACTAMIX™ Compounder, which is an automated pumping system that compounds multiple sterile ingredients into a finished solution in one or more patient bags. The pharmacy preparation system 420 may produce, for example, a three liter patient-ready TPN bag in approximately four minutes once an individual patient formula has been determined. Preparation includes, for example, creating a nutritional solution by selecting and mixing together certain quantities of water, amino acids, lipids, glucose, dissolved salt, triglycerides, trace elements, vitamins, and/or nutritional supplements. In some instances, the pharmacy preparation system 420 may also select a premixed solution (or modify a premixed solution) among a plurality of available premix solutions such at the Clinimix™ and Clinimix E™ manufactured by Baxter®.

The example pharmacy preparation system 420 may also include a pharmacy workflow manager 460 that is configured to automate the process of routing, preparing, inspecting, tracking, and reporting on the preparation of nutritional solutions prepared by the compounder. In some embodiments, the pharmacy workflow manager 460 may include the DoseEdge™ Pharmacy Workflow Manager, provided by Baxter®. The nutritional analysis engine 442, or components of the nutritional analysis engine 442, may be included within the pharmacy workflow manager 460. For instance, after determining (or receiving an indication) that a patient is to receive a TPN therapy, the nutritional analysis engine 442 at manager 460 may determine administration parameters to program the infusion pump 422 and/or components, compositions, and/or concentrations for a TPN solution. The administration parameters may be provided to the pump 422 in a nutritional therapy pump prescription message 425.

The example nutritional analysis engine 442 is configured to analyze a nutritional status of a patient to determine if one or more alarm(s) or alert(s) is to be generated. The alarms or alerts may be sent to the clinician device 424 to place a clinician on notice about the patient's nutritional status. A clinician may accordingly use the clinician device 424 to prescribe a nutritional therapy. The alarms or alerts may also be sent to the EMR server 426, which may prevent, or at least generate a warning in regard to, a subsequent medical procedure. The nutritional analysis engine 442 may further use information associated with the nutritional status and/or patient demographic information to determine (or recommend) a nutritional therapy. This may include, for example, determining (or recommending) administration parameters, such as a volume to be infused, an infusion rate, and/or an infusion duration. This may also include determining (or recommending) components of a nutritional solution.

FIG. 23 shows a diagram of the nutritional analysis engine 442 of FIGS. 4 and 5, according to an example embodiment of the present disclosure. The blocks shown in FIG. 23 may be implemented as software modules, applications, algorithms, and/or routines operating within the nutritional analysis engine 442. It should be appreciated that some of the blocks may be combined and/or omitted. Further, some of the blocks may be implemented in different physical locations on the analysis server 408. For instance, the analysis server 408 may include blade servers or processors distributed across a computing environment such as a cloud computing environment. The nutritional analysis engine 442 may also be distributed across one or more devices in the nutritional therapy component 404, including the analysis server 408, the EMR server 426, and/or the pharmacy preparation system 420. Accordingly, each of the blocks shown in FIG. 23 may be implemented or operated by separate (or the same) processors. Moreover, separate instances of each of the blocks may be initiated for each record 618 and/or each patient.

a. Network Interface

The example nutritional analysis engine 442 of FIG. 23 includes a network interface 2302 to receive, for example, messages 414 including the nutritional status records 618. In some instances, the network interface 2302 may be addressable to receive the messages 414. In other examples, the network interface 2302 may subscribe at a gateway (located at or configured to operate in conjunction with the EMR server 426 and/or the HIS 450) to receive messages 414 that include the nutritional status records 618. In various examples, the messages 414 may include a certain identifier in a header that provides an indication of the type of the message. To receive the messages 414, the network interface 2302 in one embodiment requests for the gateway to send the messages 414 with the certain identifier. The network interface 2302 may also subscribe based on a patient identifier. In alternative embodiments, the network interface 2302 may poll, for example, the soft tissue engine 440 and/or the EMR server 426 requesting newly created nutritional status records 618.

In some examples, such as when the nutritional analysis engine 442 is part of the pharmacy preparation system 420, the network interface 2303 may receive prescription information from the clinician device 424 and/or the EMR server 426. For instance, a clinician may determine that a patient is malnourished through information in the record 618. In response, the clinician may create a nutritional prescription at the clinician device 424, which is sent to the network interface 2302 and/or the EMR server 426. The nutritional analysis engine 442 uses the information within the prescription in conjunction with the pharmacy preparation system 420 to create a nutritional solution and/or create administration parameters to auto-program the infusion pump 422 via the nutritional therapy pump prescription message 425.

The example network interface 2302 is also configured to transmit information to other devices within the nutritional therapy component 404. For instance, the network interface 2302 may transmit, in one or more message(s) 444 (such as HL7 compliant messages), parameters of a nutritional therapy and/or components of a nutritional solution. The transmission may include, for instance, a nutritional therapy pump prescription message 425. The messages 444 and/or 425 may be transmitted to the pharmacy preparation system 420, which cause the system 420 to prepare one or more nutritional solutions. The messages 444 and/or 425 may also be transmitted to the infusion pump 422 for auto-programming. The messages 444 and/or 425 may also be transmitted to the clinician device 424 and/or the EMR server 426 for documentation and review.

The network interface 2302 may also transmit alerts and/or alarms in one or more messages 430. For instance, after it is determined that an alert and/or alarm is to be transmitted, the network interface 2302 may identify recipients for the messages 430. Recipients may include clinician devices 424 that have subscribed to receive alarms and/or alerts regarding the nutritional status of patients and/or clinician devices 424 that have subscribed to receive alarms and/or alerts related to certain patients. The network interface 2302 may also transmit the alarms/alerts to the EMR server 426 for documentation. In some instances, the transmission of the alarms/alerts to the clinician devices 424 may be provided by the EMR server 426 after receiving the alarms/alerts from the network interface 2302. In some instances, sending the messages 430 to the EMR server 426 may cause a notification to be generated by the EMR server 426 that a subsequent medical procedure should be delayed until the patient receives a nutritional therapy. The messages 430 may also cause the EMR server 426 to prevent, as much as possible, a subsequent medical procedure from being performed until the patient's malnutrition is treated.

The network interface 2302 may also transmit the messages 430 to the pharmacy preparation system 420 in instances where the nutritional analysis engine 442 is located at the EMR server 426 and/or the analysis server 408. The messages 430 may provide an indication to a pharmacy technician that a nutritional solution is to be prepared. The messages 430 may also prompt a pharmacist or a clinician to determine a nutritional therapy based on the information within the nutritional status record 618, the patient's demographic traits, a subsequent medical procedure, and/or a patient's disease/injury/condition.

b. Alarm-Alert Generator

The example nutritional analysis engine 442 of FIG. 23 includes an alarm-alert generator 2304 configured to determine if an alarm and/or alert is to be created based on information within the nutritional status record 618 and/or the distribution data 612. The example alarm-alert generator 2304 is configured to analyze information within, for example, the nutritional status record 618 using one or more routines and/or algorithms to determine if an alarm and/or an alert is to be generated. In some embodiments, the alarm-alert generator 2304 may also use patient demographic data, population data, medical history data, and/or physiological data in conjunction with the muscle quality and/or quantity data in the record 618 to determine if an alert and/or alarm are to be generated. Moreover, the alarm-alert generator 2304 may also consider the patient's disease state, care area, and/or subsequent scheduled medical procedures to determine whether an alarm and/or an alert are to be generated.

To determine if an alarm and/or alert is to be generated, the alarm-alert generator 2304 may be configured to access certain data from external sources, such as the EMR server 426. For instance, the alarm-alert generator 2304 may access the EMR server 426 to access a patient's EMR, which may include medical history, demographic data, physiological data, and/or medical procedure schedule. To access a specific record, the alarm-alert generator 2304 may transmit in a request message a patient identifier, which was included within the messages 414, to the EMR server 426. In response, the alarm-alert generator 2304 receives the requested patient EMR (or specific requested portions of the EMR). In other embodiments, the information for determining if an alarm and/or alert is to be generated may be included within the received messages 414.

An alert is an indication that a clinician should review a patient's nutritional condition based on the determined nutritional status. In other words, an alert provides an advisory notice that a nutritional therapy may be warranted for the patient. In many cases, an alert may be overridden by a clinician such that a nutritional therapy is not needed. However, in some cases, the clinician may decide to proceed with a nutritional therapy. In some embodiments, the nutritional analysis engine 442 may wait for confirmation from a clinician before automatically determining solution components and/or pump administration parameters.

In comparison to an alert, an alarm is indicative that a clinician is required to review a patient's medical condition based on the determined nutritional status. In many cases, generation of an alarm requires a patient to undergo a nutritional therapy, if the situation warrants, unless specific overriding instructions are received from a clinician. After generating an alarm, the nutritional analysis engine 442 may begin determining a solution composition and/or administration parameters. In other instances, the nutritional analysis engine 442 may be configured to wait for a prescription or order from a clinician. In these other instances, the nutritional analysis engine 442 may periodically transmit the alarm or elevate the status of the alarm until a response is received. Moreover, generation of the alarm may prevent a patient from undergoing a subsequent medical procedure until the alarm is addressed.

To generate an alarm and/or an alert the alarm-alert generator 2304 is configured to generate one or more message(s) 430, which is indicative of the alarm and/or the alert. The message 430 may be HL7 compliant and include, for example, a creation time/date, a patient identifier, and a code or text indicative of why the alarm and/or alert was generated. The messages 430 may also include options for responding, including a link selectable by a clinician using the device 424 to create a nutritional prescription. The messages 430 may further include at least some of the information from the record 618 and/or the distribution data 612. For instance, the messages 430 may include a nutritional status value, a soft tissue peak, muscle surface tissue area, and/or a link to a target medical image 609 (or the image itself).

Figure 24:
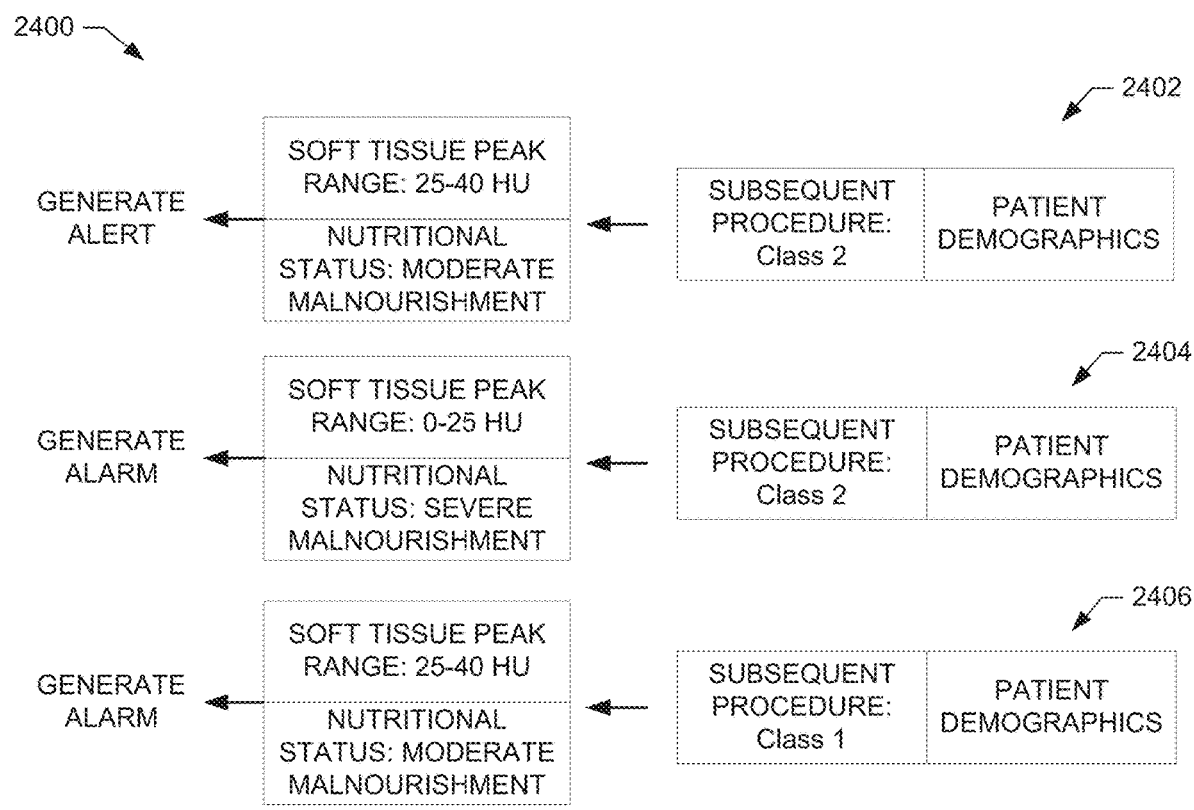
FIG. 24 illustrates a diagram representing an example algorithm that is executable by the nutritional analysis engine of FIG. 23 to determine whether an alarm and/or an alert are to be generated based on muscle quality data and/or muscle quantity data, according to an example embodiment of the present disclosure.

FIG. 24 shows a diagram illustrative of an example algorithm 2400 executable by the alarm-alert generator 2304 to determine whether an alarm and/or an alert are to be generated based on muscle quality data and/or muscle quantity data, according to an example embodiment of the present disclosure. The algorithm 2400 is only exemplary of routines and/or algorithms that may be used by the alarm-alert generator 2304. In other examples, the algorithm 2400 may include additional factors, such as physiological data, population data, care area, and patient history data. In yet other examples, the algorithm may include fewer factors, such as using only a determined soft tissue peak and/or nutritional status of a patient.

The algorithm 2400 illustrated in may FIG. 24 include three different conditions 2402, 2404, and 2406 for generating an alarm and/or alert. Condition 2402 specifies that an alert is generated when (i) a soft tissue peak radiodensity value is between 25 and 40 HU and/or a nutritional status indicates 'moderate' malnourishment, and (ii) a subsequent procedure has a classification that is no higher than class 2. In some embodiments, medical procedures may be assigned a class based on patient risk, substantiality, and/or invasiveness. More intensive procedures correspond to a lower number. A class 2 procedure may include moderate surgery, such as an ACL repair or joint repair. In comparison, a class 1 procedure may include chemotherapy, extensive surgery (such as abdominal surgery), or significant trauma-related surgery. In instances where no subsequent medical procedure is scheduled, the algorithm 2400 may be based on a patient's current disease state or condition.

In some examples, the algorithm 2400 may also be configured to consider patient demographics. For example, the soft tissue peak range may be adjusted based on a patient's age and/or gender. The adjustment may account for natural muscle degradation of normal individuals with similar to reduce the generation of false alerts. For instance, the algorithm 2400 may shift the range downward by 1 HU for every five years the patient is over 40 or 45 years old. Further, the range may be adjusted based on whether the patient is male or female, where slightly lower ranges may be used for females. In instances where muscle tissue surface area is considered when generating an alert, the algorithm 2400 may be configured to adjust thresholds based on a patient's height. Typically, taller patients have more muscle tissue. To account for this, the algorithm 2400 may normalize muscle tissue area based on height.

Conditions 2404 and 2406 specify when an alarm is to be generated. For condition 2404, the algorithm 2400 may determine that an alarm is to be generated when (i) a soft tissue peak radiodensity value is between 0 and 25 HU and/or a nutritional status indicates 'severe' malnourishment, and (ii) a subsequent procedure has a classification that is no higher than class 2. For condition 2406, the algorithm determines that an alarm is to be generated when (i) a soft tissue peak radiodensity value is between 25 and 40 HU and/or a nutritional status indicates 'moderate' malnourishment, and (ii) a subsequent procedure has a classification that is no higher than class 1. The difference between conditions 2404 and 2406 lies with the classification of the subsequent medical procedure. In condition 2406, since the subsequent medical procedure is a more intensive class 1 procedure, the threshold for generating an alarm is much lower (e.g., the soft tissue peak range only has to be between 25 HU and 40 HU). In other words, the algorithm 2400 provides a more critical response with an alarm to ensure sure a patient has sufficient amino acid reserves prior to undergoing a more substantive medical procedure (or is afflicted with a more severe condition or disease).

After determining that an alarm or alert is to be generated, the example alarm-alert generator 2304 of FIG. 23 is configured to generate one or more message(s) 430 indicative of the alarm and/or alert. The message(s) 430 are transmitted to the network interface 2302 for transmission to the appropriate devices 420, 424, and 426. Additionally, the alarm-alert generator 2304 is configured to begin the process of determining a solution composition and/or administration parameters, which are described in more detail below.

c. Solution Processor

The example nutritional analysis engine 442 of FIG. 23 includes a solution processor 2306 configured to determine a composition, components, and/or concentration of a nutritional solution based, for example, on a nutritional status of a patient. The example solution processor 2306 is configured to determine a solution composition after receiving an indication from the alarm-alert generator 2304. Additionally or alternatively, the solution processor 2306 may be configured to receive a message from the EMR server 426 and/or the clinician device 424 providing an indication that a nutritional solution is to be prepared. The indication may include an approval for the solution processor 2306 to determine or recommend a nutritional solution. The indication may also include a nutritional therapy prescription or order that may specify, for example, a total amount of nutrition to be administered, a desired level of amino acids, lipids, and/or glucose to be administered, and/or a type or name of a nutritional solution to be administered.

In instances where the prescription or order specifies certain properties or parameters, the solution processor 2306 is configured to check the values of the properties or parameters against a drug library or nutrition library. The solution processor 2306 may generate an alert and/or an alarm if any of the values exceed library limits. For instance, the solution processor 2306 may receive an order that specifies 200 grams ("g") of amino acids are to be provided for every liter ("l") of solution. However, the nutrition library may include a limit of 125 g/l. In response to determining that value of the amino acid parameter exceeds a limit, the solution processor 2306 transmits an alert and/or an alarm to the clinician device 424. In response, the clinician may revise the order or override the limit.

In some examples, the solution processor 2306 may receive parameters or a prescription order that provides more general parameters, such as a total volume of solution to be infused. In these examples, the solution processor 2306 may use one or more of the routines or algorithms discussed below to determine a composition of amino acids, lipids, and/or glucose based on the muscle quality and/or quantity data within the nutritional status record 618 and/or the distribution data 612. In addition, the solution processor 2306 may use one or more demographic traits of the patient, such as height, weight, and/or gender to refine the solution composition determination. Further, the solution processor 2306 may use the disease state/condition, care area, population data, and/or physiological parameters to refine the solution composition determination.

The example below discloses one example routine and/or algorithm that the solution processor 2306 may execute to determine a solution composition for a patient. Initially, the solution processor 2306 is configured to determine an ideal body weight ("IBW") in kilograms ("kg") for a patient using the patient's height in centimeters. For instance, the solution processor 2306 may use equation (1) below for a male patient and equation (2) below for a female patient to determine an IBW.

$$IBW_{male} = 48 + (height - 152) * 1.06 \quad (1)$$

$$IBW_{female} = 45.4 + (height - 152) * 0.89 \quad (2)$$

The example solution processor 2306 is configured to determine a base dosing regimen or total volume of solution to be infused per day based on the IBW. For instance, a routine may correlate or equate patient height and/or IBW to a base level of solution to be administered. In an example, an IBW of 85 kg corresponds to a base solution of 2400 ml, an IBW of 75 kg corresponds to a base solution of 2100 ml, an IBW of 65 kg corresponds to a base solution of 1800 ml, an IBW of 55 kg corresponds to a base solution of 1500 ml, and an IBW of 45 kg corresponds to a base solution of 1200 ml.

After determining the base amount of solution, the example solution processor 2306 is configured to adjust the base solution according to muscle quality and/or quantity data. In some examples, the radiodensity of the soft tissue peak may be used. In other examples, the surface area of the muscle tissue and/or a standard deviation of the soft tissue peak may be used. Equation (3) below shows can example adjustment that may be applied to the base solution volume. In the example below, constant value '45' is subtracted from the radiodensity value of the soft tissue peak ("STP"). The difference is then divided by a normalization constant (f), which may include any value between 30 and 100 based, for instance, on determined correlations between soft tissue peak and treatments for malnutrition. This result, referred to as the adjustment, is then multiplied by the base solution volume and added to the base solution amount to determine an adjusted solution amount. In other words, the adjustment corresponds to a percentage increase in the base solution volume.

$$\text{adjustment} = \frac{45 - STP}{f} \quad (3)$$

In an example, a patient with an IBW of 75 kg has a soft tissue peak with a radiodensity value of 37 HU, which corresponds to moderate malnutrition. In this example, f has a value of '60'. The base solution volume for the patient is 2100 ml based on the 75 kg IBW. The solution processor 2306 uses equation (3) to determine that the base amount has to be increased by 13.3%. The solution processor 2306 accordingly determines that the patient is to receive 2380 ml of nutritional solution to treat the patient's moderate malnourishment.

After determining a total solution to be administered per day, the example solution processor 2306 determines an amount of amino acids, lipids, and/or glucose to be included within the solution. It should be appreciated that the solution processor 2306 may be configured to create nutritional solutions that are relatively rich in amino acids to help restore a patient's amino acid reserves. In the above-example, the amount of amino acids to be provided in the nutritional solution ranges from 50 g/l to 83 g/l. Additionally, the amount of glucose ranges from 67 g/l to 112 g/l and the amount of lipids ranges from 17 g/l to 30 g/l. To determine the amounts of each component, the solution processor 2306 may make an adjustment similar to the adjustment described in connection with equation (3). For example, equation (4) may be used by the solution processor 2306.

$$\text{adjustment} = \frac{45 - STP}{c} \quad (4)$$

Similar to equation (3), equation (4) subtracts the soft tissue radiodensity from 45 HU. The difference is then divided between normalization constant (c), which may be any value between 10 and 100. In some instances, the normalization constant c may be one-half the value off. For instance, in the example discussed above in connection with equation (3), the constant f has a value of 60. Accordingly, the constant c is 30. For the same patient, the adjustment for amino acid content is determined to be 26.6%, which is applied to the base amino acid amount of 50 g/l. The solution processor 2306 accordingly determines that the patient is to receive 63.3 g/l of amino acids in the solution. Since the patient is to receive 2380 ml of solution per day, this means that the solution is to comprise a total of 150 g (2.380 l*63.3 g/l) of amino acid per day.

It should be appreciated that the solution processor 2306 not only increases the amount of solution administered to a patient, but also the concentration of amino acids in the solution as a patient is more severely malnourished. Such a configuration may reduce a total number of days of nutritional therapy needed since the patient is receiving a relatively high level of amino acids. In alternative embodiments, the solution processor 2306 may maintain the total solution volume but increase the concentration of amino acids. These alternative embodiments may be used for patients that cannot handle larger volumes of solution but still need an increased dose of amino acids.

The example solution processor 2306 may perform similar calculations for the glucose and lipid components. It should be appreciated that the adjustment is applied to the base amount for each (67 g/l for glucose and 17 g/l for lipids). Further, different normalization constants may be used for lipids and glucose since these components may not be as critical to the patient as amino acids. In other examples, the glucose and lipid amounts may be specified as ratios to the concentration of amino acid such that the determined amount of amino acid may be used to determine the amount of lipids and glucose. In yet other examples, the routine or algorithm used by the solution processor 2306 may specify a table that correlates amino acid concentration to lipid and glucose concentrations.

Once the amount of amino acid, lipids, and glucose are determined, the example solution processor 2306 may determine specific component compositions to generate the determined quantities of amino acids, lipids, and glucose. For instance, the routine or algorithm may specify that to generate 50 g/l of amino acids, a solution should be prepared containing 5 g of isoleucine, 7.4 g of leucine, 9.31 g of lysine acetate (corresponding to 6.6 g of lysine), 4.3 g of methionine, 5.1 g of phenylalanine, 4.4 g of threonine, 2 g of tryptophan, 6.2 g of valine, 12 g of arginine, 3 g of histidine, 14 g of alanine, 11 g of glycine, 11.2 g of proline, 6.5 g of serine, 0.4 g of tyrosine, and 1 g of taurine. The solution processor 2306 is configured to adjust these amounts based on the adjusted amount of amino acid. For example, if the amount of amino acids is increased by 10%, then each of the components may be increased by 10%. Similarly for lipids, the routine or algorithm may specify that to generate 17 g/l of lipids, a solution should be prepared containing 60 g of soya oil, 60 g of MCTs, 50 g of olive oil, and 30 g of fish oil. The solution processor 2306 may be configured to adjust these amounts based on the adjusted amount of lipids.

In addition, the solution processor 2306 may determine amounts of micronutrients to include with the nutritional solution. For instance, the solution processor 2306 may determine an amount of vitamins, trace elements, electrolytes, and/or dipeptides. Vitamins can include, for example, vitamin A, vitamin B1, vitamin B2, vitamin B3, vitamin B5, vitamin B6, vitamin B7, vitamin B9, vitamin B12, vitamin C, vitamin D, vitamin E, and vitamin K. Trace elements include, for example, chromium (Cr), cobalt (Co), iodine (I), iron (Fe), copper (Cu), manganese (Mn), molybdenum (Mo), selenium (Se), and zinc (Zn). In some instances, the solution processor 2306 may determine the amount based on a patient's sex and age, which are correlated to a daily recommended amount of the trace elements and/or vitamins. In some embodiments, the daily recommended amount may constitute a baseline. In these embodiments, the solution processor 2306 is configured to determine an adjustment to the baseline using, for example, equations similar to equations (3) and (4) above. In other examples, the solution processor 2306 may simply double (or apply some other factor to) the recommended amount.

Regarding electrolytes, the example solution processor 2306 is configured to determine types and amounts based on equations similar to equations (3) and (4) above. For instance, an algorithm or routine used by the solution processor 2306 may specify that per 1000 ml of solution to be administered, the electrolytes should include approximately 32.8 mmol of sodium to approximately 48 mmol of sodium, approximately 24 mmol of potassium to approximately 36 mmol of potassium, approximately 4.1 mmol of magnesium to approximately 6.1 mmol of magnesium, approximately 2 mmol of calcium to approximately 3 mmol of calcium, approximately 8.2 mmol of phosphate to approximately 15.6 mmol of phosphate, approximately 0.032 mmol of zinc to approximately 0.048 mmol of zinc, approximately 4.1 mmol of sulphate to approximately 6.1 mmol of sulphate, approximately 28.8 mmol of chloride to approximately 43.2 mmol of chloride, and approximately 84.8 mmol of acetate to approximately 127.2 mmol of acetate.

Regarding dipeptides, the example solution processor 2306 is configured to determine types and amounts of dipeptides based on equations similar to equations (3) and (4) above. For instance, an algorithm or routine used by the solution processor 2306 may specify that per 1 ml of solution to be administered, the dipeptides should include 0.01 g to 0.04 g of dipeptides.

The example solution processor 2306 of FIG. 23 may determine that the nutritional solution is to be prepared in one or more packets or bags. In some embodiments, the solution processor 2306 may determine that the amino acid, glucose, and lipid components are to be included within the same bag. In other examples, the solution processor 2306 may determine or recommend that each of the amino acid, glucose, and lipid components are to be included in a separate bag. The determination as to whether the components are to be separated may be based on a nutritional status of a patient, where more malnourished patients may be administered separate bags.

While the above description pertains to creating a new solution, in some embodiments, the solution processor 2306 may use the muscle quality and/or quantity data to select a pre-mixed nutritional solution or select among of group of predefined formulations. In these examples, the solution processor 2306 determines an ideal amino acid concentration and/or solution volume. The solution processor 2306 then compares the ideal amino acid concentration and/or volume to a database of premix or predefined solutions. The solution processor 2306 then selects the most closely matching premix and/or predefined solution. Further, in some embodiments, the solution processor 2306 may determine a modification or supplement to apply to the premix or predefined solution. The modification or supplement is configured to make the premix and/or predefined solution more closely resemble the ideal amino acid solution. For example, the solution processor 2306 may specify a number and concentration of components or ingredients to add to a predefined solution to increase the amino acid concentration.

The example solution processor 2306 of FIG. 23 may also determine a total number of days the solution is to be administered or a total volume of solution to be administered. In some instances, the solution processor 2306 is configured to use an equation similar to equations (3) and (4) above where the soft tissue peak is used as a basis for determining a number of therapy days. In these instances, the constant may be between 0.25 and 10. Accordingly, more days are added to the therapy the further a patient's soft tissue peak is from 45 HU (or other selected radiodensity value). It should be appreciated that in the above examples, the value of '45 HU' was selected as an example reference radiodensity value. In other examples the reference may be higher or lower (e.g., 40 HU, 38 HU, 35 HU, etc.) based on one or more thresholds for malnutrition.

The example solution processor 2306 is configured to store the nutritional solution components to a solution composition record 2307. The record 2307 is transmitted in one or more messages 444 to, for example, the EMR server 426 and/or the pharmacy preparation system 420. In some instances, the pharmacy preparation system 420 is configured to prepare a nutritional solution based on the compositions specified within the record 2307. In other instances, the record 2307 may be provided as a recommendation to a clinician and/or a pharmacist. In these instances, the record 2307 may be accepted or modified before the nutritional solution is prepared.

It should be appreciated that the example solution processor 2306 may be modified or adjusted based on currently available research data and/or expert consensus/opinions/guidelines. For example, research data may determine new optimal carbohydrate/amino acid/fat doses for different body compositions in different clinical circumstances. In response, the solution processor 2306 may be updated by changing variables, constant values, and/or equations to reflect the new research data.

d. Administration Processor

The example nutritional analysis engine 442 of FIG. 23 also includes an administration processor 2308 configured to determine, for example, pump parameters for the nutritional therapy pump prescription message 425. The administration processor 2308 may be configured to generate or determine the pump parameters based, for example, on a prescription received from a clinician and/or the composition record 2307 received from the solution processor 2306. In some instances, the administration processor 2308 may receive an indication from the pharmacy preparation system 420 indicative that a specified solution has been prepared. The indication may also specify component or solution properties that are used by the administration processor 2308 to generate a prescription. In alternative embodiments, the administration processor 2308 may be located at the pharmacy preparation system 420 and generate prescription parameters for the pump prescription message 425 to program the pump 422 in conjunction with a nutritional solution being prepared.

In some embodiments, the administration processor 2308 may also access a patient's EMR for demographic data, physiological values, and/or disease/condition information. The administration processor 2308 may be configured to create pump prescription message 425 to enable the pump 422 to be automatically programmed. Accordingly, the administration processor 2308 may be configured to create one or more HL7 messages, for example, that specify pump parameter values required to program the pump 422 to perform a nutritional therapy.

Figure 25:
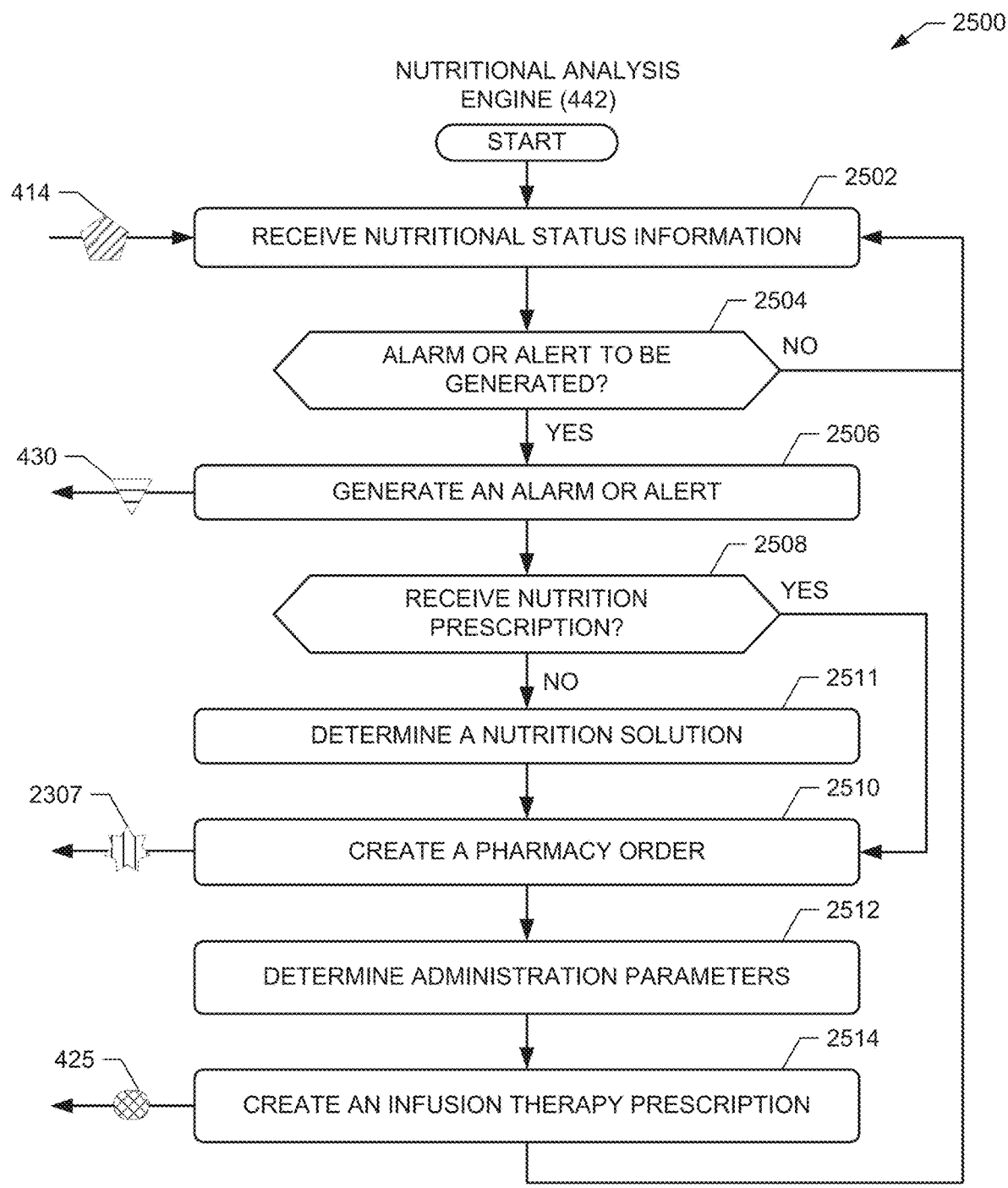
FIG. 25 illustrates a flow diagram showing an example procedure to program a nutritional infusion pump based on a patient's nutritional status, which has been determined by the soft tissue engine of FIG. 6, according to an example embodiment of the present disclosure.

The pump prescription message 425 specified by the administration processor 2308 may include, for instance, a patient identifier parameter, a patient weight parameter, a pump identifier parameter, and a date/time parameter for administration. Regarding the date/time parameter, the prescription may specify a certain duration during a day for administration (e.g., two separate six hour periods) The pump prescription message 425 may also include parameters for a name of the nutritional solution and/or identifier(s) of components within the solution, such as a concentration of amino acid. The pump prescription message 425 may further include parameters for a total volume to be infused and/or a volume to be infused per bag, container, or packet. Further, the pump prescription message 425 may include parameters for an infusion rate and/or bolus amount. The administration processor 2308 may determine the rate parameter by dividing the total solution per day by the number of minutes in a day or a number of minutes specified for the administration. The example administration processor 2308 is configured to structure the above-mentioned parameters into defined fields or labels within the pump prescription message 425. The example pump 422 is configured to search for certain fields or labels to program the value of the parameters into corresponding operational settings of the pump. In instances where multiple bags or packets are to be used, the administration processor 2308 may specify a channel or pump for each bag or packet.

e. Example Process to Program a Nutritional Pump Based on a Patient's Nutritional Status FIG. 25 shows a flow diagram illustrating an example procedure 2500 to program a nutritional infusion pump 422 based on a patient's nutritional status determined by the soft tissue engine 440 of FIG. 6, according to an example embodiment of the present disclosure. The example procedure 2500 may be carried out by, for example, the nutritional analysis engine 442 of the analysis server 408, as described in conjunction with FIGS. 4, 5, and 22 to 24. Although the procedure 2500 is described with reference to the flow diagram illustrated in FIG. 25, it should be appreciated that many other methods of performing the functions associated with the procedure 2500 may be used. For example, the order of many of the blocks may be changed, certain blocks may be combined with other blocks, and many of the blocks described are optional.

The procedure 2500 begins when the nutritional analysis engine 442 receives one or more messages 414 that include a nutritional status record 618 and/or data distribution data 612 (block 2502). The nutritional analysis engine 442 determines if one (or more) alarm or alert is to be generated (block 2504). For instance, as described in conjunction with the alarm-alert generator 2304 of FIG. 23, the information in the nutritional status record 618 and/or data distribution data 612 is analyzed or compared to one or more predetermined thresholds and/or ranges. If a patient's nutritional status indicates that a patient is healthy (e.g., the patient has sufficient muscle quality and/or quantity), the nutritional analysis engine 442 determines that an alarm or alert is not needed. At this point, the nutritional analysis engine 442 refrains from generating an alarm or alert and returns to block 2502 to receive a nutritional status for another patient.

However, if the nutritional analysis engine 442 determines that an alarm or an alert is to be generated, the nutritional analysis engine 442 creates the alarm and/or alert and transmits one (or more) message(s) 430 indicative of the alarm and/or alert (block 2506). The alarm and/or alert message 430 may identify the patient and the nutritional status of the patient. The alarm and/or alert may include a link or field that enables a clinician to respond with an override, an indication that a prescription is to be prepared, and/or prescription order information. The example nutritional analysis engine 442 next determines if a nutrition prescription order has been received from a clinician device 424 and/or the EMR server 426. For instance, a clinician, upon receiving an alert or alarm, may create a prescription order for a nutritional therapy. The prescription order may be used by the pharmacy preparation system 420 to prepare a nutritional solution. The prescription order may also be used to program one of the pumps 422.

If a prescription order is provided, the nutritional analysis engine 442 creates a pharmacy order providing instructions to the pharmacy preparation system 420 for preparing a nutritional solution (block 2510). This includes creating a solution composition record 2307 used to program a compounding system within a pharmacy preparation system 420. In some instances, the nutritional analysis engine 442 may determine specific components for the solution based on the prescription. For instance, a prescription may specify that a patient is to receive four days of an amino acid enhanced parenteral nutritional solution. The prescription may also indicate, for example, that 2200 ml of the solution is to be administered per day and include, for example, 55 g/l of amino acid. The nutritional analysis engine 442 creates the record 2307 based on the prescription by identifying specific components or ingredients, such as proline, in addition to concentrations or amounts of the components that are to be part of the solution. The nutritional analysis engine 442 stores the components and amounts to the record 2307 for transmission to the pharmacy preparation system 420.

If a prescription order is not provided, the nutritional analysis engine 442 determines a nutritional solution from scratch according to one or more algorithms or routines (block 2511). The example nutritional analysis engine 442 uses a patient's nutritional status, soft tissue peak, and/or soft tissue peak information to determine a volume of solution to be administered per day (or specified time period). The example nutritional analysis engine 442 may also determine an amino acid concentration, lipid concentration, and/or glucose concentration. Further, the nutritional analysis engine 442 determines micronutrient additives to incorporate into the solution. In some instances, the nutritional analysis engine 442 may compare a patient's soft tissue peak and/or related information to a population correlated to solution compositions. The nutritional analysis engine 442 may select the solution composition that most closely matches soft tissue peak and/or related information of individuals in the population.

The example nutritional analysis engine 442 may also determine values for administration parameters for a nutritional therapy pump prescription message 425 (block 2512). The parameters include, for example, an infusion rate, a total volume to be infused, a solution name and/or identifier, a solution (amino-acid) concentration, a patient name and/or identifier, a pump name and/or identifier, and/or a patient weight. In some instances, the nutritional analysis engine 442 may access a patient's EMR to determine at least some of the values for the nutritional therapy pump prescription message 425. For example, a patient's EMR may include patient information in addition to an identifier of the pump 422 that will administer the solution to the patient. In other instances, the nutritional analysis engine 442 leaves the pump identifier field blank. This field may be determined by the EMR server 426 after it receives an identifier from a barcode scanner reading an electric or printed barcode on a pump and on a patient. The nutritional analysis engine 442 may also use information within record 2307 for determining values for the administration parameters. For example, infusion rate, solution name, and solution concentration may be determined from the record 2307.

After determining values for the administration parameters, the nutritional analysis engine 442 creates a nutritional therapy pump prescription message 425 for the infusion pump 422 (block 2514). This may include structuring the parameter values within an HL7-compliant message. The value for each parameter may be stored with an appropriate label or field within the message 425. The nutritional analysis engine 442 transmits the nutritional therapy pump prescription message 425 to, for example, the infusion pump 422 (or the EMR server 426 for routing to the infusion pump 422). The infusion pump 422 identifies the parameter values based on labels and/or fields and populates an application or routine with the parameter values. The infusion pump 422 may then administer the nutritional therapy and operate based on the specified parameters. At this point, the example procedure 2500 returns to block 2502 for the next patient.

CONCLUSION

It will be appreciated that all of the disclosed methods and procedures described herein may be implemented using one or more computer programs or components. These components may be provided as a series of computer instructions on any conventional computer-readable medium, including RAM, ROM, flash memory, magnetic or optical disks, optical memory, or other storage media. The instructions may be configured to be executed by a processor, which when executing the series of computer instructions performs or facilitates the performance of all or part of the disclosed methods and procedures.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims.

It should be appreciated that 35 U.S.C. 112(f) or pre-AIA 35 U.S.C. 112, paragraph 6 is not intended to be invoked unless the terms "means" or "step" are explicitly recited in the claims. Accordingly, the claims are not meant to be limited to the corresponding structure, material, or actions described in the specification or equivalents thereof.

The invention is claimed as follows:

1. A parenteral nutritional diagnostic system comprising:
   a computed tomography ("CT") imaging device configured to:
   perform a scan on a mid-section of a patient, and
   produce a set of two-dimensional images each of a slice at a different cross-sectional height of the mid-section, each two-dimensional image including radiodensity data related to imaged tissue of the patient;
   a soft tissue analysis server communicatively coupled to the CT imaging device and configured to:
   select a target two-dimensional image among the set of two-dimensional images by using the radiodensity data to determine which of the two-dimensional images includes a lowest amount of bone tissue, use the target two-dimensional image to determine a tissue surface area for each different value of radiodensity, create a distribution plot of the tissue surface area for each radiodensity value in Hounsfield Units ("HU"), locate a soft tissue peak within the distribution plot that corresponds to a local peak in the range of −50 HU and 80 HU, and transmit an indication of the soft tissue peak;

a pharmacy preparation system communicatively coupled to the soft tissue analysis server and configured to:

determine a parenteral nutritional treatment is to be performed before a medical procedure is to be performed for the patient when the soft tissue peak occurs below a predetermined threshold that includes a value between 28 HU and 50 HU and corresponds to a nutritionally unhealthy patient, determine a nutritional order parameter of the parenteral nutritional treatment based at least in part on the soft tissue peak, and transmit the nutritional order parameter of the parenteral nutritional treatment; and a parenteral nutrition pump communicatively coupled to the pharmacy preparation system and configured to:

program a parenteral nutrition infusion therapy based on the received nutritional order parameter of the parenteral nutritional treatment, and provide the parenteral nutrition infusion therapy to the patient.

2. The system of claim 1, further comprising an electronic medical records server configured to:

receive and store the soft tissue peak;

compare the soft tissue peak to the predetermined threshold;

transmit an alarm when the soft tissue peak is below the predetermined threshold; and transmit a message to the pharmacy preparation system indicative that the parenteral nutritional treatment is to be performed.

3. The system of claim 1, wherein the nutritional order parameter of the parenteral nutritional treatment includes at least one of a nutrition volume to be infused, a nutrition solution to be infused, an infusion rate, or an infusion duration.

4. The system of claim 3, wherein the nutrition solution includes at least one of a carbohydrate, a lipid, a protein, sodium, potassium, calcium, iron, magnesium, phosphate, acetate, chloride, folic acid, an amino acid, an omega-3 fatty acid, a vitamin, and a supplement.

5. The system of claim 1, wherein the pharmacy preparation system is configured to at least one of:

(i) prepare a nutritional substance for the parenteral nutrition infusion therapy based at least in part on the soft tissue peak; or (ii) select a premix container for the parenteral nutrition infusion therapy based at least in part on the soft tissue peak.

6. The system of claim 5, wherein the pharmacy preparation system is configured to determine the nutritional order parameter and perform at least one of (i) and (ii) based additionally on at least one of an age of the patient, a gender of the patient, a weight of the patient, a disease state of the patient, a physiological parameter of the patient, and the medical procedure to be performed on the patient.

7. The system of claim 1, wherein the parenteral nutrition pump includes a large volume pump or a gravity-operated pump.

8. A parenteral nutritional diagnostic apparatus operable with at least one imaging device, the apparatus comprising:

at least one processor communicatively coupled to the at least one imaging device and configured to:

receive a set of medical images, each medical image (i) taken of a different cross-section of a patient, and (ii) including radiodensity data related to imaged tissue of the patient, select a target medical image among the set of medical images that corresponds to a desired area of the patient, use the target medical image to determine a tissue area for each different value of radiodensity, determine a distribution of the tissue area for each radiodensity value, locate a soft tissue peak within the distribution that corresponds to a local peak at a region in the distribution that is related to muscle tissue, organ tissue, and intramuscular adipose tissue, determine a nutritional status for the patient based on whether the soft tissue peak occurs below a predetermined threshold that includes a value between 28 HU and 50 HU and corresponds to a nutritionally unhealthy patient, and provide information indicative of the nutritional status of the patient.

9. The apparatus of claim 8, wherein the different cross-sections are different lateral cross-sections of a mid-section of the patient.

10. The apparatus of claim 8, wherein the desired area of the patient is between a third lumbar vertebra and a fourth lumbar vertebra.

11. The apparatus of claim 8, wherein the at least one processor is further configured to:

transmit a message indicative that a nutritional treatment before another medical procedure is not needed when the nutritional status is greater than the predetermined threshold; and transmit a message indicative the patient should undergo the nutritional treatment when the nutritional status is less than the predetermined threshold.

12. The apparatus of claim 8, wherein the at least one processor is further configured to determine the tissue area for each different value of radiodensity by:

creating a number of bins between −150 HU and 150 HU, each bin corresponding to a different value of radiodensity;

assigning each pixel from the target medical image to one of the bins; and determining a tissue area for each bin by summing the pixels assigned to the respective bin.

13. The apparatus of claim 12, wherein the bins have a width between 0.1 HU and 2 HU.

14. The apparatus of claim 12, wherein each of the pixels within the target medical image is color-coded based on the radiodensity of the tissue shown within the pixel.

15. The apparatus of claim 8, wherein the at least one processor is further configured to:

determine a center-of-mass within the target medical image;

impose a region-of-interest over the target medical image such that a geometric center of the region-of-interest is aligned with the center-of-mass; and determine a first tissue area for each different value of radiodensity of the target medical image that corresponds to the region-of-interest.

16. The apparatus of claim 15, wherein the center-of-mass is a first center-of-mass, and the region-of-interest is a first region-of-interest, and wherein the at least one processor is configured to:
identify bone tissue within the first region-of-interest;
determine a second center-of-mass within the first region-of-interest using only the bone tissue;
impose a second region-of-interest to replace the first region-of-interest over the target medical image such that a geometric center of the second region-of-interest is aligned with the second center-of-mass; and
determine a second tissue area for each different value of radiodensity of the target medical image that corresponds to the second region-of-interest.

17. A parenteral nutritional diagnostic method comprising:
acquiring in at least one processor from an imaging device, a set of medical images each of a slice at a different cross-section of a patient, each image including radiodensity data related to imaged tissue of the patient;
analyzing, via the at least one processor, the set of medical images to determine a total bone tissue area that corresponds to a designated area of the patient;
selecting, via the at least one processor, a target medical image from the set of analyzed medical images that has a lowest total bone tissue area;
determining, via the at least one processor from the target medical image, a distribution of radiodensity values;
identifying, via the at least one processor, a local peak at a region in the distribution of radiodensity values that is related to at least one of muscle tissue, organ tissue, or intramuscular adipose tissue;
evaluating, via the at least one processor, a first nutritional status of the patient when a radiodensity value of the local peak is within a first radiodensity range that includes a value greater than 50 HU and corresponds to a nutritionally healthy patient; and
evaluating, via the at least one processor, a second nutritional status of the patient when a radiodensity value of the local peak is within a second radiodensity range that includes a value between 28 HU and 50 HU and corresponds to a nutritionally unhealthy patient.

18. The method of claim 17, further comprising smoothing the distribution of radiodensity values using at least one of a Savitzky—Golay digital filter, a moving-average filter, a multipass filter, or a convolution filter.

19. The method of claim 17, wherein the distribution of radiodensity values includes at least one of (i) a number of pixels of the target medical image for each radiodensity value, or (ii) a tissue surface area of tissue provided in the target medical image for each radiodensity value.

20. The method of claim 17, further comprising:
determining, via the at least one processor, that at least one of an alarm or an alert is to be generated based on the patient having the second nutritional status; and
transmitting, via the at least one processor, the at least one of the alarm or the alert to at least one of a clinician device, a pharmacy preparation system, and an electronic medical record server.

21. The method of claim 17, further comprising:
determining, via the at least one processor, (i) a component or composition of a nutritional solution, and (ii) a total volume of the nutritional solution to be administered based on the patient having the second nutritional status and at least one demographic trait of the patient; and
providing, via the at least one processor, (i) and (ii) to a pharmacy preparation system to prepare the nutritional solution.

22. The method of claim 21, further comprising:
determining, via the at least one processor, administration parameters for an infusion pump based on (i) and (ii);
creating, via the at least one processor, an administration message that includes the administration parameters and an identifier of the patient; and
transmitting, via the at least one processor, the administration message to the infusion pump to cause a nutritional therapy to be administered to the patient identified by the identifier and according to the administration parameters.

* * * * *